United States Patent
Murray et al.

(10) Patent No.: US 8,642,735 B2
(45) Date of Patent: *Feb. 4, 2014

(54) BIOLOGIC REPLACEMENT FOR FIBRIN CLOT

(75) Inventors: Martha M. Murray, Sherborn, MA (US); Michael F. Murray, Sherborn, MA (US); Jennifer Marler, Arlington, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/449,449

(22) Filed: Apr. 18, 2012

(65) Prior Publication Data

US 2012/0201896 A1 Aug. 9, 2012

Related U.S. Application Data

(60) Continuation of application No. 13/215,369, filed on Aug. 23, 2011, now abandoned, which is a continuation of application No. 12/900,216, filed on Oct. 7, 2010, now abandoned, which is a division of application No. 11/092,992, filed on Mar. 29, 2005, now Pat. No. 7,838,630, which is a continuation of application No. 09/917,058, filed on Jul. 27, 2001, now Pat. No. 6,964,685, which is a continuation-in-part of application No. 09/594,295, filed on Jun. 15, 2000, now abandoned.

(60) Provisional application No. 60/182,972, filed on Feb. 16, 2000, provisional application No. 60/140,197, filed on Jun. 22, 1999.

(51) Int. Cl.
*A61K 38/17* (2006.01)
*A61K 35/16* (2006.01)
*A61P 19/04* (2006.01)

(52) U.S. Cl.
USPC ............................................. 530/356; 424/530

(58) Field of Classification Search
USPC .......................................... 530/356; 424/530
See application file for complete search history.

(56) References Cited

U.S. PATENT DOCUMENTS

| | | |
|---|---|---|
| 2,127,903 A | 8/1938 | Bowen |
| 3,176,316 A | 4/1965 | Bodell |
| 3,373,906 A | 3/1968 | De Hart et al. |
| 3,587,982 A | 6/1971 | Campbell |
| 3,738,535 A | 6/1973 | Nicholls |
| 3,774,604 A | 11/1973 | Danielsson |
| 3,797,499 A | 3/1974 | Schneider |
| 4,069,814 A | 1/1978 | Clemens |
| 4,186,448 A | 2/1980 | Brekke |
| 4,265,618 A | 5/1981 | Herskovitz |
| 4,458,678 A | 7/1984 | Yannas et al. |
| 4,467,806 A | 8/1984 | Bhiwandiwala et al. |
| 4,578,067 A | 3/1986 | Cruz |
| 4,585,458 A | 4/1986 | Kurland |
| 4,753,536 A | 6/1988 | Spehar et al. |
| 4,808,184 A | 2/1989 | Tepic |
| 4,808,570 A | 2/1989 | Michaeli |
| 4,846,835 A | 7/1989 | Grande |
| 4,851,513 A | 7/1989 | Devore et al. |
| 4,894,063 A | 1/1990 | Nashef |
| 4,932,942 A | 6/1990 | Maslanka |
| 4,955,893 A | 9/1990 | Yannas et al. |
| 4,959,058 A | 9/1990 | Michelson |
| 4,973,321 A | 11/1990 | Michelson |
| 5,037,396 A | 8/1991 | Streeter |
| 5,078,744 A | 1/1992 | Chvapil |
| 5,119,669 A | 6/1992 | Silvis et al. |
| 5,152,462 A | 10/1992 | Evans |
| 5,171,273 A | 12/1992 | Silver et al. |
| 5,206,023 A * | 4/1993 | Hunziker ...................... 424/423 |
| 5,281,422 A | 1/1994 | Badylak et al. |
| 5,380,087 A | 1/1995 | Haber et al. |
| 5,455,833 A | 10/1995 | Herre et al. |
| 5,503,616 A | 4/1996 | Jones |
| 5,522,840 A | 6/1996 | Krajicek |
| 5,556,429 A | 9/1996 | Felt |
| 5,595,621 A | 1/1997 | Light et al. |
| 5,652,077 A | 7/1997 | Obinata |
| 5,655,546 A | 8/1997 | Halpern |
| 5,681,353 A * | 10/1997 | Li et al. ...................... 623/14.12 |
| 5,713,374 A | 2/1998 | Pachence et al. |
| 5,749,895 A | 5/1998 | Sawyer et al. |
| 5,810,884 A | 9/1998 | Kim |
| 5,897,591 A | 4/1999 | Kobayashi |
| 5,902,741 A | 5/1999 | Purchio et al. |
| RE36,370 E | 11/1999 | Li |

(Continued)

FOREIGN PATENT DOCUMENTS

EP 0295721 A2 12/1988
EP 0445951 A2 9/1991

(Continued)

OTHER PUBLICATIONS

Louie et al., Tissue Engineering 3, No. 2, 187-195 (1997).*
U.S. Appl. No. 13/662,510, filed Oct. 28, 2012, Slocum et al.
U.S. Appl. No. 13/862,554, filed Apr. 15, 2013, Murray.
PCT/US2002/023885, Apr. 4, 2003, International Search Report.
PCT/US2002/023885, Jun. 26, 2003, Written Opinion.
PCT/US2002/023885, Mar. 11, 2004, International Preliminary Report on Patentability.
EP 06720499.0, Jul. 16, 2009, Extended European Search Report.
PCT/US2006/004445, Jul. 1, 2008, International Search Report and Written Opinion.
PCT/US2006/004445, Feb. 26, 2009, Internaional Preliminary Report on Patentability.

(Continued)

*Primary Examiner* — Chih-Min Kam
(74) *Attorney, Agent, or Firm* — Wolf, Greenfield & Sacks, P.C.

(57) ABSTRACT

The invention provides composition and methods for repairing a ruptured anterior cruciate ligament.

20 Claims, 21 Drawing Sheets

(56) References Cited

U.S. PATENT DOCUMENTS

| | | | |
|---|---|---|---|
| 6,045,569 A | 4/2000 | Kensey et al. | |
| 6,080,192 A | 6/2000 | Demopulos et al. | |
| 6,087,113 A | 7/2000 | Caplan et al. | |
| 6,096,309 A | 8/2000 | Prior et al. | |
| 6,117,425 A | 9/2000 | MacPhee et al. | |
| 6,129,757 A | 10/2000 | Weadock | |
| 6,139,520 A | 10/2000 | McCrory et al. | |
| 6,153,292 A | 11/2000 | Bell et al. | |
| 6,171,610 B1 | 1/2001 | Vacanti et al. | |
| 6,176,880 B1 | 1/2001 | Plouhar et al. | |
| 6,214,049 B1 | 4/2001 | Gayer et al. | |
| 6,234,795 B1 | 5/2001 | Fischer | |
| 6,309,372 B1 | 10/2001 | Fischer et al. | |
| 6,365,149 B2 | 4/2002 | Vyakarnam et al. | |
| 6,454,129 B1 | 9/2002 | Green | |
| 6,472,210 B1 | 10/2002 | Holy et al. | |
| 6,629,997 B2 | 10/2003 | Mansmann et al. | |
| 6,689,153 B1 | 2/2004 | Skiba | |
| 6,699,214 B2 | 3/2004 | Gellman | |
| 6,946,003 B1 | 9/2005 | Wolowacz et al. | |
| 6,964,685 B2 | 11/2005 | Murray et al. | |
| 6,971,787 B2 | 12/2005 | Botrie et al. | |
| 6,989,034 B2 | 1/2006 | Hammer et al. | |
| 7,148,209 B2 | 12/2006 | Hoemann et al. | |
| 7,156,880 B2 | 1/2007 | Evans et al. | |
| 7,250,057 B2 | 7/2007 | Forsberg | |
| 7,335,220 B2 | 2/2008 | Khosravi et al. | |
| 7,652,077 B2 | 1/2010 | Cook et al. | |
| 7,838,630 B2 * | 11/2010 | Murray et al. | 530/356 |
| 7,901,461 B2 | 3/2011 | Harmon et al. | |
| 8,002,813 B2 | 8/2011 | Scarborough et al. | |
| 8,137,686 B2 | 3/2012 | Kladakis et al. | |
| 2002/0022884 A1 | 2/2002 | Mansmann | |
| 2002/0123805 A1 | 9/2002 | Murray et al. | |
| 2002/0161450 A1 | 10/2002 | Doi et al. | |
| 2002/0183845 A1 | 12/2002 | Mansmann et al. | |
| 2003/0012805 A1 | 1/2003 | Chen et al. | |
| 2003/0078659 A1 | 4/2003 | Yang | |
| 2003/0147935 A1 | 8/2003 | Binette et al. | |
| 2003/0163144 A1 | 8/2003 | Weadock et al. | |
| 2003/0167053 A1 | 9/2003 | Taufig | |
| 2004/0059416 A1 | 3/2004 | Murray et al. | |
| 2004/0078077 A1 | 4/2004 | Binette et al. | |
| 2004/0170664 A1 | 9/2004 | Spector et al. | |
| 2004/0258729 A1 | 12/2004 | Czernuszka et al. | |
| 2004/0262332 A1 | 12/2004 | Pauser et al. | |
| 2004/0267362 A1 | 12/2004 | Hwang et al. | |
| 2005/0027307 A1 | 2/2005 | Schwartz et al. | |
| 2005/0183731 A1 | 8/2005 | Hunter et al. | |
| 2005/0230422 A1 | 10/2005 | Muller et al. | |
| 2005/0261736 A1 | 11/2005 | Murray et al. | |
| 2007/0269476 A1 | 11/2007 | Voytik-Harbin et al. | |
| 2008/0195205 A1 | 8/2008 | Schwartz | |
| 2009/0143765 A1 | 6/2009 | Slocum et al. | |
| 2009/0254104 A1 | 10/2009 | Murray | |
| 2009/0306776 A1 | 12/2009 | Murray | |
| 2010/0221835 A1 | 9/2010 | Tanaka et al. | |
| 2011/0027338 A1 | 2/2011 | Murray et al. | |
| 2011/0306555 A1 | 12/2011 | Murray et al. | |
| 2012/0283831 A1 | 11/2012 | Murray | |

FOREIGN PATENT DOCUMENTS

| | | |
|---|---|---|
| GB | 2106794 | 4/1983 |
| WO | WO 85/00511 | 2/1985 |
| WO | WO 92/13565 A1 | 8/1992 |
| WO | WO 93/21857 A1 | 11/1993 |
| WO | WO 95/25550 A1 | 9/1995 |
| WO | WO 99/40771 A2 | 8/1999 |
| WO | WO 00/74760 A2 | 12/2000 |
| WO | WO 02/067812 A2 | 9/2002 |
| WO | WO 2004/078134 A2 | 9/2004 |
| WO | WO 2008/109807 A2 | 9/2008 |
| WO | WO 2010/048418 A1 | 4/2010 |
| WO | WO 2010/084481 A1 | 7/2010 |

OTHER PUBLICATIONS

PCT/US2007/001908, Oct. 31, 2007, International Search Report and Written Opinion.

PCT/US2007/001908, Aug. 7, 2008, International Preliminary Report on Patentability.

PCT/US2007/021009, Sep. 8, 2009, Invitation to Pay Additional Fees.

PCT/US2007/021009, Dec. 22, 2009, International Search Report and Written Opinion.

PCT/US2007/021009, Jan. 21, 2010, International Preliminary Report on Patentability.

PCT/US2013/024467, Apr. 29, 2013, International Search Report and Written Opinion.

Al-Munajjed et al., Development of a collagen calcium-phosphate scaffold as a novel bone graft substitute. Stud Health Technol Inform. 2008;133:11-20.

Anseth et al., Polymerizable degradable plyanhydrides with osteocompatibility, 17(2) Nature Biotechnol. 156-159 (Feb. 1999).

Arendt and Dick, Knee injury patterns among men and women in collegiate basketball and soccer, 23(6) Am. J. Sports Med. 694-701 (1995).

Buck, Regeneration of Tendon, 66(1) J. Pathol. Bacteriol. 1-18 (1953).

Chamberlain et al., Early peripheral nerve healing in collagen and silicone tube implants: myofibroblasts and the cellular response, 19 Biomaterials 1393-1403 (1998).

Chamberlain, Collagen-GAG Substrate Enhances the Quality of Nerve Regeneration through Collagen Tubes up to Level of Autograft, 154(2) Experimental Neurology 315-329 (Dec. 1998).

Chamberlain, Long term functional and morphological evaluation of peripheral nerves regenerated through degradable collagen implants, (M.S. Thesis, Massachusetts Institute of Technology, 1998) (copy on file with the MIT library).

Deie et al., High intrinsic healing potential of human anterior cruciate ligament, 66(1) Acta. Orthop. Scand. 28-32 (1995).

Desrosiers et al., Proliferative and matrix synthesis response of canine anterior cruciate ligament fibroblasts submitted to combined growth factors, 14(2) J. Orthop. Res. 200-208 (1996).

Dye, The Future of Anterior Cruciate Ligament Restoration, 325 CLIN. Orthop. 130-139 (1996).

Faryniarz, et al., Myofibroblasts in the healing lapine medial collateral ligament: possible mechanisms of contraction, 14(2) J. Orthop. Res. 228-237 (1996).

Ferber, Lab Grown Organs Take Shape, 284(5413) Science 422-425 (Apr. 16, 1999).

Ferber, Tissue Engineering: From the Lab to the Clinic, 284(5413) Science 422-425 (Apr. 16, 1999).

Ford et al., Autologous Collagen Vocal Fold Injection: A Preliminary Clinical Study, 105 Laryngoscope 944-948 (Sep. 1995).

Frank et al., Natural History of Healing in the Repaired Medical Collateral Ligament, 1(2) J. Orthop. Res. 179-188 (1983).

Geiger et al., An in vitro assay of anterior cruciate ligament (ACL) and medial collateral ligament (MCL) cell migration, 30(3) Connect Tissue Res. 215-224 (1994).

Gerich et al., Gene transfer to the patellar tendon, Knee Surg, Sports Traumatol, Arthroscopy (1997) 5:118-123.

Guidance document for testing biodegradable polymer implant devices, Division of General and Restorative Devices, Center for Devices and Radiological Health, U.S. Food and Drug Administration (Apr. 20, 1996).

Gwinn et al., Relative general incidence of anterior cruciate ligament injury at a military service academy, 66th Annual Meeting of Amer. Acad. of Orthop. Surg., Anaheim, California (1999).

Hefti et al., Healing of the Transected Anterior Cruciate Ligament in the Rabbit, 73A (3) J. Bone Joint Surg. 373-383 (Mar. 1991).

Jackson et al., Biologic remodeling after anterior cruciate ligament reconstruction using a collagen matrix derived from demineralized bone: an experimental study in the goat model, 24(4) Am. J. Sports Med. 405-414 (Jul.- Aug. 1996).

(56) References Cited

OTHER PUBLICATIONS

Kato et al., Formation of continuous collagen fibres: evaluation of biocompatibility and mechanical properties, 11 Biomaterials 169-175 (Apr. 1990).

Kawamoto et al., Selective migration of alpha-smooth muscle actin-positive myofibroblasts toward fibronectin in the Boyden's blindwell chamber, 93(4) Clin. Sci. 355-362 (1997).

Louie, Effect of a porous collagen-glycosaminoglycan copolymer on early tendon healing in a novel animal model, (Ph.D. Thesis, Massachusetts Institute of Technology, 1997) (copy on file with the MIT Library).

Louie, L. K., et al., Development of a collagen-GAG copolymer implant for the study of tendon regeneration, M331 Mat. Res. Soc. Symp. Proc. 19-24 (1994).

Marshall et al., The Anterior Cruciate Ligament: A Technique of Repair and Reconstruction, 143 Clin. Orthop. 97-106 (Sep. 1979).

Masur et al., Myofibroblasts differentiate from fibroblasts when plated at low density, 93(9) Proc. Nat'l Acad. Sci. USA 4219-4223 (Apr. 1996).

Murray et al., Differences in the outgrowth of cells from explants from the proximal and distal human ACL and response to TGF-B1, Transactions of the 47th Annual Meeting of the Orthopaedic Research Society, Feb. 25-28, 2001; San Francisco, CA.

Murray et al., Fibroblast distribution in the anteriomedial bundle of the human anterior cruciate ligament: The presence of alpha smooth muscle actin-positive cells, 17(1) J. Orthop. Res. 18-27 (1999).

Murray et al., Histological changes in the human anterior cruciate ligament after rupture, 82A(10) J. Bone Joint Surg. 1387-1397 (2000).

Murray et al., Migration of cells from human anterior cruciate ligament explants into collagen-glycosaminoglycan scaffolds, 18(4) J. Orthop. Res. 557-564 (2000).

Murray et al., Migration of cells from ruptured human anterior cruciate ligament explants into collagen-GAG matrices, Proceedings of the Sixth World Biomaterials Congress, 2000; Kamuela, Hawaii.

Murray et al., Migration of human anterior cruciate ligament fibroblasts into porous collagen-GAG matrices in vitro, 24th Annual Meeting of the Society for Biomaterials, Apr. 22-26, 1996, San Diego, CA p. 463.

Murray et al., The effect of ruptured human anterior cruciate ligament histology on cell interactions with a CG scaffold, Davos Tissue Engineering Workshop, 2000; Davos, Switzerland.

Murray et al., The effects of selected growth factors on human ACL cell interactions with 3-D collagen-GAG scaffolds, Transactions of the 47th Annual Meeting of the Orthopaedic Research Society, Feb. 25-28, 2001; San Francisco, CA.

Murray et al., The migration of cells from the ruptured human anterior cruciate ligament into collagen-glycosaminoglycan regeneration templates in vitro, 22 Biomat. 2393-2402 (2001).

Murray et al., The migration of human anterior cruciate ligament fibroblasts into porous collagen-GAG matrices in vitro, 45th Annual Meeting, Orthopedic Research Society, Anaheim, California (Feb. 1-4, 1999).

Murray, M.M., et al., Use of a collagen-platelet rich plasma scaffold to stimulate healing of a central defect in the canine ACL, J Orthop Res. Apr. 24, 2006(4):820-30. Abstract.

Nakamura et al., A comparison of in vivo gene delivery methods for antisense therapy in ligament healing, Gene Therapy (1998) 5: 1455-1461.

Nakamura et al., Early biological effect of in vivo gene transfer of platelet-derived growth factor (PDGF)-S into healing patellar ligament, Gene Therapy (1998) 5: 1165-1170.

Niklason et al., Functional arteries grown in vitro, 284(5413) Science 489-493 (Apr. 16, 1999).

Noyes et al., 72A(8) J. Bone Joint Surg. 1125-1136 (Sep. 1990).

Peter et al., Synthesis of poly(propylene fumarate) by acylation of propylene glycol in the presence of a proton scavenger, 10(3) J. Biomater. Sci. Polym. Ed. 363-373 (1999).

Qiu et al., Outgrowth of chondrocytes from human articular cartilage explants, and expression of alpha-smooth muscle actin, 18 Wound Repair and Regeneration 383-391 (Sep.-Oct. 2000).

Schmidt et al., Effect of growth factors on he proliferation of fibroblasts from the medial collateral and anterior cruciate ligaments, 13(2) J. Orthop. Res. 184-190 (1995).

Spindler et al., Comparison of collagen synthesis in the peripheral and central region of the canine meniscus, 303 Clinical Orthopaedics 256-263 (Jun. 1994).

Spindler et al., Patellar tendon and anterior cruciate ligament have different mitogenic responses to platelet-derived growth factor and transforming growth factor Beta, 14(4) J. Orthop. Res. 542-546 (1996).

Spindler et al., Regional mitogenic response of the meniscus to platelet-derived growth factor (PDGF-AB), 13(2) J. Orthop. Res. 201-207 (1995).

Stevenson, Gender differences in knee injury epidemiology among competitive alpine ski racers, 18 Iowa Orthop. J. 64-66 (1998).

Stone et al., Future Directions: Collagen-Based Prostheses for Meniscal Regeneration, 252 Clinical Orthopaedics and Related Research 129-135 (Mar. 1990).

Stone et al., Regeneration of Meniscal Cartilage with Use of a Collagen Scaffold, 79A(12) J. Bone and Joint Surg. 1770-1777 (Dec. 1997).

Suggs et al., Platelet adhesion on a bioresorgable poly(propylene fumarate-co-ethylene glycol) copolymer, 20(7) Biomaterials 683-690 (1999).

Torres, Effects of modulus of elasticity of collagen sponges on their cell-mediated contraction in vitro, M. S. Thesis, Massachusetts Institute of Technology (1998) (copy on file with the MIT Library).

Troxel, Delay of skin wound contraction by porous collagen-GAG matrices, (Ph. D. Thesis, Massachusetts Institute of Technology, 1994) (on file with the MIT Library).

Weadock et al., Physical crosslinking of collagen fibers: comparison of ultraviolet irradiation and dehydrothermal treatment, 29 J. Biomed. Mater. Res. 1373-1379 (1995).

Witkowski et al., Migration and Healing of Ligament Cells under Inflammatory Conditions, 15(2) J. Orthop. Res. 269-277 (1997).

Yannas et al., Synthesis and characterization of a model extracellular matrix that induces partial regeneration of adult mammalian skin, 86 Proc. Natl. Acad. Sci USA 933-937 (Feb. 1989).

Yannas, Models of Organ Regeneration Processes Induces by Templates, Bioartificial Organs: Science, Medicine, and Technology, Prokop al. Ed., pp. 280-293 (The New York Academy of Sciences, New York, NY 1997).

Yannas, Collagen vol. 3, Biotechnology, Nimni Ed., p. 87-115 (CRC Press, Boca Raton, Florida, 1989).

Yannas, et al., Polymeric template facilitates regeneration of sciatic nerve across 15-millimeter gap, 8 Trans. Soc. Biomater. 146 (1985).

* cited by examiner

INTACT HUMAN ACL

GEL WITH CELLS AT
3 HOURS OF CULTURE

GEL WITH CELLS AT
3 DAYS OF CULTURE

GEL WITH CELLS AT
9 DAYS OF CULTURE

BIOLOGIC REPLACEMENT FOR FIBRIN CLOT

CLAIM OF PRIORITY

This application is a continuation application which claims benefit under 35 U.S.C §120 of U.S. application Ser. No. 13/215,369, filed on Aug. 23, 2011, now abandoned which is a continuation application which claims benefit under 35 U.S.C §120 of U.S. application Ser. No. 12/900,216, filed on Oct. 7, 2010, now abandoned, which is a divisional application which claims benefit under 35 U.S.C. §121 of U.S. application Ser. No. 11/092,992, filed on Mar. 29, 2005, now U.S. Pat. No. 7,838,630, which is a continuation application which claims benefit under 35 U.S.C §120 of U.S. application Ser. No. 09/917,058, filed on Jul. 27, 2001, now U.S. Pat. No. 6,964,685, which is a continuation-in-part application which claims benefit under 35 U.S.C §120 of U.S. application Ser. No. 09/594,295 filed Jun. 15, 2000, now abandoned, which claims benefit under 35 U.S.C §119(e) of U.S. Provisional Application Ser. Nos. 60/182,972, filed Feb. 16, 2000, and 60/140,197, filed Jun. 22, 1999, the contents of each of which are herein incorporated by reference in their entireties.

GOVERNMENT SUPPORT

This invention was made with government support under Grant No.: R03 AR46356 awarded by the National Institutes of Health (NIH). The government has certain rights in the invention.

FIELD OF THE INVENTION

This invention relates generally to compositions and methods for repairing injured intra and extra-articular tissue.

BACKGROUND INFORMATION

Intra-articular tissues, such as the anterior cruciate ligament (ACL), do not heal after rupture. In addition, the meniscus and the articular cartilage in human joints also often fail to heal after an injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature degradation of the fibrin clot scaffold and disruption of the healing process for tissues within the joint or within intra-articular tissues.

The current treatment method for human anterior cruciate ligament repair after rupture involves removing the ruptured fan-shaped ligament and replacing it with a point-to-point tendon graft. While this procedure can initially restore gross stability in most patients, longer follow-up demonstrates many post-operative patients have abnormal structural laxity, suggesting the reconstruction may not withstand the physiologic forces applied over time (Dye, 325 Clin. Orthop. 130-139 (1996)). The loss of anterior cruciate ligament function has been found to result in early and progressive radiographic changes consistent with joint deterioration (Hefti et al., 73A (3) J. Bone Joint Surg. 373-383 (1991)). As anterior cruciate ligament rupture is most commonly an injury of a young athletes, early osteoarthritis in this group has difficult consequences.

Thus, there is a need in the orthopedic art for a device that reproduces the function of the fibrin clot to re-connect extra-articular tissues in the early phase of healing. A therapeutic intervention that would facilitate anterior cruciate ligament regeneration or healing could offer several advantages over anterior cruciate ligament reconstruction. With anterior cruciate ligament regeneration or healing, the fan-shaped multiple fascicle structure could be preserved, the complex bony insertion sites could remain intact, and the proprioceptive function of the ligament could be retained.

SUMMARY OF INVENTION

The invention provides a composition of collagen, an extracellular matrix protein, and a platelet. The invention further provides a composition of collagen, a platelet and a neutralizing agent, e.g. sodium hydroxide or hydrochloric acid.

Further provided by the invention is a tissue adhesive composition of collagen, an extracellular matrix protein, and a platelet formulated for the administration to a patient. Additionally, the invention provides a composition of collagen, a platelet and a neutralizing agent, e.g. sodium hydroxide or hydrochloric acid formulated for the administration to a patient. The patient is preferably a mammal. The mammal can be, e.g., a human, non-human primate, mouse, rat, dog, cat, horse, or cow. In various aspects the platelet is derived from the patient. In other aspects the platelet is derived from a donor that is allogeneic to the patient.

The collagen can be of the soluble or the insoluble type. Preferably, the collagen is soluble, e.g., acidic or basic. For example the collagen can be type I, II, III, IV, V, IX or X. Preferably the collagen is soluble. More preferably the collagen is soluble type I collagen. An extracellular matrix protein includes for example elastin, laminin, fibronectin and entectin.

The compositions of the invention can additionally include plasma. In some aspects, the plasma is derived from the patient. In other aspects the plasma is derived from a donor that is allogeneic to the patient.

Alternatively, the composition includes one or more additives, such as insoluble collagen, a growth factor, a cross-linking agent, a stem cell, a genetically altered fibroblast and a cell media supplement. Growth factor includes for example, platelet derived growth factor-AA (PDGP-AA), platelet derived growth factor-BB (PDGF-BB), platelet derived growth factor-AB (PDGF-AB), transforming growth factor beta (TGF-β), epidermal growth factor (EGF), acidic fibroblast growth factor (aFGF), basic fibroblast growth factor (bFGF), insulin-like growth factor-1 (IGF-1), interleukin-1-alpha (IL-1α), and insulin.

By cross-linking agent is meant that the agent is capable of forming chemical bonds between the constituents of the composition. The cross-linking agent can be for example, a protein or a small molecule, e.g., glutaraldehyde or alcohol.

Cell media supplement is meant to include for example glucose, ascorbic acid, antibiotics, or glutamine.

The invention provided methods of treating an intra-articular injury in a subject, by contacting the ends of a ruptured tissue from the subject with a composition of the invention. Intra-articular injuries include for example a meniscal tear, ligament tear or a cartilage lesion.

The invention further provides a method of treating an extra-articular injury in a subject, by contacting the ends of a ruptured tissue from the subject with a composition of the invention. Extra-articular injuries include for example, injuries of the is ligament, tendon, bone or muscle.

In some aspects the methods further include mechanically joining the ends of the ruptured tissue, e.g., suturing.

The invention provides devices (e.g., tissue-adhesive composition) and methods for promoting a connection between the ruptured ends of the tissue and fibers after injury, by encouraging the migration of appropriate healing cells to form scar and new tissue in the device. The device is a bioengineered substitute for the fibrin clot and is implanted between the ruptured ends of the ligament fascicles. This substitute scaffold is designed to stimulate cell proliferation and extracellular matrix production in the gap between the ruptured ends of the anterior cruciate ligament, thus facilitating healing and regeneration. The device resists premature degradation of the replacement clot by the intra-synovial environment.

In one embodiment, the invention provides a three-dimensional (3-D) scaffold composition for repairing a ruptured anterior cruciate ligament (ACL) and a method for attaching the composition to the ruptured anterior cruciate ligament. The scaffold composition includes an inductive core, made of collagen or other material, and is surrounded by a layer critical to the attachment of the core to the surrounding tissue, called the adhesive zone. After the scaffold composition is inserted into the region between the torn ends of the anterior cruciate ligament and adhesively attached to the ends of the ligament, the adhesive zone provides a microenvironment for inducing fibroblast cells from the anterior cruciate ligament to migrate into the scaffold. After migrating into the inductive core of the scaffold, the fibroblast cells conform to the collagen structure between the ligament and heal the gap between the ruptured ends.

The invention also includes the use of a collagen-based glue as an adhesive to maintain contact between the torn edges of the meniscus. The torn edges of the meniscus are pretreated to expose selected extracellular matrix components in the meniscus. Then, the glue is introduced into the tear. Bonds are formed between the extracellular matrix in the meniscal tissue and the material of the glue. The bonds form a bridge across the gap in the meniscus. This adhesive zone bridge can then induce the migration of cells to the bridge, which is then remodeled by the meniscal cells, thus healing the tear.

This invention further includes the use of a collagen-based scaffold as an adhesive, e.g. tissue-adhesive composition (as well as a cell migration inducer) to maintain and restore contact between the torn cartilage and the surrounding cartilage and bone. The torn edges are pretreated to expose the extracellular matrix components in the cartilage. A collagen scaffold (e.g. tissue-adhesive composition) is then introduced into the tear. Bonds are formed between the extracellular matrix of the torn tissue and the material of the glue. The bonds form a bridge across the gap in the articular cartilage. This adhesive zone bridge can then induce the migration of cells to the bridge, which is remodeled by the cartilage cells, thus healing the injured area.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 15 is a schematic of the gross and histologic appearance of the four phases of the healing response in the human anterior cruciate ligament.

DETAILED DESCRIPTION

The invention provides compositions, e.g. a tissue-adhesive composition that are useful for repairing injured intra and extra-articular tissue. For example the compositions can be used in the repair of many tissues within articular joints, including the anterior cruciate ligament, knee meniscus, glenoid labrum, and acetabular labrum. Additionally, the compositions can be used to repair bone fractures, especially where the bone fractures are located in an intra-articular environment.

The compositions of the invention, can be incorporated into pharmaceutical compositions and administered to a subject.

The invention also provides methods of treating intra and extra articular injuries in a subject, e.g., mammal by contacting the ends of a ruptured tissue from the subject with the compositions of the invention. Intra-articular injuries include for example, meniscal tears, ligament tears and cartilage lesion. Extra-articular injuries include for example injuries to the ligament, tendon or muscle.

The device and compositions of the invention promotes regeneration of the human anterior cruciate ligament. Regeneration offers several advantages over reconstruction, including maintenance of the complex insertion sites and fan-shape of the ligament, and preservation of remaining proprioceptive fibers within the ligament substance. The invention provides a scaffold (e.g., tissue adhesive compositions) which the patient's body can develop a network of capillaries, arteries, and veins. Well-vascularized connective tissues heal as a result of migration of fibroblasts into the scaffold. Wound closure is subsequently facilitated by a contractile cell. The invention also permits the re-enervation of the damaged area by providing a cellular substrate for regenerating neurons.

The advantages of the invention also include (1) a less invasive treatment as compared with the current techniques, which involve drilling into the bone; (2) faster surgery (as opposed to current meniscal repair techniques); (3) no donor site morbidity (as is seen with harvesting tendon grafts); (4) a quicker healing time; (5) a greater likelihood of the restoration of the normal function of the ligament (because the collagen scaffold is repopulated by the patient's own ligament cells); and (6) restoration of the meniscal structure (as contrasted with meniscectomy) or the articular cartilage structure (as contrasted with total joint arthroplasty). Implanting a device that facilitates the migration of the patient's own cells to the injured area (1) eliminates the waiting time for ex vivo cell culture; (2) takes advantage of local nutritional sources and blood supply; (3) avoids the need for a second procedure; and (4) avoids the sudden change in nutritional environment seen by cells transferred from laboratory culture into a patient (see, Ferber, 284 (5413) Science 422-425 (1999); Ferber, 284 (5413) Science 423 (1999)).

Figure 1:
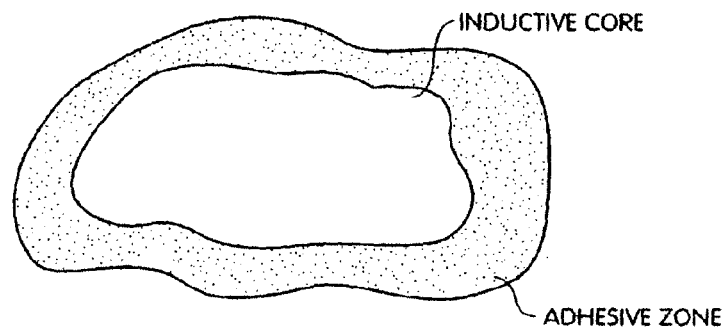
FIG. 1 is a schematic drawing of a replacement clot with an inductive core and an adhesive zone.

Inductive Core. Referring to the drawings, a biological replacement fibrin clot of the invention is shown in FIG. 1. The replacement fibrin clot includes a central inductive core surrounded by an adhesive zone.

The inductive core is preferably made of a compressible, resilient material which has some resistance to degradation by synovial fluid. The inductive core member may be made of either permanent or biodegradable materials.

Scaffolds that make up the inductive core may function either as insoluble regulators of cell function or simply as delivery vehicles of a supporting structure for cell migration or synthesis. Numerous matrices made of either natural or synthetic components have been investigated for use in ligament repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Many biological materials are available for making the inductive core, including collagen compositions (either collagen fiber or collagen gel), compositions containing glycosaminoglycan (GAG), hyaluran compositions, and various synthetic compositions. Collagen-glycosaminoglycan (CG) copolymers have been used successfully in the regeneration of dermis and peripheral nerve. Porous natural polymers, fabricated as sponge-like and fibrous scaffolds, have been investigated as implants to facilitate regeneration of selected musculoskeletal tissues including ligaments. Preferably the inductive core is soluble type I collagen, an extracellular matrix protein and a platelet.

An important subset of natural matrices are those made predominantly from collagen, the main structural component in ligament. Type I collagen is the predominant component of the extracellular matrix for the human anterior cruciate ligament. As such, it is a logical choice for the basis of a bioengineered scaffold for the inductive core. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

Porous collagen scaffolds of varying composition and architecture have been researched as templates for regeneration of a variety of tissues including bone, skin and muscle. A porous collagen-glycosaminoglycan (CG) scaffold has been used successfully in regeneration of dermis (Yannas et al., 86 Proc. Natl. Acad. Sci. USA 933-937 (1989)) and peripheral nerve (Chamberlain, *Long Term Functional And Morphological Evaluation Of Peripheral Nerves Regenerated Through Degradable Collagen Implants* (M.S. Thesis Massachusetts Institute of Technology, 1998) (on file with the MIT Library)).

Recent work has focused on the use of collagen fibers, to serve as scaffolds for the regeneration of the anterior cruciate ligament. The current design of these prostheses is as a substitute for the entire anterior cruciate ligament, that is the ruptured anterior cruciate ligament is removed from the knee and replaced by a point-to-point collagen graft (Jackson, 24 Am. J. Sports Med. 405-414 (1996)). Unlike the devices of the invention, these methods do not allow for the preservation of the complex geometry and insertion sites of the anterior cruciate ligament. These devices also require removal of the proprioceptive innervation of the anterior cruciate ligament. The devices of the invention, which facilitate the regeneration of defect caused by rupture while retaining the remainder of the ruptured ligament, would thus have potential advantages over the previous devices. Moreover, no studies to date have specifically investigated the use of any of these materials to serve as a provisional scaffold after primary repair of the anterior cruciate ligament, as provided by this invention.

Synthetic matrices are made predominantly of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus only degradable materials are preferred for work in regeneration. Degradable synthetic scaffolds can be engineered to control the rate of degradation.

The inductive core can be composed of foamed rubber, natural material, synthetic materials such as rubber, silicone and plastic, ground and compacted material, perforated material, or a compressible solid material. For example, the inductive core can be made of (1) an injectable high molecular weight poly(propylene fumarate) copolymer that hardens quickly in the body (Peter et al., 10 (3) J. Biomater. Sci. Polym. Ed. 363-73 (1999)); (2) a bioresorbable poly(propylene fumarate-co-ethylene glycol) copolymer (Suggs et al., 20 (7) Biomaterials 683-90 (1999)); (3) a branched, porous polyglycolic acid polymer coated with a second polylactide-coglycolide polymer (Anseth et al., 17 (2) Nature Biotechnol. 156-9 (1999)); or (4) a polyglycolic acid polymer, partially hydrolyzed with sodium hydroxide to create hydrophilic hydroxyl groups on the polymer that enable cells to attach (see, Niklason et al., 284 Science 489-493 (1999)). The latter material has been used as a scaffold for construction of bioartificial arteries in vitro.

The inductive core can be any shape that is useful for implantation into a patient's joint, including a solid cylindrical member, cylindrical member having hollow cavities, a tube, a flat sheet rolled into a tube so as to define a hollow cavity, liquid, or an amorphous shape which conforms to that of the tissue gap.

The inductive core may incorporate several different materials in different phases. The inductive core may be made of a gel, porous or non-porous solid or liquid material or some combination of these. There may be a combination of several different materials, some of which may be designed to release chemicals, enzymes, hormones, cytokines, or growth factors to enhance the inductive qualities of the inductive core.

Alternatively, the inductive core and adhesive zone can form a single continuous zone, either before insertion into the intra-articular zone or after insertion. Preferably, the inductive core and the adhesive zone is a single zone.

The inductive core may be seeded with cells. Furthermore, the cells can genetically altered to express growth factors or other chemicals.

Growth Factors. The effects of several growth factors on cultures of ligament cells have been reported, such as platelet derived growth factor-AA (PDGP-AA), platelet derived growth factor-BB (PDGF-BB), platelet derived growth factor-AB (PDGF-AB), transforming growth factor beta (TGF-β), epidermal growth factor (EGF), acidic fibroblast growth factor (aFGF), basic fibroblast growth factor (bFGF), insulin-like growth factor-1 (IGF-1), interleukin-1-alpha (IL-1α), and insulin (see, DesRosiers et al., 14 J. Orthop. Res. 200-9 (1996); Schmidt et al., 13 J. Orthop. Res. 184-90 (1995); Spindler et al., 14 J. Orthop. Res. 542-6 (1996)).

Adhesive zone. As shown in FIG. 1, the adhesive zone maintains contact between the inductive core and the patient tissue to promote the migration of cells from tissue into the inductive core.

Many of the same materials used to make the inductive core can also be used to make the adhesive zone. The adhesive zone may be made of permanent or biodegradable materials such as polymers and copolymers. The adhesive zone can be composed, for example, of collagen fibers, collagen gel, foamed rubber, natural material, synthetic materials such as rubber, silicone and plastic, ground and compacted material, perforated material, or a compressible solid material.

The adhesive zone can also be any shape that is useful for implantation into a patient's joint.

Figure 2:
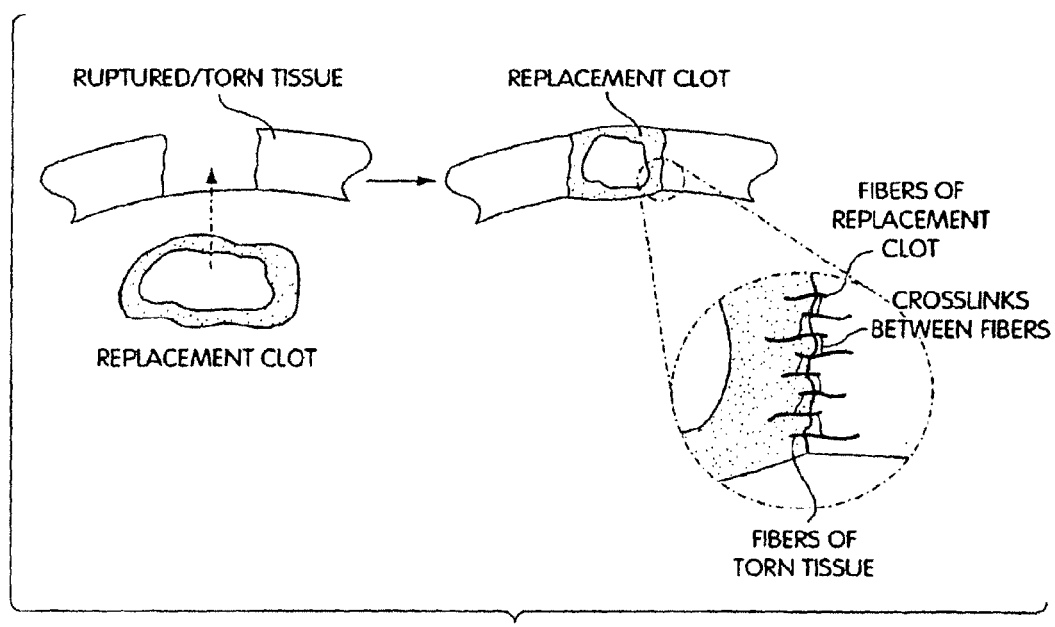
FIG. 2 is a schematic drawing of the bonding between fibers as an attachment mechanism.
Figure 3:
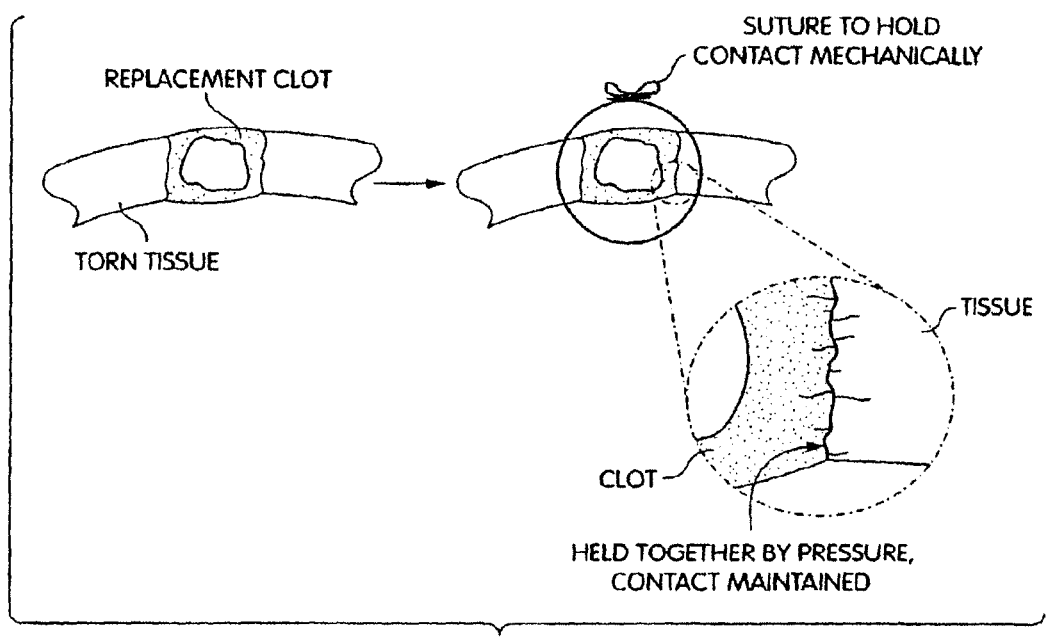
FIG. 3 is a schematic drawing of bonding between the inductive core and the tissue by maintaining mechanical contact.

The contact between the inductive core and the surrounding tissue can be accomplished by formation of chemical bonds between the material of the core and the tissue, or by bonding the material of the core to the adhesive zone combined with bonding the adhesive zone to the surrounding tissue (FIG. 2). Mechanical bonds can be formed that interlock the core with the tissue. Alternatively, pressure can be maintained on the core/tissue interface (FIG. 3).

Cross-linking. The formation or attachment of the adhesive zone can be enhanced by the use of other methods or agents, such as methods or agents that cross-link the adhesive phase together, or that cross-link the adhesive phase to the tissue, or both. The cross-linking may be by chemical means, such as glutaraldehyde or alcohol, or by physical means, such as heat, ultraviolet (UV) light, dehydrothermal treatment, or laser treatment. Physical cross-linking methods avoid the release of toxic by-products. Dehydrothermal cross-linking is achieved through drastic dehydration which forms interchain peptide bonds. Ultraviolet irradiation is believed to form cross-links between free radicals which are formed during irradiation.

The cross-linker may be added as an agent (such as a cross-linking protein) or performed in situ. The cross-linking may be between the collagen fibers or may be between other tissue proteins or glycosaminoglycans.

Cross-linking of collagen-based scaffolds affects the strength, biocompatibility, resorption rate, and antigenicity of these biomaterials (Torres, *Effects Of Modulus Of Elasticity Of Collagen Sponges On Their Cell-Mediated Contraction In Vitro* (M.S. Thesis Massachusetts Institute of Technology, 1998) (on file with the MIT Library); Troxel, *Delay of skin wound contraction by porous collagen-GAG matrices* (Ph.D. Thesis Massachusetts Institute of Technology, 1994) (on file with the MIT Library); Weadock et al., 29 J. Biomed. Mater. Res. 1373-1379 (1995)).

Cross-linking can be performed using chemicals, such as glutaraldehyde or alcohol, or physical methods, such as ultraviolet light or dehydrothermal treatment. The degree to which the properties of the scaffold are affected is dependent upon the method and degree of cross-linking. Cross-linking with glutaraldehyde has been widely used to alter the strength and degradation rate of collagen-based biomaterials scaffolds (Kato & Silver, 11 Biomaterials 169-175 (1990), Torres, *Effects Of Modulus Of Elasticity Of Collagen Sponges On Their Cell-Mediated Contraction In Vitro* (M.S. Thesis Massachusetts Institute of Technology, 1998) (on file with the MIT Library); Troxel, *Delay Of Skin Wound Contraction By Porous Collagen-GAG Matrices* (Ph.D. Thesis Massachusetts Institute of Technology, 1994) (on file with the MIT Library), and glutaraldehyde-cross-linked collagen products are commercially available for implant use in urologic and plastic surgery applications.

Use of physical cross-linking methods, including dehydrothermal (DHT) treatment and ultraviolet (UV) irradiation, is preferred to the use of glutaraldehyde for cross-linking. Cross-linking by DHT is achieved through drastic dehydration which forms interchain peptide bonds. UV irradiation is believed to form cross-links between free radicals which are formed during irradiation.

The nonlinear relationship between stress and strain for scaffolds cross-linked using glutaraldehyde, dehydrothermal treatment, ultraviolet light irradiation and ethanol treatment has demonstrated higher stiffness in the ethanol and ultraviolet groups, lowest stiffness in the dehydrothermal cross-linked groups, with the stiffness of the glutaraldehyde group in between (Torres, *Effects Of Modulus Of Elasticity Of Collagen Sponges On Their Cell-Mediated Contraction In Vitro* (M.S. Thesis Massachusetts Institute of Technology, 1998) (on file with the MIT Library)). Torres seeded collagen-based scaffolds with calf tenocytes and demonstrated a statistically significant increased rate of calf tenocyte cell proliferation in the glutaraldehyde and ethanol cross-linked scaffolds when compared with the dehydrothermal cross-linked group at 14 and 21 days post-seeding. Additional length of cross-linking in glutaraldehyde lead to increasing stiffness of the collagen scaffold, with values approaching that seen in the ultraviolet and ethanol groups. The ultraviolet cross-linked group demonstrated a statistically significant increase over the dehydrothermal group at 21 days, but not at 14 days post-seeding. This result suggests an influence of cross-linking method with fibroblast proliferation within the collagen-based scaffold.

Method of use. The methods of the invention may be used to treat injuries to the anterior cruciate ligament, the meniscus, labrum, cartilage, and other tissues exposed to synovial fluid after injury.

The intra-articular scaffold is designed for use with arthroscopic equipment. The scaffold is compressible to allow introduction through arthroscopic portals and equipment. The scaffold can also be pre-treated in antibiotic solution prior to implantation.

For methods involving a collagen-based scaffold, the affected extremity is prepared and draped in the standard sterile fashion. A tourniquet may be used if indicated. Standard arthroscopy equipment may be used. After diagnostic arthroscopy is performed, and the intra-articular lesion identified and defined, the tissue ends are pretreated, either mechanically or chemically, and the scaffold introduced into the tissue defect. The scaffold is then bonded to the surrounding tissue by creating chemical or mechanical bonds between the tissue proteins and the scaffold adhesive zone. This can be done by the addition of a chemical agent or a physical agent such ultraviolet light, a laser, or heat. The scaffold may be reinforced by placement of sutures or clips. The arthroscopic portals can be closed and a sterile dressing placed. The postoperative rehabilitation is dependent on the joint affected, the type and size of lesion treated, and the tissue involved.

For methods involving the meniscal glue or tissue-adhesive composition, a diagnostic arthroscopy is performed and the lesion defined. The knee may be drained of arthroscopic fluid and the glue inserted into the tear under wet or dry conditions, depending on the composition of the glue. The glue is bonded to the surrounding injured tissue and, when the desired bonding has been achieved, the knee is refilled with arthroscopic fluid and irrigated. The arthroscopic portals are closed and a sterile dressing applied. The patient is kept in a hinged knee brace post-operatively, with the degree of flexion allowed dependent on the location and size of the meniscal tear.

The details of one or more embodiments of the invention have been set forth in the accompanying description above. Although any methods and materials similar or equivalent to those described herein can be used in the practice or testing of the present invention, the preferred methods and materials have been described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented to more fully illustrate the preferred embodiments of the invention. These EXAMPLES should in no way be construed as limiting the scope of the invention, as defined only by the appended claims.

EXAMPLE 1

Fibroblast Distribution in the Anteromedial Bundle of the Human Anterior Cruciate Ligament The purpose of this EXAMPLE is to confirm the presence of cells expressing a contractile actin isoform alpha-smooth muscle actin ($\alpha$-sm; SMA), in the intact human anterior cruciate ligament, as shown by Murray & Spector, 17 (1) J. Orthop. Res. 18-27 (1999). Actin is a major cytoskeletal protein associated with cell motility, secretion, phagocytosis, and cytokinesis. Actin is expressed in mammals as six isoforms which are coded by different genes and differ in their amino acid sequence. Two of the isoforms ($\beta$ and $\gamma$) are found in practically all cells, while the other four ($\alpha$'s) are thought to represent differentiation markers of muscle cells. The $\alpha$-sm actin isoform is associated with the contractile phase of healing in several connective tissues, including dermis, cornea, tendon and medial collateral ligament. This isoform has also been associated with cell migration by Yamanaka & Rennard, 93 (4) Clin. Sci. 355-62 (1997).

The anterior cruciate ligament is a complex tissue composed of structural proteins, proteoglycans, and cells. The histology of the human anterior cruciate ligament is characterized by the specific distribution and density of the fibroblast phenotype as well as by the unique organization of the structural proteins. Three histologically different zones were found to be present along the anteromedial bundle from the femoral to the tibial attachment. Two of the zones (the fusiform and ovoid) were located in the proximal ⅓ of the bundle. The third zone (the spheroid) occupied the distal ⅓ of the bundle fascicles.

The fusiform cell zone had a high number density of longitudinally oriented cells with a fusiform-shaped nucleus, longitudinal blood vessels, and high crimp length. The cytoplasm of the cells in the fusiform zone were intimately attached to the extracellular collagen and followed the crimp waveform of the fibers. Fusiform cells stained positively for the $\alpha$-sm actin isoform in the fusiform zone, particularly at areas of crimp disruption.

The ovoid cell zone had a high number density of cells with an ovoid-shaped nucleus, longitudinal vessels, and a high crimp length. Ovoid cells stained positively for the $\alpha$-sm actin isoform in the ovoid cell zone.

The spheroid cell zone had a low density of spheroid cells, few blood vessels, and short crimp length. Cells were found within and among fascicles, as well as within lacunae. In selected areas, as many as 50% of the cells in this region stained positively for the $\alpha$-sm actin isoform. These findings demonstrated the uniformity of cell number density and morphology in the distal $\beta$ of the anteromedial bundle of the human anterior cruciate ligament, and thus a region for transection which would provide the most consistent starting cell density and nuclear morphology.

In summary, cells expressing the $\alpha$-sm actin isoform are present in the intact human anterior cruciate ligament, in cells with various morphologies, and predominantly in cells located at areas of crimp disruption.

The presence of $\alpha$-sm actin positive, potentially contractile, cells in the ruptured human anterior cruciate ligament may provide one possible explanation for the retraction of ligament remnants seen after complete rupture. Down-regulation of the myofibroblast phenotype may be useful in preventing premature ligament retraction, while up-regulation may be useful in self-tensioning of the healed ligament during the remodeling phase. Quantifying the degree of expression of the contractile actin and the effect of scaffold cross-linking and growth factors on this expression is a first step towards understanding possible regulation mechanisms.

EXAMPLE 2

Fibroblast Migration into the Anteromedial Bundle of the Human Anterior Cruciate Ligament In Vitro The purpose of this EXAMPLE was to confirm that human ligament fibroblasts can migrate into collagen-glycosaminoglycan copolymers in vitro.

Methods. Fifteen intact anterior cruciate ligaments were obtained from total knee arthroplasty patients, ages 54 to 82 years. Four of the ligaments were used solely for histology and immunohistochemistry. The remaining ligaments were sectioned into fascicles that were divided transversely in the midsubstance to make explants. The highly porous collagen-glycosaminoglycan matrix, composed of type 1 bovine hide collagen and chondroitin-6-sulfate, was prepared by freeze-drying the collagen-glycosaminoglycan dispension as described by Murray & Spector, in $45^{th}$ Annual Meeting, Orthopaedic Research Society, Anaheim, Calif. (1999). The average pore size of the collagen-glycosaminoglycan scaffold was 100 μm. Sample of the collagen-glycosaminoglycan matrix was sandwiched between 2 explants and the construct was stabilized by suturing the explants to silicone tubing (4 mm i.d.). The constructs were cultured in media containing Dulbecco's DMEM/F12 with 10% fetal bovine serum, 2% penicillin streptomycin, 1% amphotericin B, 1% L-glutamine and 2% ascorbic acid. Samples were fixed in formalin after one to six weeks, embedded in paraffin, sectioned, and stained with hematoxylin and eosin. Immunohistochemistry using monoclonal antibodies to detect $\alpha$-sm actin was also performed. Cell counts were taken at the edge of the scaffold for a cell density measure and the furthest distance traveled from the tissue/scaffold interface recorded for each sample.

Results. After 1 week in culture, fibroblasts in the explants began to display changes in morphology, with cells in the periphery becoming rounder. No cells were seen in the collagen-glycosaminoglycan scaffold. By 2 weeks, disruption of the ligament architecture at the edges of the fascicle could be observed, along with an increase in cell density at the periphery of the explants. In 2 of the 6 samples for this time period, cells had migrated into the collagen-glycosaminoglycan scaffold. By 4 weeks, further disruption of the normal ligament architecture was noted, as well as additional increases in cell density at the periphery of the explant. Four of the 6 samples for this time period showed migration of the fibroblasts into the scaffold to a distance of 0.1 to 2 mm. The 2 remaining samples were from ligaments which had displayed migration into the scaffold at 2 and 3 weeks. In these samples, the matrix had contracted and been resorted to the point that no material was retrievable. At 5 and 6 weeks, scaffolds that had not yet significantly contracted demonstrated increasing cell density. There did not appear to be a correlation between migration kinetics and patient age.

Anterior cruciate ligament tissue examined immediately after the retrieval demonstrated wide variability in the percentage of cells which stained positive for $\alpha$-sm actin. In general, a greater percentage of such cells were found in the midsubstance of the fascicles. With time in culture, the explanted tissue gradually developed a higher percentage of positive cells at the periphery of the explant. The areas displaying the greatest number of positive cells appeared to correspond to the areas of disrupted ligament architecture. All cells that migrated into the collagen-glycosaminoglycan scaffold stained positive for $\alpha$-sm actin.

Discussion. This EXAMPLE shows the potential for human anterior cruciate ligament fibroblasts to migrate from their native extracellular matrix into collagen-glycosaminoglycan scaffolds that may ultimately be used as implants to facilitate ligament regeneration.

EXAMPLE 3

The Migration of Human Anterior Cruciate Ligament Fibroblasts Into Porous Collagen-Gag Matrices In Vitro This EXAMPLE was designed to determine if fibroblasts intrinsic to the human anterior cruciate ligament were capable of migrating from their native extracellular matrix onto an adjacent provisional scaffold in vitro. Another objective was to determine whether any of the cells which successfully migrated into the scaffold expressed the contractile actin isoform, α-sm actin, associated with wound contraction in other tissues. This EXAMPLE demonstrates that the cells intrinsic to the human anterior cruciate ligament are able to migrate into a collagen-glycosaminoglycan scaffold, bridging a gap between transected fascicles in vitro.

Explants of human anterior cruciate ligament are useful as the source of cells for migration testing, because the explants provide a known distribution of cells within an extracellular matrix carrier. Thus, any cells which are found in the adjacent collagen-glycosaminoglycan scaffold during the test must have migrated there, as fluid flow during cell seeding is avoided. This method also avoids possible modification of cell phenotype which may occur during cell isolation, expansion in 2-D culture, and seeding of scaffolds.

As a result of cell migration and proliferation, areas in the scaffold contained cell number densities similar to that seen in the human anterior cruciate ligament in vivo. No extracellular matrix or tissue deposition was seen in the gap between directly apposed transected ends of the anterior cruciate ligament explant cultured without an interposed collagen-glycosaminoglycan scaffold. Both the fascicle-collagen-glycosaminoglycan-fascicle constructs and the fascicle-fascicle explants displayed minimal adherence after 6 weeks in culture. Any disruption in the contact area between explant and scaffold, even as small a gap as 50 microns, was noted to prevent cell migration from the explant to the collagen-glycosaminoglycan scaffold at the area of loss of contact. All cells which migrated into the collagen-glycosaminoglycan scaffold at early time periods were found to express the α-sm actin isoform.

This EXAMPLE demonstrates that cells that migrate into and proliferate within the collagen-glycosaminoglycan matrix have contractile potential as reflected in their expression of the α-sm actin isoform. Moreover, this EXAMPLE demonstrates the potential of cells intrinsic to the human anterior cruciate ligament to migrate into collagen-glycosaminoglycan scaffolds.

Figure 4:
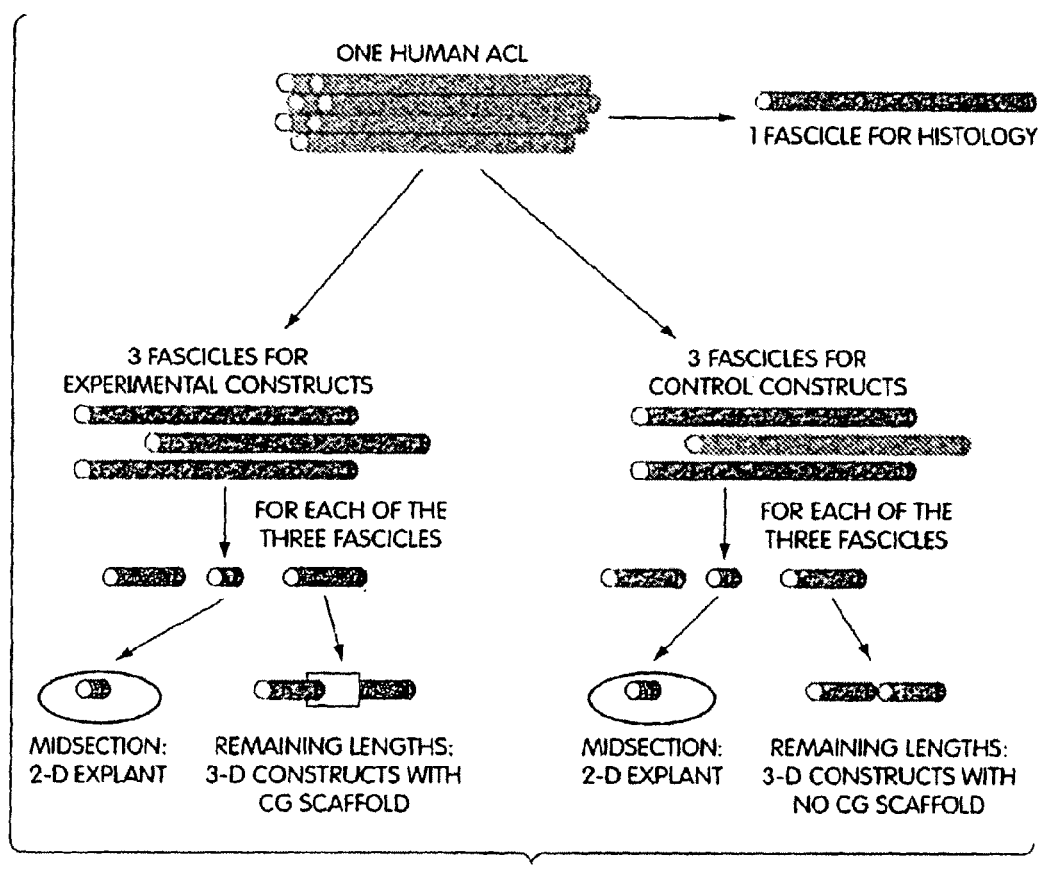
FIG. 4 is a schematic of tissue allocation for explants for 2-dimensional (2-D) and 3-dimensional (3-D) migration constructs.

Methods. Six intact anterior cruciate ligaments were obtained from 6 women undergoing total knee arthroplasty, ages 40 to 78, with a mean age of 58 years. Seven fascicles between 1 and 5 mm in diameter were dissected from each ligament. One fascicle from each ligament was allocated for histology. The remaining 36 fascicles were transected in the middle α and a 1 mm thick section of the midsubstance was taken from the division site for 2-D explant culture (FIG. 4). The two remaining segments of each fascicle were then used to form the 3-D test (fascicle-scaffold-fascicle) and control (fascicle-fascicle) constructs (see, below). The middle third of the fascicle was used as the area of investigation because previous histologic evaluation of the anterior cruciate ligament fascicles revealed that this region had the most consistent cell morphology and density.

Explant Culture on a 2-D Surface. The 36 1-mm thick samples from the midsection of all fascicles were cultured in 35 mm diameter dishes (Corning #430343, 6 well plates, Cambridge, Mass.) containing 1 cc of media comprised of Dulbecco's DMEM/F12 with 10% fetal bovine serum, 2% penicillin streptomycin, 1% amphotericin B, 1% L-glutamine and 2% ascorbic acid. One of the transversely cut surfaces was placed against the culture dish. Because of the variation in fascicular diameter, the explant area in contact with the culture dish ranged from 1 $mm^2$ to 20 $mm^2$. Media were changed 3× a week. Outgrowth from the explant biopsies was recorded every 3 days as the surface area covered by contiguous fibroblasts. The area of outgrowth was measured using an inverted microscope and a transparent grid sheet. The number of squares covered by the contiguous cells was counted and the corresponding area determined. The effective radius of outgrowth was calculated by assuming a circular area of contiguous cells. The rate of outgrowth was then calculated by plotting the average effective radius of outgrowth as a function of time from the first observed outgrowth, and the slope from the linear regression analysis was used as the rate of outgrowth. Twenty-four of the 33 samples demonstrated contiguous cell growth for at least 2 consecutive time periods prior to termination of the culture and were included in the calculation of the average rate. All explanted tissue and fibroblasts on the culture wells were fixed in formalin after 4 weeks in culture.

Collagen-Glycosaminoglycan Scaffold. The porous collagen-glycosaminoglycan scaffold used in this EXAMPLE has been used successfully in regeneration of dermis (Yannas, in *Collagen Vol III: Biotechnology*, Nimni, ed., p. 87-115 (CRC Press, Boca Raton, Fla., 1989)) and peripheral nerve (Chamberlain, *Long Term Functional And Morphological Evaluation Of Peripheral Nerves Regenerated Through Degradable Collagen Implants* (M.S. Thesis Massachusetts Institute of Technology, 1998) (on file with the MIT Library)). The 3-D culture substrate was a highly porous collagen-glycosaminoglycan matrix, composed of type I bovine tendon collagen (Integra Life Sciences, Inc., Plainsboro, N.J.) and chondroitin-6-sulfate (Sigma Chemical, St. Louis, Mo.). The scaffold was prepared by freeze-drying the collagen-glycosaminoglycan dispersion under specific freezing conditions described by Yannas et al, 8 Trans. Soc. Biomater. 146 (1985) to form a tube with pore channels preferentially oriented longitudinally. The average pore size of the collagen-glycosaminoglycan scaffold manufactured in this manner has previously been reported by Louie, *Effect Of A Porous Collagen-Glycosaminoglycan Copolymer On Early Tendon Healing In A Novel Animal Model* (Ph.D. Thesis Massachusetts Institute of Technology, 1997) (on file with the MIT Library) as 100 μm.

Fascicular Collagen-Glycosaminoglycan Scaffold Constructs. The 6 fascicles from each of the 6 patients were divided into test (fascicle-scaffold-fascicle) and control (fascicle-fascicle) groups. This yielded one test and one control construct per patient for examination after 2 weeks, 4 weeks, and 6 weeks in culture, providing 6 test and 6 control constructs at each of the 3 time points.

Figure 5:
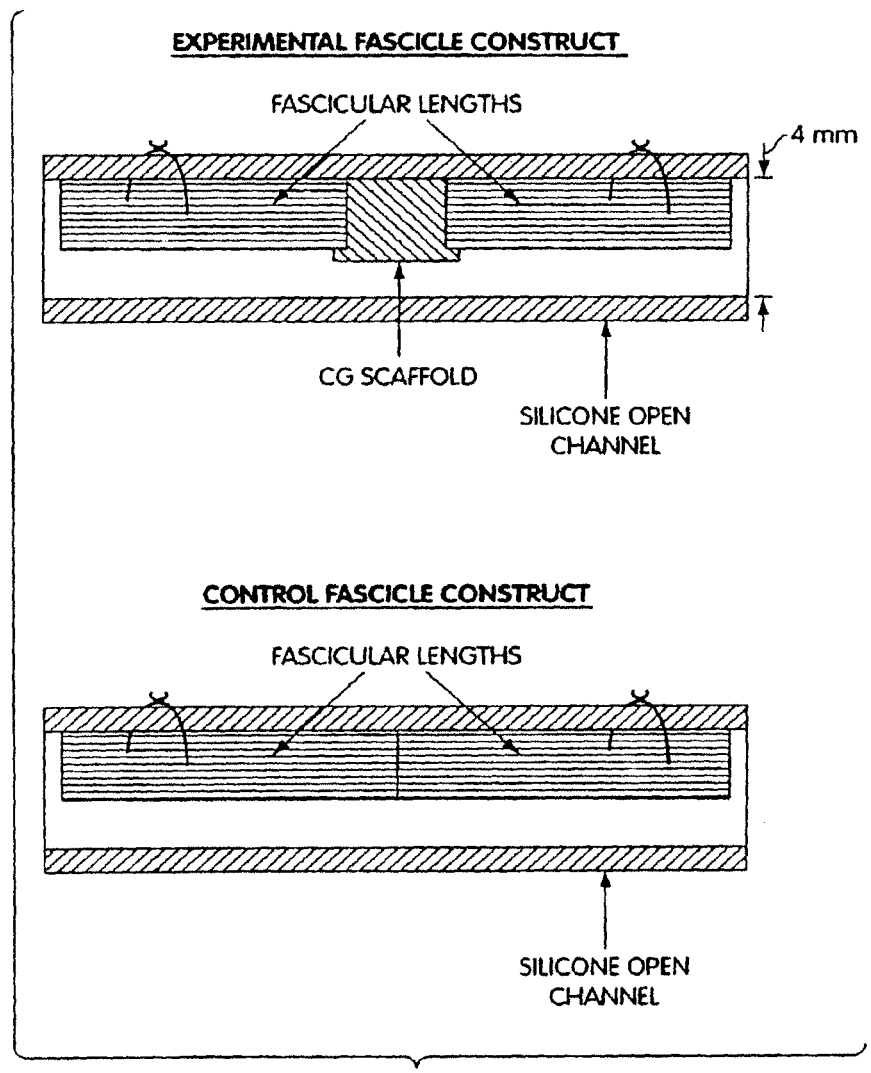
FIG. 5 is a schematic of test and control 3-dimensional (3-D) constructs viewed from the top.

The 18 test constructs were made by suturing each of the 2 fascicle lengths to an open channel cut from silicon tubing such that a 3-mm gap separated the transected ends. A 5-mm length of collagen-glycosaminoglycan scaffold (see, below) was compressed into the gap (FIG. 5). The 18 control constructs were made by reapposing the transected ends and then securing the fascicles to similar open channels (FIG. 5). All of the 36 fascicle constructs were cultured in media containing Dulbecco's DMEMI F12 with 10% fetal bovine serum, 2% penicillin streptomycin, 1% amphotericin B, 1% L-glutamine and 2% ascorbic acid. Media were changed 3× a week.

Histologic Evaluation. One test and one control construct from each patient (n=6) were fixed in formalin after 2, 4 and 6 weeks in culture. After formalin fixation for at least 72 hr, samples were dehydrated through graded solutions of ethanol and embedded in paraffin. Microtomed sections were cut at 6 μm thickness. Hematoxylin and eosin staining and immunohistochemical staining for α-sm actin (see, below) were performed for each construct. Sections were examined using a Vanox-T AH-2 microscope (Olympus, Tokyo, Japan) with normal and polarized light.

Figure 19:
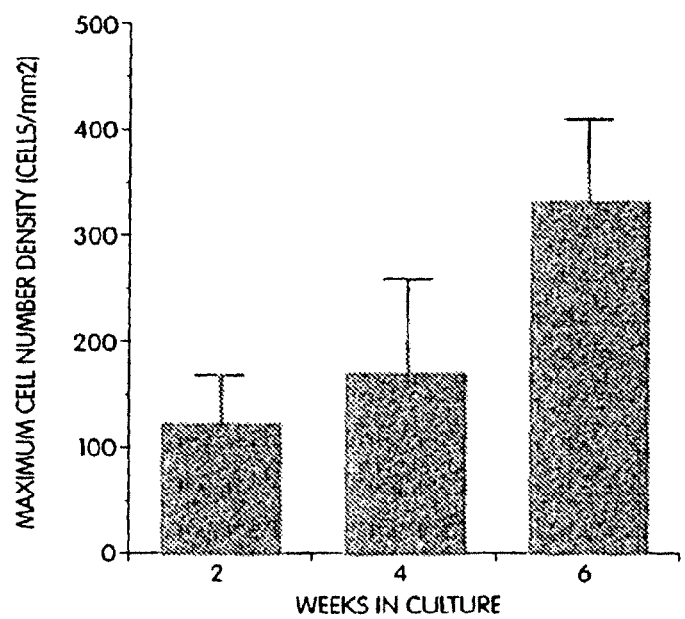
FIG. 19 is a histogram showing maximum cell number density in the collagen-glycosaminoglycan scaffold as a function of time in culture.

For each construct, eleven points along the length were counted for cell number density. For each region, 3 areas of 250×400 µm were analyzed. Within each of the two fascicles, cell number density was counted at the edge of the fascicle, 1 mm from the edge and 2 mm into the bulk of the fascicle. The two values for each position (one in each fascicle) were averaged to obtain the values for the construct (n=6). Within the collagen-glycosaminoglycan scaffold, cell number density was counted at each edge in contact with the fascicle, as well as 1 and 2 mm from each edge of the scaffold. The 2 values for each position (from each contact edge) were averaged to obtain the values for the construct (n=6). The average value for cell number at each position was multiplied by 10 to obtain the number of cells/mm$^2$ (see, FIG. 19). The fascicular tissue and collagen-glycosaminoglycan scaffolding were examined using polarized light to determine the degree of crimp and collagen alignment.

Immunohistochemistry. The expression of α-sm actin was determined using a monoclonal antibody. For the 3-D culture specimens, deparaffinized, hydrated slides were digested with 0.1% trypsin (Sigma Chemical, St. Louis, Mo., USA) for 20 minutes (min). Endogenous peroxidase was quenched with 3% hydrogen peroxide for 5 min. Nonspecific sites were blocked using 20% goat serum for 30 min. The sections were then incubated with the mouse anti-α-sm actin monoclonal antibody (Sigma Chemical, St. Louis, Mo., USA) for 1 hr at room temperature. Negative controls were incubated with mouse serum diluted to an identical protein content. The sections were then incubated with biotinylated goat anti-mouse IgG secondary antibody for 30 min followed by 30 min of incubation with affinity purified avidin. The labeling was developed using the AEC chromagen kit (Sigma Chemical, St. Louis, Mo.) for ten min. Counterstaining with Mayer's hematoxylin for 20 min was followed by a 20 min tap water wash and coverslipping with warmed glycerol gelatin.

Histology of the Ligament Fascicles. The histology of the fascicles from each of the 6 patients was as follows: The proximal ⅓ was populated predominantly by fusiform and ovoid cells in relatively high density, and the distal ⅔ was populated by a lower density of spheroid cells. The level of transection used to produce the fascicle constructs was in the spheroid cell region, with similar cell morphologies and an average cell number density of 498±34 cells/mm$^2$ (n=6). α-sm actin immunohistochemistry of the transected region showed positive staining in 8.3±3.0% of fibroblasts not associated with blood vessels.

Changes in the Fascicular Tissue with Time in Culture. With time in culture, changes in the cell distribution and extracellular matrix organization of the anterior cruciate ligament tissue in the 36 test and control fascicular constructs were observed. Fusiform, ovoid and spheroid nuclear cell morphologies could be observed in the bulk of the cultured fascicles. Time in culture was noted to have a statistically significant effect on the cell number density at each location (i.e., at the edge and at 1 and 2 mm into the bulk of the fascicle; one-way ANOVA, p<0.001). The number density of cells at the edge of the explants decreased to 120±29 cells/mm$^2$ at 2 weeks and to 101±28 cells/mm$^2$ at six weeks, both of which were different from the cell number density at retrieval, 498±34 cells/mm$^2$, as noted above (paired t-test, p<0.001). The number of cells within the bulk of the fascicle decreased as well, to 58±21 cells/mm$^2$ at 2 weeks and 19±20 cells/mm$^2$ at six weeks, again, both densities were significantly different from that at retrieval (paired t-test, p<0.0001).

At 2 and 4 weeks, the percentage of cells staining positive for α-sm actin increased to 30±8% at the edge of the fascicles compared with the 8.3±3.0% before culture (paired t-test, p=0.06); none of the cells 2 mm into the bulk of the fascicle stained positive for α-sm actin. The percentage of cells expressing the α-sm actin isoform at the edge of the fascicle decreased with time in culture to 6±4% at week 6, a value not statistically significantly different from that before culture (paired t-test, p>0.30). The percentage of cells staining positive for α-sm actin remained low in the bulk of the fascicle, with 2±2% of cells staining positive at 6 weeks.

The extracellular matrix of the explant exhibited disruption of the structural organization with time in culture. Loss of crimp and fascicular alignment was severe enough at the 2 week time point to prohibit any measure of crimp length or degree of organization. The near uniaxial alignment and crimp of the collagen fibers was lost and the tissue assumed a looser appearance.

Figure 6:
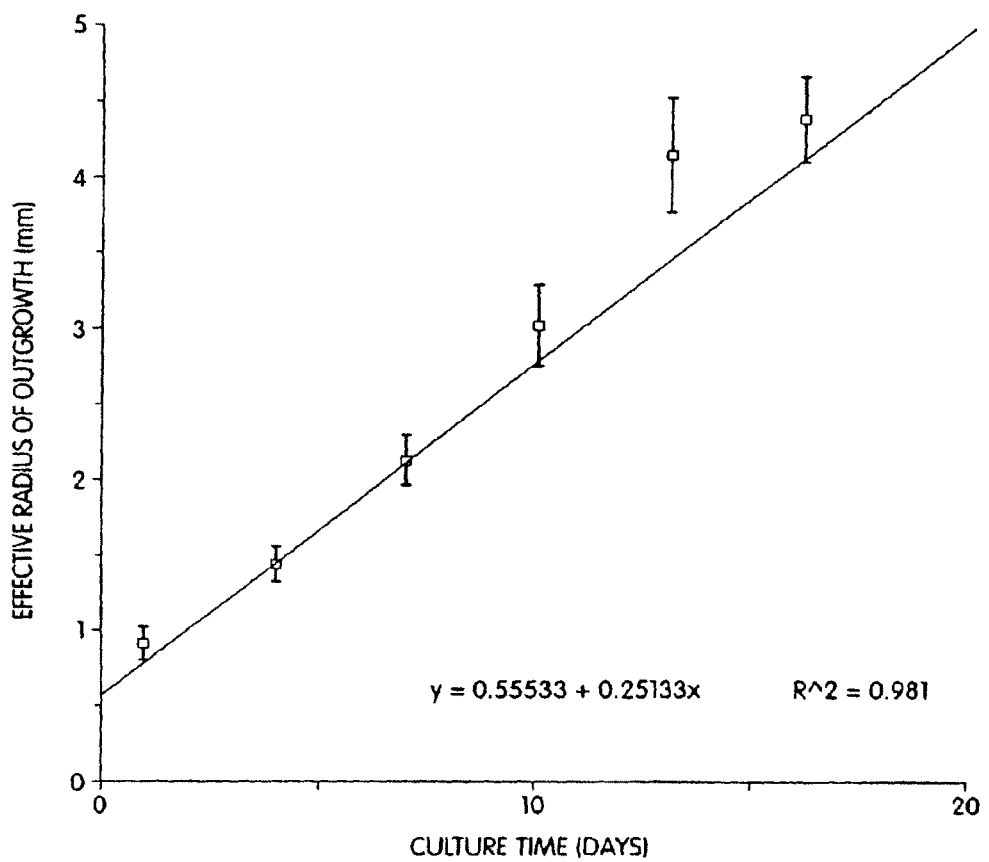
FIG. 6 is a graph depicting the effective radius of outgrowth as a function of time from initial observed outgrowth for human anterior cruciate ligament (ACL) explants (n=24, values are mean±SEM).

2-D Culture Outgrowth. The outgrowth of cells onto the 2-D culture dishes was observed to occur as early as 6 days and as late as 19 days, with outgrowth first detected after an average of 10±3 days. The time of onset or rate of outgrowth was not found to correlate with explant size. Linear regression analysis of the plot of effective outgrowth radius versus time for all explants that demonstrated contiguous outgrowth had a coefficient of determination of 0.98. The average rate of outgrowth, represented by the slope of this plot, was 0.25 mm/day (FIG. 6).

3-D Culture Outgrowth. The reapposed tissue ends of the 18 control (fascicle-fascicle) constructs had no adherence to each other even after six weeks in culture; as soon as the retaining sutures were removed, the fascicle ends separated. Histologically, no matrix deposition was seen between or adjacent to the transected fascicle ends, although increases in cell density at the periphery of the fascicles were noted.

Figure 7:
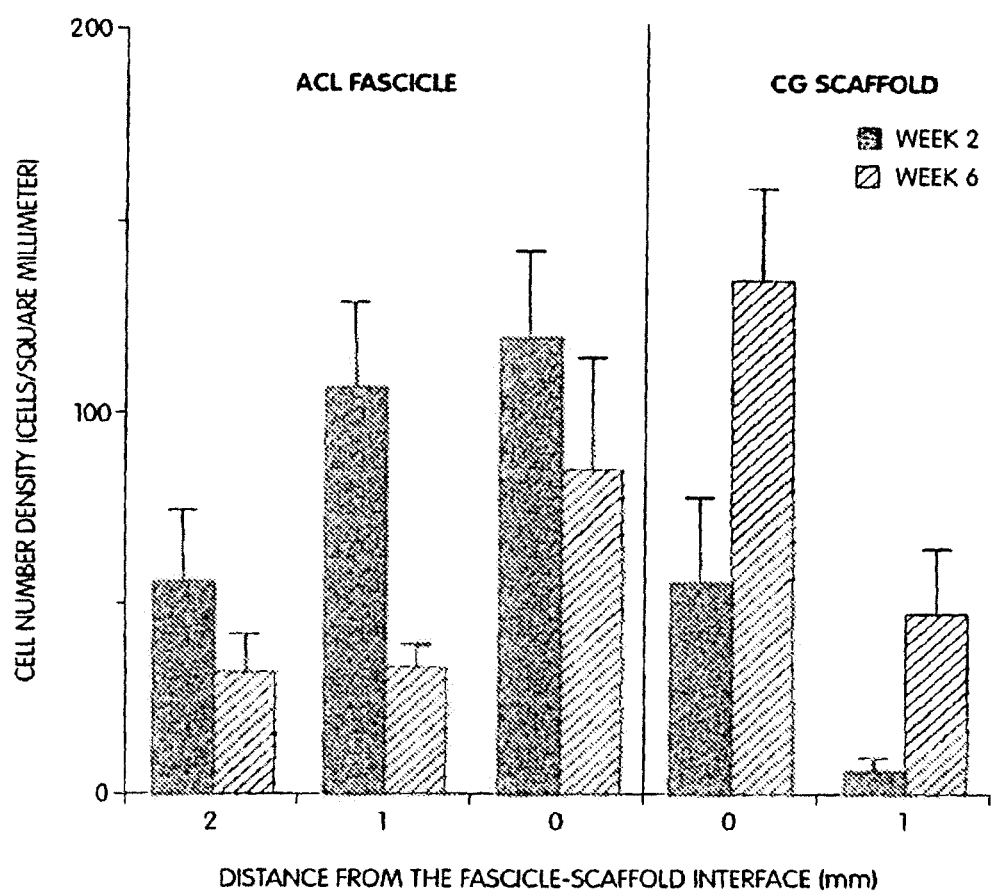
FIG. 7 is a histogram demonstrating the changes in cell density in the fascicle-collagen-glycosaminoglycan (CG) scaffold construct as a function of time in culture (values are the mean±SEM).
Figure 8:
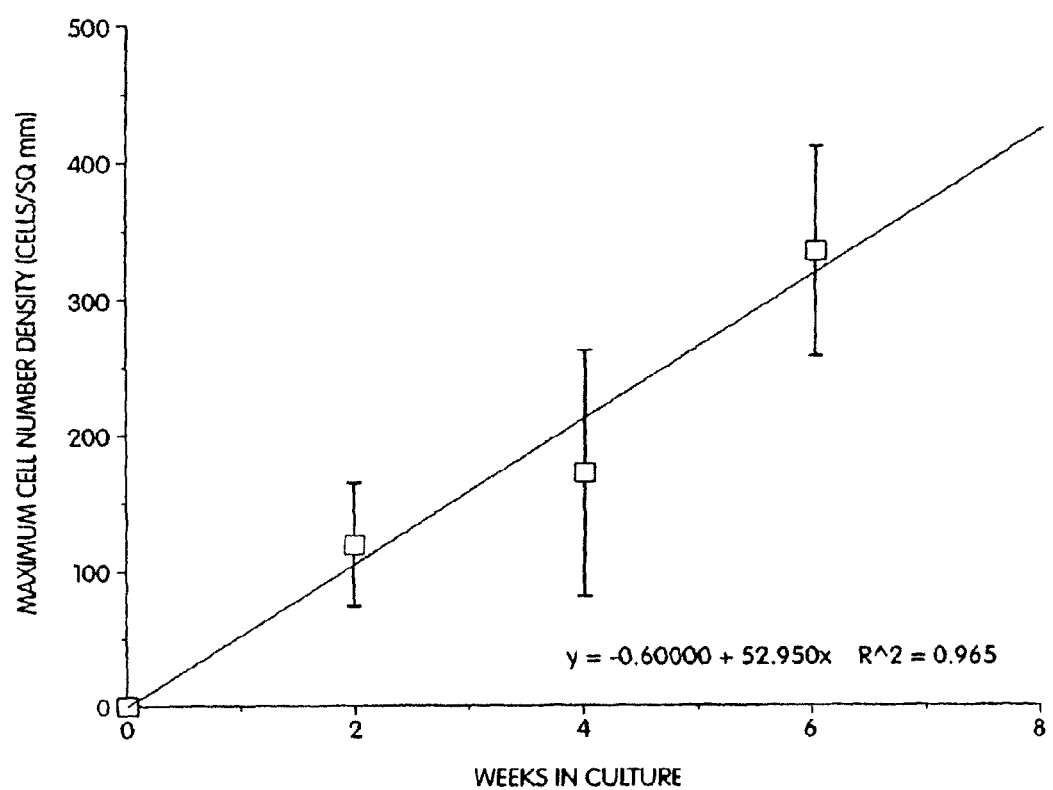
FIG. 8 is a histogram of the maximum cell number density in the collagen-glycosaminoglycan scaffold as a function of weeks in culture (values are mean±SEM).

In the constructs with interposed collagen-glycosaminoglycan scaffolding, fibroblasts were noted to migrate from the human anterior cruciate ligament fascicles into the scaffolds at the earliest time point (2 weeks). Migration into the scaffold was seen in 5 of 6 constructs at 2 weeks, 5 of 6 constructs at 4 weeks, and in all 5 of the 6-week constructs. While the average cell number density in the fascicle decreased with time, the average cell number density in the scaffold increased with time in culture (FIG. 7). Initially, cells were noted predominantly at the edge of the scaffold. With time, the average cell number density at the edge of the scaffold increased from 57±22 cells/mm$^2$ at 2 weeks and to 120±41 cells/mm$^2$ at six weeks. While this was a 2-fold increase, it was not found to be statistically significant (p=0.15) owing to the large coefficient of variation. The average cell number density 1 mm within the scaffold also increased from 6±2 cells/mm$^2$ at 2 weeks to 25±10 cells/mm$^2$ at 4 weeks and to 47±37 cells/mm$^2$ at 6 weeks. Again, owing to the large variation, these increases were not statistically significant (p=0.15), despite being increases of several-fold. While there was a consistent increase in the mean value of the cell number density with time at the various distances from the scaffold/fascicle interface, two way ANOVA showed no significant effect of time in culture on cell number density at each location (p=0.10), but did reveal a significant effect of location on cell number density (p<0.001). The maximum cell number density of fibroblasts in the scaffold increased with time from 123±45 cells/mm$^2$ at 2 weeks to 336±75 cells/mm$^2$ at six weeks, a difference which was statistically significant (Student t test, p=0.05). The relationship between maximum cell number density and time was well modeled by a linear regression, with a coefficient of determination of 0.96 (FIG. 8). Cells migrating into the collagen-glycosaminoglycan scaffold demonstrated all of the three previously described ligament fibroblast morphologies: (1) fusiform or spindle-shaped, (2) ovoid, and (3) spheroid. The average migration distance at the 2-week time period was 475 micrometers. At the 4-week time point, cells had migrated as far as 1.5 mm toward the center of the scaffold. In areas where a gap greater than 50 microns was present between the explant and collagen-glycosaminoglycan scaffold, no cell migration into the scaffold was seen.

All cells which migrated into the collagen-glycosaminoglycan sponge were found to be positive for α-sm actin at the 2-week period. These cells demonstrated both unipolar and bipolar staining with the chromagen appearing prominently in the cytoplasm on only one side or on both sides of the nucleus. The percentage of cells staining positive decreased with time, with the edge of the scaffold having only 66±9% of cells staining positive at the six-week time point, and the bulk of the scaffold containing 95±4% positively staining cells. Particularly, cells located in areas of high cell density were noted to no longer stain positive.

No remarkable degradation of the scaffold was found during the time course of the EXAMPLE, although the average pore diameter was noted qualitatively to decrease with time in culture.

Discussion. This EXAMPLE demonstrates that the cells intrinsic to the human anterior cruciate ligament were able to migrate into the gap between transected fascicles, eventually attaining selected areas with cell number densities similar to that seen in the human anterior cruciate ligament in vivo, if a provisional scaffold was provided. No extracellular matrix formation was seen between transected ends directly apposed without provisional scaffold. A gap between the explant and scaffold, even, as small as 50 μm, prevented cell migration to the scaffold at the site of loss of contact. Cells with all three previously described ligament fibroblast morphologies—fusiform, ovoid and spheroid-were noted to migrate into the scaffold. The cell density within the scaffold and maximum migration distance increased with time. These results show that cells intrinsic to the human anterior cruciate ligament are capable of migrating from their native extracellular matrix onto an adjacent collagen-glycosaminoglycan scaffold, if contact between the scaffold and explant is maintained, and do so in increasing numbers with time in culture.

Outgrowth from explants likely has two components—migration and proliferation. Previous results assumed minimal contribution from the proliferation component and reported outgrowth rates as migration rates (Geiger et al., 30 (3) Connect Tissue Res. 215-224 (1994)); the migration rate from rabbit anterior cruciate ligament explants was 0.48 mm/day. Using this same approach, the migration rate from human anterior cruciate ligament explants In this EXAMPLE is 0.25 mm/day. Previous studies did not report the cell number density of the explants (see also, Deie et al., 66 (1) Acta Orthop. Scand. 28-32 (1995)), so one cannot predict whether differences in reported results are due to species differences or to differences in the cell number density or phenotype.

This EXAMPLE demonstrates the chronology of expression of this phenotype in explants of ligament tissue in culture, as well as in cells which successfully migrate onto a 3-D scaffold. The percentage of α-sm actin-positive cells increases at the periphery of the explants from 8 to 30% after 2 weeks in culture. All ligament cells which migrated into the collagen-glycosaminoglycan matrix at 2 weeks contained α-sm actin, suggesting a role for this contractile actin isoform in cell migration. Moreover, most of these cells displayed a unipolar distribution of the contractile actin isoform. While the histological plane through the sample may have resulted in an asymmetric appearance of α-sm actin, it is unlikely that this was the sole cause of the appearance of unipolar staining. This unipolar distribution of the contractile protein may be associated with asymmetric contraction of the cytoplasm to facilitate cell movement.

Cells in the scaffold displayed bipolar, as well as unipolar, distribution of α-sm actin. Cells that attached to two walls of a pore of the scaffold often displayed the bipolar distribution. Bipolar expression of the contractile protein may lead to symmetric contraction of the cell cytoplasm and contracture of the matrix to which the cell is attached. This may have been responsible for the qualitative observation of a decrease in pore diameter of the collagen-glycosaminoglycan matrix with time in culture.

The anterior cruciate ligaments used in this EXAMPLE were all intact prior to resection, which suggests that the cells intrinsic to the ligament were able to maintain tissue structure.

This EXAMPLE shows the potential of human anterior cruciate ligament fibroblasts to migrate from their native extracellular matrix into collagen-glycosaminoglycan scaffolds that may ultimately be investigated as implants to facilitate ligament healing. The EXAMPLE allows for the analysis of the migration of fibroblasts out of human tissues directly onto a porous 3-D scaffold.

EXAMPLE 4

Scaffold Optimization for Healing of The Ruptured Human Anterior Cruciate Ligament The purpose of this EXAMPLE is to demonstrate the process of fibroblast-mediated tissue regeneration, to determine the effect of cross-linking of a collagen-based scaffold on (a) the rate of fibroblast migration; (b) the rate of fibroblast proliferation; (c) expression of a contractile actin; and (d) the rate of type I collagen synthesis by fibroblasts in the collagen-based scaffold. This EXAMPLE is also intended to determine the effect of addition of selected growth factors on these same outcome variables. The results of this EXAMPLE can be used to determine how specific alterations in scaffold cross-linking and the addition of specific growth factors alter the fibroinductive properties of a collagen-based scaffold. For the purposes of this EXAMPLE, the fibroinductive potential of the scaffold is defined as its ability to promote fibroblast infiltration, proliferation and type I collagen synthesis.

Two scientific rationales relate to the purposes listed above:

The method and degree of cross-linking alter the rate of fibroblast migration from an anterior cruciate ligament explant into a collagen-based scaffold as well as the rate of fibroblast proliferation, expression of a contractile actin, and type I collagen synthesis within the scaffold. The bases for these rationales are results which have demonstrated (a) alteration in fibroblast proliferation rates and expression of the contractile actin isoform after fibroblast seeding of cross-linked scaffolds; and (b) differences in rates of collagen synthesis by chondrocytes seeded into type I and type II collagen-based scaffolds. Solubilized fragments of collagen resulting from the degradation of the collagen-based scaffold may affect cell metabolism. These fragments may form at different rates for different cross-linking methods. Therefore, the fibroinductive properties of the collagen-based scaffold may be regulated by the choice of cross-linking method.

The addition of growth factors to the collagen-glycosaminoglycan scaffold alters (a) the rates of fibroblast migration from an anterior cruciate ligament explant to a collagen-based scaffold; (b) the rates of fibroblast proliferation; (c) the expression of a contractile actin; and (d) the type I collagen synthesis within the scaffold. The bases for this rationale are (a) the alteration in fibroblast migration rates onto 2-D surfaces, (b) synthesis of type I collagen in vitro when growth factors are added to the culture media, and (c) alterations in rates of incisional wound healing. The effects of 4 different growth factors and 4 collagen-based substrates on features associated with the repair processes in connective tissues which successfully heal are assayed for: (1) fibroblast migration; (2) proliferation; and (3) type I, II and III collagen synthesis. For the purposes of this EXAMPLE, these are referred to as fibroinductive properties.

Assay design. Explants from human anterior cruciate ligaments are placed into culture with a type I collagen-glycosaminoglycan scaffold in a construct (see, EXAMPLE 3). Migration rates of cells from the explant into the collagen-glycosaminoglycan scaffold are measured at 1, 2, and 4 weeks. Three constructs for each of the 4 types of cross-linking are required for each time point: (1) one explant/scaffold specimen for histology for the migration calculations and α-sm actin immunohistochemistry; (2) one specimen for the DNA assay for proliferation, and (3) a third specimen for SDS-PAGE analysis for type I collagen synthesis. One additional construct is fixed immediately for histology. Thus, 10 explant/scaffold constructs are used for each type of cross-linked scaffold or growth factor tested. The power calculation for sample size for the number of patients to include is based on detecting a 30% difference in the mean values of the outcome variables. Assuming a 20% standard deviation, a power of 0.80 ($\beta$=0.20), and a level of significance of $\alpha$=0.05, n=6 patients are required. For the cross-linking phase, human anterior cruciate ligament tissue are obtained from 6 patients and 10 explant/scaffold constructs made for each of the four types of cross-linked collagen (a total of 40 constructs per patient). For the growth factor phase, human anterior cruciate ligament tissue are obtained from 6 additional patients and 10 explant/scaffold constructs made for each of the four types of cross-linked collagen (a total of 40 constructs/patient).

Materials. The test constructs used in this EXAMPLE are explants of human tissue placed into culture directly onto 3-D fibrous collagen-glycosaminoglycan scaffolds (see, EXAMPLE 3). Human anterior cruciate ligament explants are obtained from patients undergoing total knee arthroplasty.

This construct allows for the analysis of the migration of fibroblasts out of human tissues directly onto a 3 D fibrous scaffold in a controlled in vitro environment and obviates several confounding factors, such as modulation of cell phenotype, which may occur during cell extraction or 2-D cell culture. This construct also allows for investigation of human fibroblasts and tissue, thus avoiding interspecies variability. Careful control of growth factor concentration and substrate selection are also possible with this in vitro model.

Preparation of the collagen-based scaffold. Type I collagen from bovine tendon is combined with chondroitin 6 sulfate from shark cartilage to form a co-precipitate slurry. The slurry is lyophilized in a freeze drier and minimally cross-linked with dehydrothermal treatment for 24 hr at 105° C. and 30 mtorr.

Cross-linking. All of the 3-D collagen-glycosaminoglycan scaffolds are minimally cross-linked using dehydrothermal treatment at 105° C. and 30 mtorr for 24 hr. Additional cross-linking is performed for the glutaraldehyde, ultraviolet, and ethanol groups. Glutaraldehyde cross-linking are performed by rehydrating the collagen-based scaffolds in acetic acid, treating in 0.25% glutaraldehyde for thirty minutes, rinsing and storing in a buffer solution. Ethanol cross-linking is performed by soaking the collagen scaffolds in 70% ethanol for 10 min, rinsing, and storing in buffer. Ultraviolet light cross-linking is performed by placing the scaffold 30 cm from an ultraviolet lamp rated at 5.3 W total output, 55.5 W/cm$^2$ at 1 m. The scaffolds is cross-linked for 12 hr, 6 hr on each side as previously described by Torres, *Effects Of Modulus Of Elasticity Of Collagen Sponges On Their Cell-Mediated Contraction In Vitro* (M.S. Thesis Massachusetts Institute of Technology, 1998) (on file with the MIT Library).

Addition of growth factors. The 4 growth factors are added to the cell culture media in concentrations based on those previously reported to be successful in the literature: (1) EGF at 10 ng/ml; (2) bFGF at 0.6 ng/ml; (3) TGF-β at 0.6 ng/ml; and (4) PDGF-AB at 10 ng/ml. Each growth factor is added individually to the control cell culture media containing DMEM-F12, 0.5% fetal bovine serum, 2% penicillin/streptomypin, 1% amphotericin B, 1% L-glutamine and 25 μg/ml of ascorbic acid.

Culture of explant/scaffold constructs. For the 3-D tests, explants are placed onto previously prepared 9 mm discs of collagen-glycosaminoglycan scaffold. Cell culture media is added to just cover the scaffold and changed every 3 days. Constructs are sacrificed at 1, 2, and 4 weeks.

Histology for analysis of cell migration. All specimens for light microscopy, including control fascicles and explants are fixed in 10% neutral buffered formalin for one week, embedded in paraffin and sectioned into 7 micrometer sections. Sections are taken perpendicular to the explant/scaffold interface to allow for migration measurements. Hematoxylin and eosin staining are performed to facilitate light microscopy examination of cell morphology in both explant and scaffold, maximum migration distance into the collagen-glycosaminoglycan scaffold and maximal number density of fibroblasts in the scaffold.

DNA Assay for Cell Proliferation. Specimens allocated for analysis of DNA content are fluorometrically. Specimens are rinsed in phosphate-buffered saline and the explant separated from the scaffold. The scaffold is stored at −70° C. The scaffold is digested in 1 ml of 0.5% papain/buffer solution in a 65° C. water bath. A 200 μl aliquot of the digest is combined with 40 μl of Hoechst dye no. 33258 and evaluated fluorometrically. The results are extrapolated from a standard curve using calf thymus DNA. For one run of the DNA assay, a standard curve based on a sample of human ligament cells are used to estimate the cell number from the DNA measurement. Negative control specimens consisting of the scaffold material alone are also assayed to assess background from the scaffold.

Additionally, a tritiated thymidine assay can be evaluated. Then, the specimens used for proliferation can be fixed and serially sectioned, with sections at regular intervals examined for cell number density. Maximum number density is recorded for each specimen type. Associated histology is used to estimate the percentage of dead cells.

SDS-PAGE analysis for the synthesis of type I collagen. Type I, II and III collagen production is measured using SDS-PAGE techniques. Specimens allocated for analysis of synthesis of type I collagen are cultured with tritiated proline for specific time periods after selected time in culture. Proline uptake studies is performed for scaffolds from each group. Biochemical determination of collagen types in both the scaffold and conditioned media is eluted with Triton and assayed by PAGE.

Immunohistochemistry. Immunohistochemistry is used to determine the distribution of cells producing the α-sm actin isoform in both the explanted tissue and the scaffold (see EXAMPLE 3). An additional benefits of this construct is that serial sections can be stained immunohistochemically for any protein for which an antibody is available. Therefore, additional investigation into the expression of the other subtypes of actin, or members of the integrin family during cellular migration may be performed, if time allows.

Transmission Electron Microscopy. Transmission electron microscopy is used to evaluate morphologic features of the migrating cells, as well changes in the extracellular matrix. Processing of specimens for transmission electron microscopy analysis begins with fixation for 6 hr in Karnovsky's fixative, followed by post-fixation with osmium tetraoxide, dehydration through graded alcohols, infiltration with graded propylene oxide/epon, embedding in epon, ultramicrotomy (70 angstroms) and post-staining with uranyl acetate. Characteristics of migrating cells to be examined in the TEM include characteristics of cytoplasm (such as the presence of abundant rough endoplasmic reticulum and presence of microfilaments consistent with α-sm actin) and characteristics of extracellular matrix (such as the presence of pericellular fine fibrils consistent with new collagen formation).

Analysis. The principal variables evaluated are the number of cells populating the scaffold, the production of type I, II and III collagen, and the expression of the contractile actin isoform. The control group are the minimally cross-linked scaffolds with no growth factor addition. Assuming a standard deviation of 30%, to detect a difference between groups of 30%, with an "α" of 0.05 and a "β" of 0.1 (i.e., a power of 90%) has a sample size of 13 for each group. Therefore, to investigate 4 growth factors at 4 time points uses 208 constructs each for the histology and TEM, DNA testing, and SDS-PAGE analysis, a total of 624 constructs. An identical number is required to investigate the 4 methods of cross-linking.

EXAMPLE 5

Migration of Cells from Ruptured Human Anterior Cruciate Ligament Explants into Collagen-Gag Matrices How does the cellular response to injury affect migration behavior? The objective of this EXAMPLE was to evaluate the migration of cells from explants from selected zones within ruptured human anterior cruciate ligaments into collagen-glycosaminoglycan matrices in vitro. The proliferation of cells in the matrices and their contractile behavior were also assessed.

Methods. Four ruptured human anterior cruciate ligaments were removed from patients undergoing reconstructive procedures. The ruptures occurred in the proximal third of the ligaments. One explant was prepared from each of three zones in the tibial remnant: the femoral, middle, and tibial zones. The explants were placed on top of 9-mm diameter collagen-glycosaminoglycan matrices and analyzed after 1, 2, 3, and 4 weeks (n=4).

The collagen-glycosaminoglycan matrix was prepared by freeze-drying a coprecipitate of type I bovine tendon collagen (Integra Life Science, Plainsboro, N.J.) and shark chondroitin 6-sulfate (Sigma Chem. Co., St. Louis, Mo.). The matrix was cross-linked for 24 hr. using a dehydrothermal treatment. The scaffolds had a pore diameter of approximately 90 μm.

The diameter of the sponges was measured with time in culture. Matrices without explants were cultured under the same conditions as controls. The cell density within the matrices was determined by dividing the number of cells evaluated histologically by the area of analysis, and immunohistochemistry using a monoclonal antibody was performed to determine the percentage of cells containing a contractile actin isoform, α-smooth muscle actin (α-sm). The results were compared with cells migrating from explants obtained from intact human anterior cruciate ligament specimens.

Figure 9:
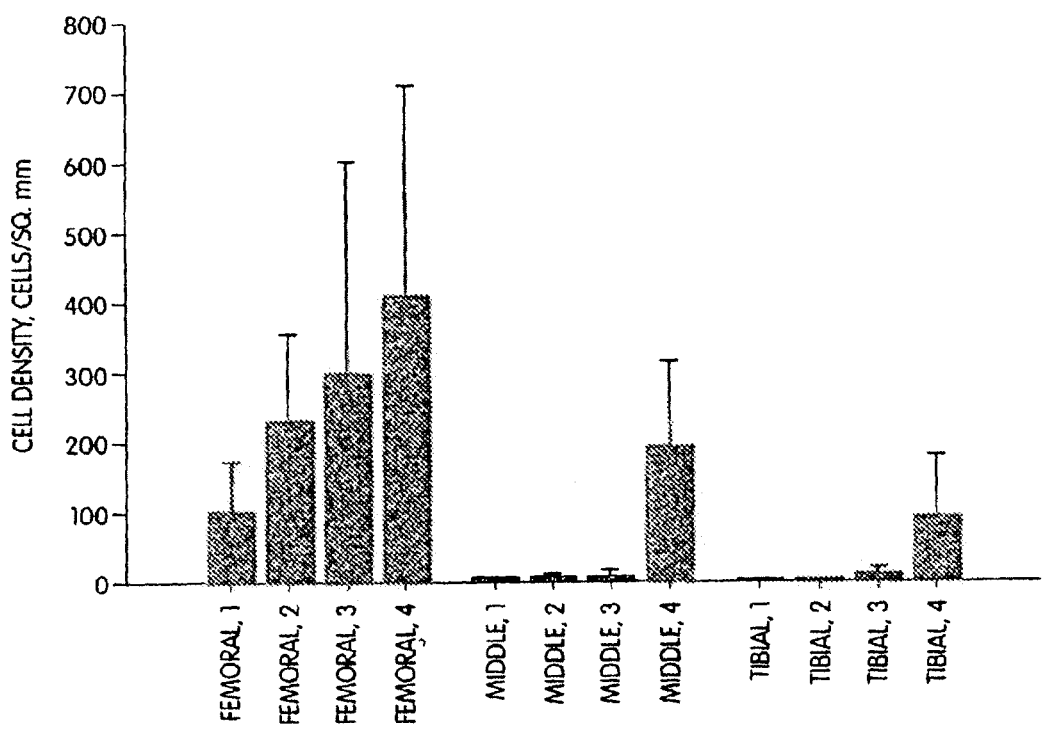
FIG. 9 is a histogram showing the cell densities in collagen-glycosaminoglycan (CG) matrices into which cells from explants from femoral, middle, and tibial zones of ruptured anterior cruciate ligaments migrated and proliferated after 1, 2, 3, and 4 weeks in culture. (Values are the mean±SEM).

Results. Cells from the explants migrated into, and proliferated within, the collagen-glycosaminoglycan matrices resulting in an increase in the cell density in the scaffolds with time (FIG. 9). Two-way ANOVA revealed a significant effect of the location from which the explant was taken on cell density (p=0.009), but not of time in culture (p=0.11). There was more active migration and prolferation of cells from the femoral zone of the ruptured anterior cruciate ligaments than from cells from the middle and tibial regions (FIG. 9). The cell density resulting from explants from the femoral zone of the ruptured anterior cruciate ligaments was greater than that from intact human anterior cruciate ligament explants after 2 (110±38 cells/mm$^2$; mean±SEM) and 4 weeks (170±71). Immunohistochemistry revealed the presence of α-sm in the ligament cells in the scaffolds. There was a significant decrease in the diameter of the matrices with time in culture to approximately 70% of the original diameter evidencing the contractile behavior of the α-sm-positive cells.

Discussion. The results of this EXAMPLE demonstrate that cells in the ruptured human anterior cruciate ligament, particularly in the proximal region near the rupture site, have the capability to migrate into, and proliferate within, collagen-glycosaminoglycan scaffolds that could ultimately be used as implants to facilitate regeneration of the tissue. Moreover, cells growing out from the ruptured anterior cruciate ligament express the gene for a contractile actin isoform. The expression of α-sm in other connective tissue cells contributes to healing through wound closure. This work provides guidance for strategies for the tissue engineering of the anterior cruciate ligament in vivo.

EXAMPLE 6

Changes in Human ACL Migration Potential After Ligament Rupture

The objective of this EXAMPLE was to determine whether anterior cruciate ligament cells would continue to migrate after complete rupture, and to determine what effect the location of cells in the ruptured human anterior cruciate ligament had on their ability to migrate.

Methods. Ruptured (n=6) anterior cruciate ligaments were retrieved from patients undergoing anterior cruciate ligament reconstruction. Explants were taken from the rupture site and placed in culture with ah collagen-based scaffold. Explants from ruptured ligaments far from the site of rupture (n=6) and from intact anterior cruciate ligaments (n=10) were also place in culture with the scaffolds and analyzed as control groups. Scaffolds were analyzed after 2, 3, and 4 weeks in culture to determine the density of cells migrating into the scaffold as a function of time.

Figure 10:
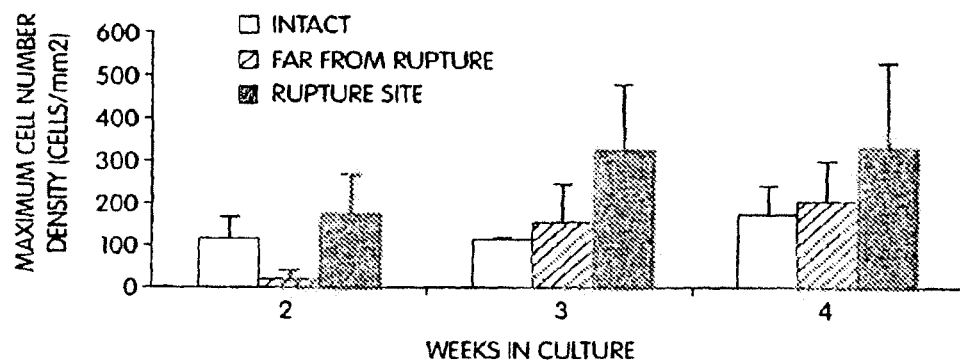
FIG. 10 is a histogram showing migration into a collagen-glycosaminoglycan (CG) scaffold from explants of intact and ruptured human anterior cruciate ligaments.

Results. Cells were noted to migrate from the anterior cruciate ligament rupture site into the scaffold at the earliest time point (two weeks). Higher densities of cells were noted to migrate from explants obtained at the site of rupture than from explants taken far from the rupture site, or from the intact anterior cruciate ligaments (FIG. 10). Two-way ANOVA demonstrated explant location in the ligament had a significant effect on cell number density in the scaffold for the ruptured ligaments (p<0.0001), but that time in culture did not have a significant effect. Maximum cell number densities in the scaffold (335±200 cells/mm$^2$).

Discussion and conclusions. The cells of the ruptured human anterior cruciate ligament are able to migrate to an adjacent scaffold, and do so at higher rates than cells from the intact ligament. The anterior cruciate ligament cells in the collagen-glycosaminoglycan scaffold reach cell number densities at some sites similar to those of the intact anterior cruciate ligament. Thus, this EXAMPLE's approach of developing a ligament repair scaffold, or "bridge" which reconnects the ruptured ligament ends is useful in facilitating ligament repair after rupture.

EXAMPLE 7

Angiogenesis and Fibroblast Proliferation in the Human Anterior Cruciate Ligament after Complete Rupture This EXAMPLE was performed to determine if two of the biologic responses required for regeneration of tissue (revascularization and fibroblast proliferation) occur in the human anterior cruciate ligament after injury.

Materials and methods. Twenty-three ruptured anterior cruciate ligament reminants were obtained from 17 men and 6 women (ages 20 to 46, average 31 years), undergoing anterior cruciate ligament reconstruction. The ruptured ligaments were obtained between 10 days and 2 years after rupture. Then intact ligaments were obtained from 3 men and 7 women (ages 57 to 83, average 69 years) undergoing total knee arthroplasty for degenerative joint disease. The ligaments were fixed in formalin, embedded in paraffin, sectioned longitudinally and stained with hematoxylin and eosin and a monoclonal antibody (Sigma Chemical, St. Louis, Mo.) for alpha-smooth muscle actin ($\alpha$-sm). Histomorphometric analysis was performed to determine cell number density, blood vessel density, nuclear aspect ratio and the percentage of $\alpha$-sm positive, non-vascular cells at 1-2 mm increments along the length of the ligament section. Blood vessel density was determined by measuring the width of the section and counting the number of vessels crossing that width. Two-way ANOVA was used to determine the significance of time after injury, distance from the site of injury, and patient age on the cell number density, blood vessel density, nuclear morphometry and $\alpha$-sm positive staining within the ligaments. Bonferroni-Dunn post-hoc testing was used to generate specific p values between groups.

Results. No bridging clot or tissue was noted grossly between the femoral and tibial reminants at the time of retrieval for any of the ruptured ligaments. Four progressive phases of response were seen in the ligament reminants with time.

Phase I. Inflammation. Ligament edema observed grossly and inflammatory cells within the tissue dominated the first three weeks after rupture. Dilated arterioles and intimal hyperplasia were noted. Loss of the regular crimp pattern was noted near the site of injury, but maintained 4-6 mm from the site of injury.

Phase II. Epiligamentous regeneration. Between three and eight weeks after rupture, gradual overgrowth of epiligamentous tissue with a synovial sheath was noted to form over the ruptured end of the ligament remnant. Histologically, this phase was characterized by a relatively unchanging blood vessel density and cell number density within the remnant.

Phase III. Proliferation. Between right and twenty weeks after rupture, the proliferative response in the epiligamentous tissue subsided and a marked increase in cell number density and blood vessel density within the ligament remnant was noted. Fibroblasts were the predominant cell type. Vascular endothelial capillary buds were noted to appear at the beginning of this phase, and loops from anastomoses of proximal sprouts began to form a diffuse network of immature capillaries within the ligament remnant.

Phase IV. Remodeling and Maturation. Between one and two years after ligament rupture, remodeling and maturation of the ligament remnant were seen. The ligament ends were dense and white, with little fatty synovium seen overlying them. Histologically, the fibroblast nuclei were increasingly uniform in shape and orientation, with the longitudinal axis of the nuclei demonstrating increasing alignment with the longitudinal axis of the ligament remnant. Decreased cell number density and blood vessel density were seen during this phase, to a level similar to that seen in the intact human anterior cruciate ligaments.

Figure 11:
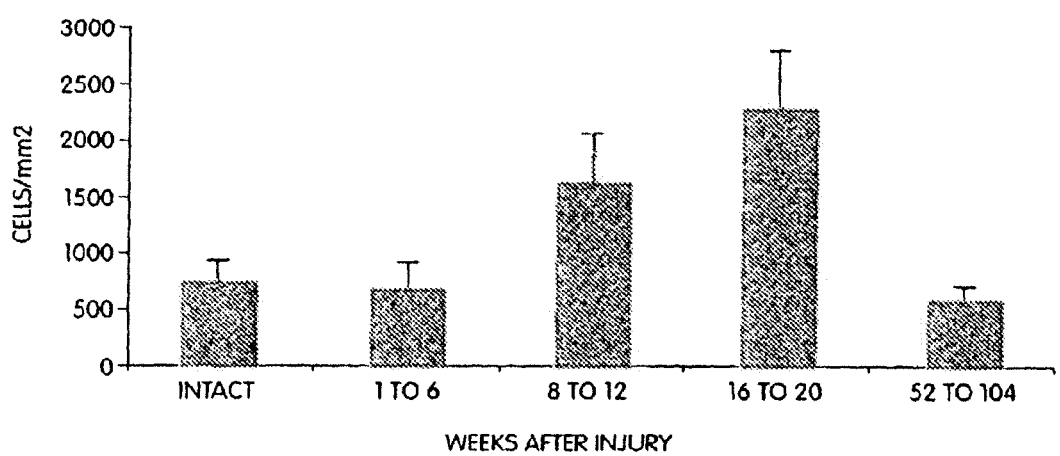
FIG. 11 is a histogram showing the cell number density near the site of rupture in the human anterior cruciate ligament as a function of time after injury.

Cell number density in the ligament in the ligament after rupture was dependent on time after injury and distance from the injury site. The cell number density within the ligament remnant peaked at 16 to 20 weeks (FIG. 11, $p<0.005$), and was highest near the site of the injury at all time points (TABLE 1). Patient age was not found to significantly affect cell number density ($p>0.80$). Blood vessel density was dependent on time after injury, with a peak at 16 to 20 weeks ($p<0.003$). Age did not have a significant effect on vessel density. Cells straining positive for the contractile actin isoform, $\alpha$-sm, were present throughout the intact and ruptured anterior cruciate ligaments. Time after injury and age of the patient were not found to significantly effect the percentage of cells straining positive.

TABLE 1

Histomorphometry of the intact ACL and distal remnant of the ruptured ACL

| Weeks post-rupture | Ruptured edge | 1 mm from edge | 2 mm from edge | 4 mm from edge |
|---|---|---|---|---|
| Intact ACL (n = 10) | | | | |
| Cell density (#/mm$^2$) | 701 ± 201 | 525 ± 108 | 539 ± 91 | 294 ± 37 |
| Vessel density (#/mm) | 1.5 ± 0.16 | 1.2 ± 0.2 | 0.6 ± 0.12 | 0.24 ± .03 |
| % SMA positive cells | 4.7 ± 1.0 | 7.3 ± 1.7 | 10.7 ± 3.0 | 15 ± 3.9 |
| 1 to 6 weeks (n = 6) | | | | |
| Cell density (#/mm$^2$) | 614 ± 249 | 476 ± 267 | 420 ± 210 | 254 ± 48 |
| Vessel density (#/mm) | 4 ± 3.3 | 2.9 ± 2.6 | 5.0 ± 2.9 | 0.8 ± 0.2 |
| % SMA positive cells | 2.3 ± 1.4 | 1.9 ± 1.1 | 1.0 ± 0.3 | 0.83 ± 0.31 |
| 8 to 12 weeks (n = 5) | | | | |
| Cell density (#/mm$^2$) | 1541 ± 451 | 1272 ± 363 | 956 ± 249 | 701 ± 162 |
| Vessel density (#/mm) | 5.1 ± 3.1 | 4.0 ± 2.6 | 3.0 ± 2.1 | 2.2 ± 1.0 |
| % SMA positive cells | 1.3 ± 0.76 | 1.3 ± 0.28 | 1.1 ± 0.33 | 0.5 ± 0.3 |

TABLE 1-continued

Histomorphometry of the intact ACL and distal remnant of the ruptured ACL

| Weeks post-rupture | Ruptured edge | 1 mm from edge | 2 mm from edge | 4 mm from edge |
|---|---|---|---|---|
| 16 to 20 weeks (n = 6) | | | | |
| Cell density (#/mm$^2$) | 2244 ± 526 | 1522 ± 285 | 1037 ± 280 | 833 ± 312 |
| Vessel density (#/mm) | 13.3 ± 4.9 | 4.0 ± 1.3 | 5.2 ± 2.0 | 2.9 ± 1.6 |
| % SMA positive cells | 0.6 ± 0.3 | 0.4 ± 0.2 | 0.3 ± 0.2 | 0.3 ± 0.3 |
| 52 to 104 weeks (n = 6) | | | | |
| Cell density (#/mm$^2$) | 559 ± 115 | 601 ± 204 | 718 ± 241 | 590 ± 46 |
| Vessel density (#/mm) | 2.1 ± 2.0 | 1.5 ± 1.3 | 1.2 ± 0.7 | 1.3 ± 0.6 |
| % SMA positive cells | 0.5 ± 0.3 | 0.2 ± 0.2 | 0.2 ± 0.1 | 0.5 ± 0.2 |

Discussion. The human anterior cruciate ligament undergoes a process of revascularization and fibroblast proliferation after complete rupture. The healing response can be described in four phases, with a peak in activity at 4 to 5 months after rupture. This response is similar to that seen in other dense, organized, connective tissues which heal, such as the medial collateral ligament, with two exceptions: (1) the lack of any tissue bridging the rupture site after injury, and (2) the presence of an epiligamentous regeneration phase. The results of this EXAMPLE, showing that fibroblast proliferation and angiogenesis occur within the human anterior cruciate ligament remnant, are important to the development of future methods of facilitating anterior cruciate ligament healing. Harnessing the neovascularization and cell proliferation, and extending it into the gap between ruptured ligament ends provides guidance for a method of anterior cruciate ligament repair.

EXAMPLE 8

Outgrowth of Chondrocytes from Human Articular Cartilage Explants and Expression of Alpha-Smooth Muscle Actin The objectives of this EXAMPLE were to investigate the effects of enzymatic treatment on the potential for cell outgrowth from adult human articular cartilage and to determine if α-sm is present in chondrocytes in articular cartilage and in the outgrowing cells.

Material and methods. Samples of articular cartilage were obtained from 15 patients undergoing total joint arthroplasty for osteoarthrosis. While the specimens were obtained from patients with joint pathology, areas of cartilage with no grossly noticeable thinning, fissuring, or fibrillation were selected. Using a dermal punch, cylindrical samples (4.5 mm diameter and 2-3 mm thick), were cut from the specimens. Explants were cultured in 6-well culture dishes and oriented so that deep zone of the tissue contracted the culture dish. In the first test, 20 cartilage samples were obtained from each of the 9 patients. Four plugs of cartilage were allocated to one of five groups that received collagenase treatment for 0, 1, 5, 10, or 15 min. The time to cell attachment after outgrowth was determined and cultures were terminated after 28 days. From 6 of the 9 patients, additional plugs, untreated and treated with collagenase for 15 minutes, were evaluated for α-sm, immediately after treatment, and at 6, 14 and 20 days in culture. In the second test, 24 cartilage plugs were obtained from each of 6 additional patients. Four plugs were allocated to 5 groups receiving a different enzymatic treatment for 15 min. and a sixth untreated control group: (a) 380 U/ml clostridial collagenase (0.1%; Sigma Chemical, St. Louis, Mo.); (b) 1100 U/ml hyaluronidase (0.1%; Sigma Chemical); (c) 1 U/ml chondroitinase ABC (Sigma Chemical), (d) 0.05% trypsin (Life Technologies); and (e) 1100 U/ml hyaluronidase followed by 380 U/ml collagenase (7.5 min. in each). The days when cell outgrowth (round cells separated from the explant) and cell attachment (elongated cells) were first evident were recorded. All cultures were terminated after 30 days. If no outgrowth was noted, time to outgrowth was assigned 28 or 30 days for exps. 1 and 2, respectively. Explants allocated for immunohistochemistry were fixed in 10% formalin, paraffin embedded and cut to 7 μm sections. Sections were stained with a α-sm monoclonal antibody (Sigma Chemical, St. Louis, Mo.). Statistical analysis was performed by ANOVA with Fisher's PLSD post-hoc test.

Results. The time to cell attachment after outgrowth from untreated explants was >4 weeks with no sign of outgrowth in 6 of 9 explants. There was a significant effect of collagenase treatment time on the time to cell attachment ($p<0.001$).

TABLE 2

Times to cell attachment after collangenase treatments of cartilage explants (Mean ± SEM: n = 9)

| Explant Treatment | Days |
|---|---|
| Untreated | 27.2 ± 0.4 |
| 1-min collangenase | 15.4 ± 2.6 |
| 5-min collangenase | 9.9 ± 1.0 |
| 10-min collangenase | 6.2 ± 0.4 |
| 15-min collangenase | 5.9 ± 0.4 |

Treatments with hyaluronidase, chondroitinase ABC, and trypsin, had no effect on the times to outgrowth and attachment (TABLE 3). In contrast, the collagenase treatment yielded a time to outgrowth of at least 1 order of magnitude less than the untreated group (2.2±0.2 vs 27.7±1.5 days, respectively; TABLE 3). Treatment of the explants with hyaluronidase+collagenase yielded results that were comparable to treatment with collagenase alone. Signs of attachment of the outgrowth cells were generally found within 3 days of the first evidence of outgrowth.

TABLE 3

Times to outgrowth and attachment of chondrocytes
from articular cartilage explants after various enzymatic treatments
(Mean ± SEM; n = 6)

| Group | Time to Outgrowth (days) | Time to Attachment (days) |
|---|---|---|
| Untreated | 27.7 ± 1.5 | 28.5 ± 1.0 |
| Collagenase | 2.2 ± 0.2 | 5.8 ± 0.6 |
| Hyaluronidase | 25.0 ± 1.6 | 27.5 ± 0.9 |
| Chondroitinase ABC | 29.2 ± 0.8 | 29.7 ± 0.3 |
| Trypsin | 28.8 ± 1.2 | 29.5 ± 0.5 |
| Hyaluronidase + Collagenase | 2.5 ± 0.3 | 5.0 ± 0.4 |

Immunohistochemistry revealed that approximately 70% of the chondrocytes in the explants stained positive for the α-sm isoform (TABLE 4). The chromogen was restricted to the cytoplasm of the cells that displayed the typical chondrocyte morphology and location in lacunae. There was no significant difference in the percentage of α-sm-staining cells in the explants in the collagenase and untreated control groups, at any time period in culture (TABLE 4). There were significant increases in the percentage of α-sm-containing cells in the untreated and collagenase-treated groups after 14 days in culture, compared to the initial values (TABLE 4; $p<0.02$ and $p<0.01$, respectively). After 20 days, there was a decrease in the number of cells in all explants and a significant reduction ($p<0.0001$) in the % of α-sm-containing cells in the explants, compared to 14 days (TABLE 4). The percentage of attached cells from all groups that stained positive for α-sm was greater than 90%.

TABLE 4

The percentage of cells in untreated and collangenase-
treated articular cartilage explants containing α-smooth
muscle actin, after various time in culture
(Mean ± SEM.; n = 6)

| Groups | Initial | 6 days | 14 days | 20 days |
|---|---|---|---|---|
| Untreated | 68 ± 9 | 78 ± 7 | 92 ± 5 | 49 ± 11 |
| 15-min collagenase | 74 ± 8 | 93 ± 2 | 98 ± 2 | 51 ± 5 |

Discussion. The notable findings of this EXAMPLE were that the rate of chondrocyte outgrowth from adult human articular cartilage could be profoundly accelerated by collagenase treatment and that chondrocytes in adult human asteoarthritic articular cartilage contain a contractile actin isform not previously identified in this cell type. The investigation of cartilage from joints with arthritis is useful, as this is the population that may benefit from facilitated cartilage repair. The results of this EXAMPLE show that collagen architecture limits chondrocyte migration. Thus, we show that, if migration of chondrocytes to a wound edge in vitro can be facilitated, the cells contribute to the healing process by contracting an endogenous or exogenous scaffold bridging the defect.

EXAMPLE 9

Histologic Changes in the Human Anterior Cruciate Ligament after Rupture

This EXAMPLE was designed to determine: (a) whether the ruptured anterior cruciate ligament remnant was capable of maintaining cells within its substance after rupture, in the intrasynovial environment; (b) whether an increase in cell number density would occur in the anterior cruciate ligament after complete rupture; and (c) whether the ruptured ligament would revascularize after injury. Another objective was to determine if cells with a contractile actin isoform, α-sm actin were present in the healing human anterior cruciate ligament.

Methods. Twenty-three ruptured anterior cruciate ligament remnants were obtained from seventeen men and six women (ages twenty to forty-six, average thirty-one years), undergoing anterior cruciate ligament reconstruction (TABLE 5). The ruptured ligaments were obtained from ten days to two years after rupture. Ten contemporaneous intact ligaments were obtained from three men and seven women (ages fifty seven to eighty-three, average sixty-nine years) undergoing total knee arthroplasty for degenerative joint disease (TABLE 5). The intact ligaments were resected from their insertion sites with a scalpel by the surgeon. The majority of the ruptured ligaments were gently lifted from the posterior cruciate ligament, transected at their tibial attachment, and removed arthroscopically by the surgeon. Ruptured ligaments retrieved at ten days to three weeks were removed at the time of open reconstruction for multiple ligament injury.

TABLE 5

Patient Demographics for Intact and Ruptured ACL tissue

| Intact Ligaments | | | Ruptured Ligaments | | | |
|---|---|---|---|---|---|---|
| Patient No. | Age (years) | Gender | Patient No. | Age (years) | Gender | Time from rupture* |
| 1 | 61 | Man | 11 | 34 | Man | 1 week |
| 2 | 65 | Woman | 12 | 25 | Man | 3 weeks |
| 3 | 65 | Woman | 13 | 28 | Woman | 3 weeks |
| 4 | 83 | Woman | 14 | 45 | Woman | 4 weeks |
| 5 | 73 | Woman | 15 | 24 | Man | 6 weeks |
| 6 | 75 | Woman | 16 | 24 | Woman | 6 weeks |
| 7 | 62 | Woman | 17 | 14 | Woman | 8 weeks |
| 8 | 65 | Man | 18 | 20 | Woman | 8 weeks |
| 9 | 65 | Woman | 19 | 24 | Man | 8 weeks |
| 10 | 71 | Man | 20 | 29 | Man | 8 weeks |
| | | | 21 | 45 | Man | 12 weeks |
| | | | 22 | 42 | Man | 16 weeks |
| | | | 23 | 41 | Man | 16 weeks |
| | | | 24 | 24 | Man | 16 weeks |
| | | | 25 | 31 | Man | 16 weeks |
| | | | 26 | 46 | Man | 20 weeks |
| | | | 27 | 34 | Man | 20 weeks |
| | | | 28 | 30 | Man | 52 weeks |
| | | | 29 | 22 | Man | 64 weeks |
| | | | 30 | 21 | Man | 104 weeks |
| | | | 31 | 20 | Man | 104 weeks |
| | | | 32 | 44 | Woman | 104 weeks |
| | | | 33 | 36 | Man | 156 weeks |

*Time from rupture designated to the nearest week, or the nearest 4 week period for the later specimens.

Histology and Immunohistochemistry. The ligaments were marked with a suture at the site of tibial transection, and fixed in neutral buffered formalin for one week. After fixation, specimens were embedded longitudinally in paraffin and 7 μm thick longitudinal sections were microtomed and fixed onto glass slides. Representative sections from each ligament were stained with hematoxylin and eosin and with a monoclonal antibody to α-sm actin (Sigma Chemical, St Louis, Mo., USA). In the immunohistochemical procedure, deparaffinized, hydrated slides were digested with 0.1% trypsin (Sigma Chemical, St. Louis, Mo., USA) for 20 minutes. Endogenous peroxidase was quenched with 3% hydrogen peroxide for 5 minutes. Nonspecific sites were blocked using 20% goat serum for thirty minutes. The sections were then incubated with the mouse monoclonal antibody to α-sm actin for 1 hr at room temperature. A negative control section on each microscope slide was incubated with non-immune mouse serum diluted to the same protein content, instead of the α-sm actin antibody, to monitor for non-specific staining. The sections were then incubated with a biotinylated goat anti-mouse IgG secondary antibody for thirty minutes followed by thirty minutes of incubation with affinity purified avidin. The labeling was developed using the AEC chromogen kit (Sigma Chemical, St Louis, Mo.) for 10 minutes. Counterstaining with Mayer's hematoxylin for twenty minutes was followed by a 20-minute tap water wash and coverslipping with warmed glycerol gelatin.

Method of Evaluation. Histological slides were examined using a Vanox-T AH-2 microscope (Olympus, Tokyo, Japan) with normal and polarized light. For the histomorphometric measurements, the intact ligaments were evaluated at adjacent to the site of transection from the femoral attachment, and at one, two, four and six mm distal to the transection. These analyses did not include the ligament insertion into bone. The ruptured ligaments were evaluated at the ruptured edge, and at 1, 2, 4 and 6 mm distal to the site of rupture (toward the tibial insertion). At each location, three 0.1 mm areas were evaluated by determining the total cell number density and the predominant nuclear morphology, and by calculating the percentage of cells positive for the α-sm actin isoform. Between 20 and 230 cells were counted at each of the three areas. At each location, the total number of cells was counted and divided by the area of analysis to yield the cell number density, or cellularity. The cell morphology was classified based on nuclear shape: fusiform, ovoid, or spheroid. Fibroblasts with nuclei with aspect ratios (i.e., length divided by width) greater than ten were classified as fusiform, those with aspect ratios between five and ten as ovoid, and those with nuclear aspect ratios less than five as spheroid. The total number of blood vessels crossing the section at each location was divided by the width of the section at each location to obtain a blood vessel density for each location.

Smooth muscle cells surrounding vessels were used as internal positive controls for determination of α-sm actin positive cells. Positive cells were those that demonstrated chromogen intensity similar to that seen in the smooth muscle cells on the same microscope slide and that had significantly more intense stain than the perivascular cells on the negative control section. Any cell with a questionable intensity of stain (e.g., light pink tint) was not counted as positive. The α-sm actin positive cell density was reported as the number of stained cells divided by the area of analysis and the percentage of α-sm actin positive cells was determined by dividing the number of stained cells by the total number of cells in a particular histologic zone.

Polarized light microscopy was used to aid in defining the borders of fascicles and in visualizing the crimp within the fascicles. Measurement of the crimp length was performed using a calibrated reticule under polarized light.

After the complete in-substance rupture of the human anterior cruciate ligament, four progressive chronological phases of healing response were seen.

Figure 12:
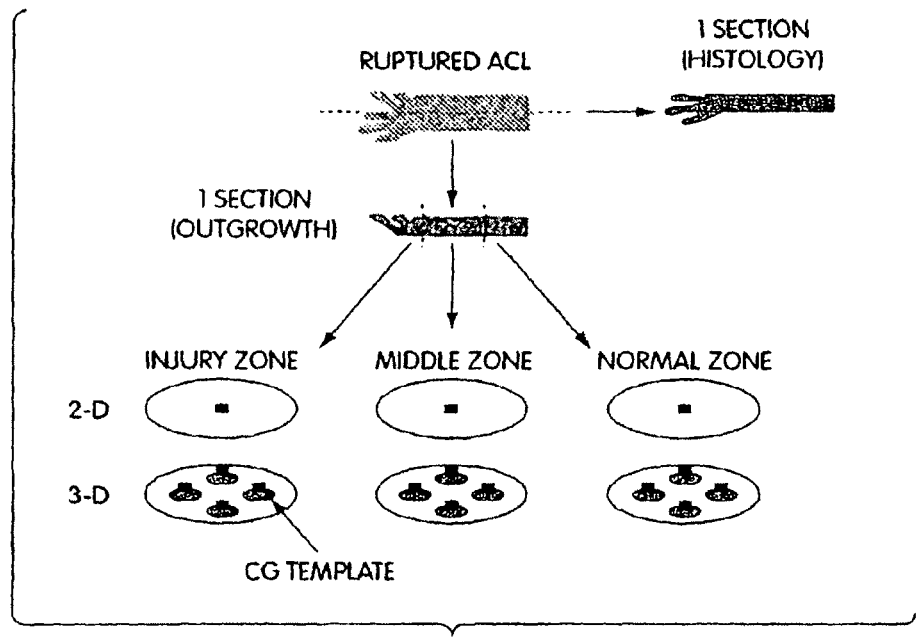
FIG. 12 is a schematic of tissue allocation for explants for 2-dimensional (2-D) and 3-dimensional (3-D) migration constructs.

Phase I. Inflammation. Within the first few weeks post-rupture, the synovial fluid encountered on entering the joint was rust-colored, and was easily suctioned from the knee. No blood clots were found within the knee joint. The entire remnants were swollen and edematous and the synovial and epiligamentous tissue was grossly disrupted. Blood clot was seen covering part of the ligament remnants, but no connection between the femoral and tibial ends was visible grossly. Near the site of rupture, the ligament ends were of friable, stringy, tissue previously described as "mop-ends" (FIG. 12A).

Histologically, the ligament remnants retrieved in this time period were populated by fibroblasts and several types of inflammatory cells: polymorphonuclear neutrophils, lymphocytes, and macrophages. The inflammatory cells were found in greatest concentration around blood vessels near the site of injury. Macrophages appeared to be actively phagocytosing cell and tissue debris.

Arterioles near the site of injury were noted to be dilated, with intimal hyperplasia (FIG. 12A) consisting of dramatic smooth muscle cell wall proliferation and thickening. Venules were noted to be dilated, with less evident smooth muscle cell hyperplasia. Capillaries appeared congested, with rouleaux and thrombus formation noted in their lumens.

The collagenous extracellular matrix appeared disorganized and edematous near the site of injury. Loss of the regular organization of the collagen fibers was evident (FIG. 12A) and replacement with disorganized, less dense, amorphous tissue was seen. The cells populating this amorphous tissue consisted of both fibroblasts and inflammatory cells. At the site of rupture, several adjacent ruptured distal fascicles were bridged by a fibrin clot at ten days, and several of the ruptured fascicle ends were covered by a twenty- to fifty micrometer thick fibrin clot. However, no gaps larger than 700 micrometers contained any bridging material.

Phase II. Epiligamentous Regeneration. Between three and eight weeks after rupture, gradual growth of epiligamentous tissue with a synovial sheath was noted over the ruptured end of the ligament remnant, giving it a smoother, mushroom appearance, different from the mop-ends seen in the earlier specimens (FIG. 12B). No tissue was noted to bridge the gap between the proximal and distal segments, although several of the distal remnants were adherent to the sheath of the intact posterior cruciate ligament.

Histologically, the epiligamentous regeneration phase was characterized by a relatively unchanging cell number density and blood vessel density in the ligament remnant. After the initial influx of inflammatory cells and removal of cell and tissue debris seen in the inflammatory stage, the number of inflammatory cells decreased, and fibroblasis became the dominant cell type. The cell number density of fibroblasts was similar to that seen in the uninjured ligament and the remaining blood vessels displayed near normal morphologies, with little intimal hyperplasia. No neovascularization was noted within the ligament fascicles.

Most of the changes occurred in the epiligament that displayed an increase in cell number density and blood vessel density. The vascular epiligamentous tissue was noted to gradually extend over the ruptured ligament end, encapsulating the mop-ends of the individual capsules. Thickening of the epiligament and fibroblast proliferation were seen to occur during this time period. A synovial layer, similar to that seen covering the epiligamentous tissue in the intact anterior cruciate ligament, was noted to form over the extending neoepiligamentous tissue.

Phase III. Proliferation. By eight weeks, the distal anterior cruciate ligament remnants were completely encapsulated by a synovial sheath, and few remaining mop-ends were seen grossly (FIG. 12C). No tissue was visible between the proximal and distal ligament remnants. Several of the distal remnants were noted to be adherent to the periligamentous tissue of the posterior cruciate ligament.

Histologically, the period between eight and twenty weeks after rupture was characterized by increasing cell number density and blood vessel density in and among the fascicles of the ligament remnant. Fibroblasts were the predominant cell type, and the entire remnant became increasingly cellular, with a peak cell number density at sixteen to twenty weeks.

The cellular orientation remained disorganized, with few cell nuclei with longitudinal axes parallel to that of the ligament. Vascular endothelial capillary buds were seen during this phase, and loops from anastomoses of proximal sprouts were noted to form a diffuse network of immature capillaries (FIG. 12C).

The collagenous material of the ligament fascicles remained disorganized near the site of injury. No preferential orientation was seen; however, bands of parallel collagen fibers were noted to begin to form and develop a waveform similar to the crimp seen in the intact human anterior cruciate ligament. These areas were a small component of the remnant, and the longitudinal axis of the waveform was rarely aligned with the longitudinal axis of the ligament remnant.

The epiligamentous tissue remained vascular and was relatively unchanged in appearance throughout this phase. The synovial layer persisted as a two-cell layer continuous over the epiligamentous tissue. Immunohistochemistry revealed α-sm actin containing cells distributed throughout the intact and ruptured ligaments, albeit in relatively low percentages (TABLE 6). Of note was the abundance of such cells in certain regions of the synovium and epiligamentous tissue. In some cases, the α-sm actin cells in the synovium were clearly separate from vascular smooth muscle cells and pericytes in the underlying epiligamentous tissue. In many areas, however, such a distinction was not possible as the synovium merged with a highly vascular epiligament.

Phase IV. Remodeling and Maturation. Between 1 and 2 years after ligament rupture, remodeling and maturation of the ligament remnant were seen. The ligament ends were dense and white, with little fatty synovium seen overlying them (FIG. 12D). No tissue was noted to connect the two ends of the ligament.

Histologically, the fibroblast nuclei were increasingly fusiform with the long axis of the nucleus aligned with the longitudinal axis of the ligament. There was decreased blood vessel density within the ligament remnant. The epiligamentous tissue continued to decreased in thickness; however, the synovial sheath persisted. A more axial alignment of the collagen fascicles was seen. The cell number density decreased to a level similar to that seen in the intact human anterior cruciate ligament.

Histomorphometry. The numeric results for the ligaments at each of the time points are provided in TABLE 6. The evaluation of the percentage of α-sm actin-positive cells did not include the synovium or the epiligamentous tissue where the distinction of vascular and non-vascular cells could not be confidently made.

In the intact control group of anterior cruciate ligaments, there was a decrease in cell number density and vascularity proceeding from proximal to distal and an increase in the sphericity of the cell nuclei, and in the percentage of α-sm actin-positive cells.

TABLE 6

Histomorphometric measurements of the intact and ruptured human anterior cruciate ligament

| Weeks out from rupture | Proximal edge | 1 mm from edge | 2 mm from edge | 4 mm from edge | 6 mm from edge |
|---|---|---|---|---|---|
| Intact Ligaments | | | | | |
| Cell density(#/mm$^2$)* | 701 ± 120 | 525 ± 108 | 539 ± 91 | 294 ± 39 | 265 ± 37 |
| Nuclear aspect ratio | 6.1 ± 0.9 | 4.5 ± 0.8 | 4.3 ± 0.6 | 3.6 ± 0.6 | 2.4 ± 0.5 |
| Blood vessel density (#/mm) | 1.5 ± 0.16 | 1.2 ± 0.2 | 1.0 ± 0.2 | 0.60 ± 0.12 | 0.24 ± 0.03 |
| % of cells positive for SMA | 4.7 ± 1.0 | 7.3 ± 1.7 | 10.7 ± 3.0 | 15 ± 3.9 | 17 ± 4.3 |
| n | 10 | 10 | 10 | 10 | 10 |
| 1 to 6 weeks | | | | | |
| Cell density(#/mm$^2$)* | 614 ± 249 | 476 ± 267 | 420 ± 210 | 254 ± 48 | 231 ± 30 |
| Nuclear aspect ratio | 4.5 ± 1.0 | 3.9 ± 0.8 | 3.7 ± 0.9 | 4.2 ± 0.7 | 4.3 ± 1.2 |
| Blood vessel density (#/mm) | 4 ± 3.3 | 2.9 ± 2.6 | 5.0 ± 2.9 | 2.0 ± 1.2 | 0.8 ± 0.2 |
| % of cells positive for SMA | 2.3 ± 1.4 | 1.9 ± 1.1 | 1.0 ± 0.3 | 0.83 ± 0.31 | 0.36 ± 0.12 |
| n | 6 | 6 | 6 | 6 | 6 |
| 8 to 12 weeks | | | | | |
| Cell density(#/mm$^2$)* | 1541 ± 451 | 1272 ± 363 | 965 ± 249 | 701 ± 162 | 497 ± 151 |
| Nuclear aspect ratio | 6.2 ± 1.0 | 4.3 ± 1.0 | 3.8 ± 1.0 | 2.9 ± 1.0 | 4.1 ± 1.3 |
| Blood vessel density (#/mm) | 5.1 ± 3.1 | 4.0 ± 2.6 | 3.0 ± 2.1 | 2.2 ± 1.0 | 2.1 ± 1.0 |
| % of cells positive for SMA | 1.3 ± 0.76 | 1.3 ± 0.28 | 1.1 ± 0.33 | 0.5 ± 0.3 | 0.33 ± 0.19 |
| n | 5 | 5 | 5 | 5 | 5 |
| 16 to 20 weeks | | | | | |
| Cell density(#/mm$^2$)* | 2244 ± 526 | 1522 ± 285 | 1037 ± 280 | 833 ± 312 | 1009 ± 437 |
| Nuclear aspect ratio | 5.4 ± 1.0 | 4.8 ± 0.2 | 4.6 ± 0.5 | 5.3 ± 1.2 | 3.8 ± 1.3 |
| Blood vessel density (#/mm) | 13.3 ± 4.9 | 4.0 ± 1.3 | 5.2 ± 2.0 | 2.9 ± 1.6 | 3.3 ± 2.0 |
| % of cells positive for SMA | 0.58 ± 0.26 | 0.42 ± 0.2 | 0.31 ± 0.16 | 0.25 ± 0.25 | 1.2 ± 0.65 |
| n | 6 | 6 | 6 | 6 | 6 |
| 52 to 104 weeks | | | | | |
| Cell density(#/mm$^2$)* | 559 ± 115 | 601 ± 204 | 718 ± 241 | 590 ± 46 | 546 ± 45 |
| Nuclear aspect ratio | 3.7 ± 0.6 | 4.0 ± 0.9 | 4.2 ± 0.5 | 3.3 ± 1.1 | 3.7 ± 0.5 |
| Blood vessel density (#/mm) | 2.1 ± 2.0 | 1.5 ± 1.3 | 1.2 ± 0.7 | 1.6 ± 0.8 | 1.3 ± 0.6 |
| % of cells positive for SMA | 0.5 ± 0.3 | 0.22 ± 0.16 | 0.19 ± 0.11 | 0.53 ± 0.26 | 1.1 ± 0.9 |
| n | 6 | 6 | 6 | 6 | 6 |

*all values are ± SEM.

Figure 13:
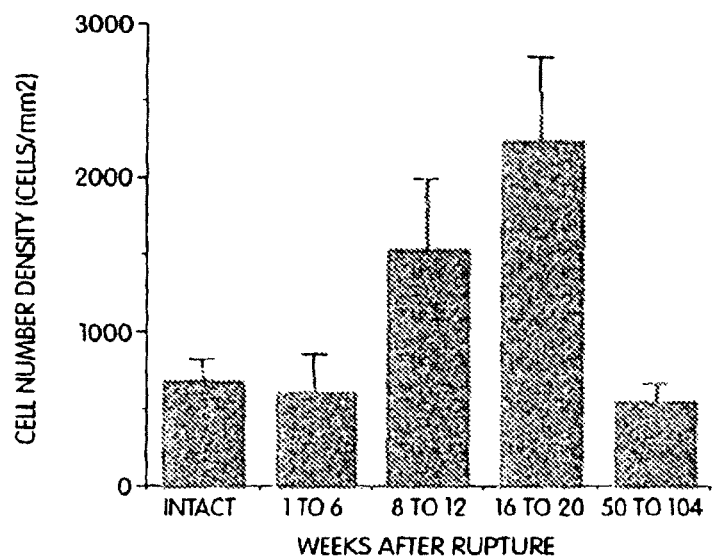
FIG. 13 is a histogram demonstrating changes in cell number density near the site of injury as a function of time after complete anterior cruciate ligament rupture and comparison with the cell number density in the proximal unruptured anterior cruciate ligament. Error bars represent the standard error of the mean (SEM).

Two-way ANOVA demonstrated that the cell number density in the human ruptured anterior cruciate ligament was significantly affected by location in the ligament remnant and time after rupture. The cell number density was highest near the site of injury at all time points. This cellularity increased significantly to a maximum at sixteen to twenty weeks (FIG. 13; Bonferroni-Dunn post-hoc testing, $p<0.005$) and decreased between twenty and fifty-two weeks after injury (Bonferroni-Dunn post-hoc testing, $p<0.005$). With the number of ligaments available, age and gender were not found to significantly affect cell number density (two-way ANOVA, $p>0.80$ and $p<0.40$, respectively).

The morphology of the cell nuclei was also significantly affected by the location in the ligament remnant, but not by time after injury, gender or age. Using two-way ANOVA, the proximal part of the ligament remnant was found to have cells with a higher nuclear aspect ratio when compared with cells in the more distal remnants (Bonferroni-Dunn post-hoc testing, $p<0.0005$). This pattern was also observed in the intact ligaments. Two-way ANOVA demonstrated that the morphology of the cell nuclei was significantly affected by the location in the ligament remnant ($p<0.003$), but with the numbers available, not by time after injury ($p<0.40$) or age ($p<0.70$). The effect of gender on this parameter was close ($p<0.06$) to meeting our criterion for significance ($p<0.05$) with the number of ligaments analyzed.

Figure 14:
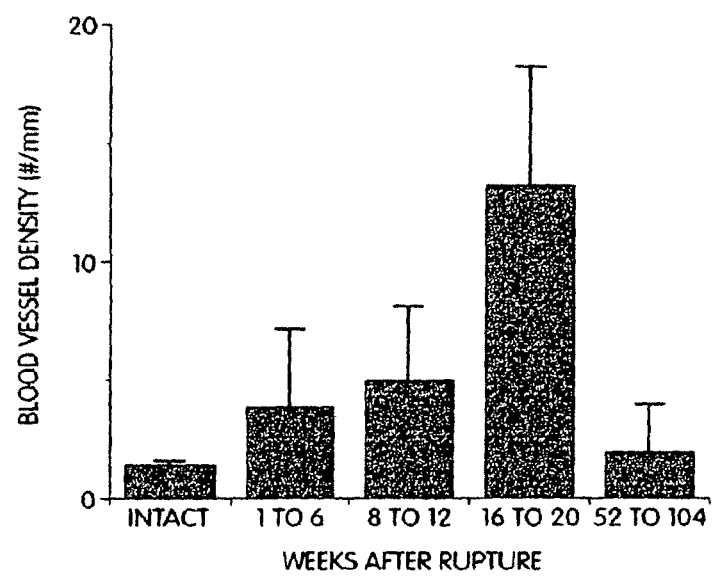
FIG. 14 is a histogram demonstrating the changes in blood vessel density near the site of injury as a function of time after complete anterior cruciate ligament rupture and comparison with the blood vessel density in the proximal unruptured anterior cruciate ligament. Error bars represent the standard error of the mean (SEM).
Figure 15A:
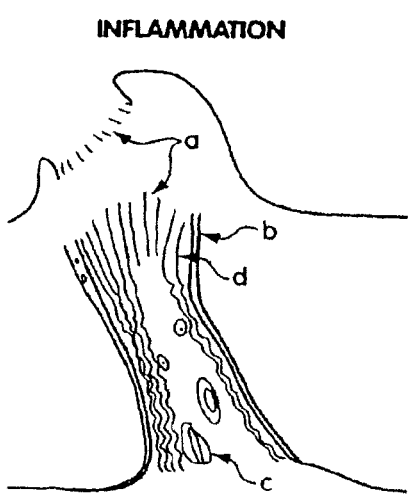
FIG. 15A shows the inflammatory phase showing mop-ends of the remnants (a), disruption of the epiligament and synovial covering of the ligament (b), intimal hyperplasia of the vessels (c) and loss of the regular crimp structure near the site of injury (d).
Figure 15B:
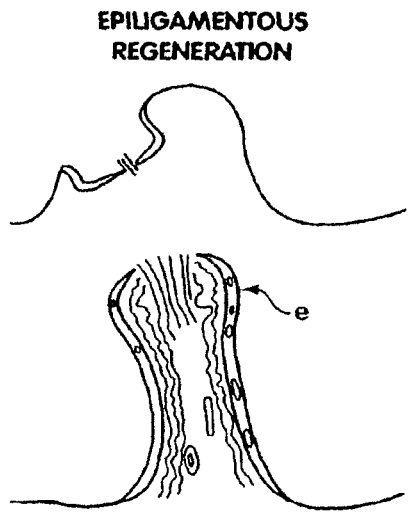
FIG. 15B shows the epiligamentous regeneration phase involving a gradual recovering of the ligament remnant by vascularized, epiligamentous tissue and synovium (e).
Figure 15C:
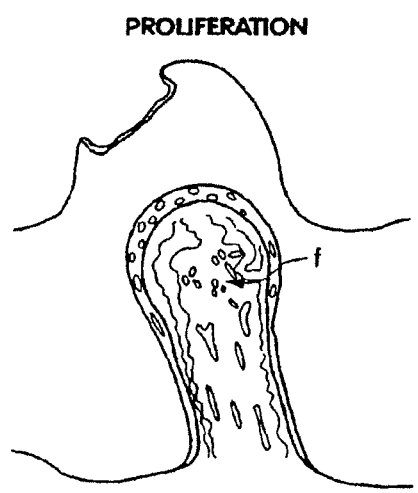
FIG. 15C shows the proliferative phase with a revascularization of the remnant with groups of capillaries (f).
Figure 15D:
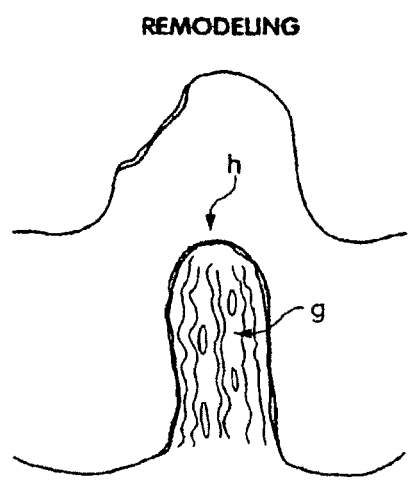
FIG. 15D shows the remodeling and maturation stage characterized by a decrease in cell number density and blood vessel density (g), and retraction of the ligament remnant (h).

The blood vessel density was found to be significantly affected by the time after injury with two-way ANOVA. The blood vessel density reached its highest value at sixteen to twenty weeks (Bonferroni-Dunn post-hoc testing, $p<0.003$) and decreased after that time point (TABLE 6). The blood vessel density decreased with distance from the ruptured edge (FIG. 14). While the effect of location on blood vessel density ($p<0.09$) did not reach the acceptance criterion of $p<0.05$ for significance using ANOVA with the number of ligaments available, its p value and examination of the data suggest a higher density of vessels near the site of injury. With the numbers available, two-way ANOVA found no significant effect on blood vessel density for age ($p<0$) or gender ($p>0.25$).

Cells which stained positive for the α-sm actin isoform were present throughout the intact and ruptured anterior cruciate ligament. Cells with all three morphologies were noted to stain positive. While two-way ANOVA found no significant effect of time after injury on α-sm actin staining ($p<0.30$) with the number of ligaments available, the ruptured ligaments had a smaller percentage of cells which stained positive when compared with the intact ligaments (TABLE 6). Two-way ANOVA also found no significant effect of location in the ligament ($p<0.90$), or age of the patient ($p<0.61$) on the percentage of cells staining positive for α-sm actin with the numbers available. Gender was found to have a significant effect on α-sm actin expression, with women having a greater percentage of cells staining positive for the α-sm actin isoform than men ($p<0.002$).

Discussion. The response to injury is similar to that reported in other dense connective tissues with two exceptions: the presence of a epiligamentous regeneration phase which lasts eight to twelve weeks, and the lack of any tissue bridging the rupture site. Other characteristics reported in dense connective tissue healing, such as fibroblast proliferation, expression of α-sm actin and angiogenesis are all seen to occur in the human anterior cruciate ligament.

The finding of a epiligamentous regeneration phase distinguishes the ruptured human anterior cruciate ligament from other connective tissues which heal successful and reconciles the other findings in this EXAMPLE of a productive response to injury with previous reports of failure of the anterior cruciate ligament cells to respond to rupture. The presence of the epiligamentous regeneration phase in this EXAMPLE illustrates the importantance of analyzing the results of primary repair or augmentation techniques. These procedures may have different results depending on the timing of repair after injury. Repair done in the first few weeks after injury may result in filling of the gap with the proliferative epiligamentous vascular tissue which is active at that time. Repair performed months after injury, when the endoligamentous tissue is proliferating, may result in a different mode of repair.

This EXAMPLE also demonstrates the lack of any tissue seen in the gap between the ligament remnants. In extraarticular tissues which successfully heal, the fibrin clot forms and is invaded by fibroblasts and gradually replaced by collagen fibers. This has been demonstrated to be instrumental in the healing process in both tendon (Buck, 66 J. Pathol. Bacteriol. 1-18 (1953) and the medial collateral ligament (Frank et al., 1 J. Orthop. Res. 179-188 (1983)). In the human anterior cruciate ligaments studied here, only one of the ruptured ligaments demonstrated any fibrin clot bridging adjacent fascicles of the tibial remnant, and none of the ruptured ligaments had any clot or tissue bridging the proximal and distal remnants, or bridging gaps greater than 700 micrometers. As the early specimens were obtained using an open technique, it is possible that the blood clot seen on the remnants formed at the time of surgery, after the synovial fluid had been removed from the joint. In the knees operated on in the first ten to twenty one days after injury, the hemarthrosis had already been lysed to a viscous liquid incapable of holding the ruptured ligament remnants together.

This EXAMPLE provides guidance for the analysis of human tissue that has been ruptured and maintained in an in vivo, intrasynovial environment until the time of retrieval.

EXAMPLE 10

The Migration of Cells from the Ruptured Human Anterior Cruciate Ligament into Collagen-Based Regeneration Templates Introduction. The overall object of the invention is to restore only the ligament tissue which is damaged during rupture, while retaining the rest of the ligament. The model used in this EXAMPLE involves filling the gap between the ruptured ligament ends with a bioengineered regeneration bridge, or template, designed to facilitate cell ingrowth and guided tissue regeneration. In this EXAMPLE, we investigated one of the critical steps in guided tissue regeneration; namely, the ability of cells in the adjacent injured ligament tissue to migrate into the regeneration template. This EXAMPLE focuses on whether the cells of the human anterior cruciate ligament cells are able to migrate to a template after the anterior cruciate ligament has been ruptured. We also wanted to determine whether the cells which migrated expressed a contractile actin isoform, α-sm actin, which may contribute to contraction of the template and self-tensioning of the ligament.

Methods. Four ruptured anterior cruciate ligaments were obtained from 4 men undergoing anterior cruciate ligament reconstruction, ages 25 to 34, with an average age of 28 years. Time between injury and ligament retrieval ranged from 6 to 20 weeks. Synovial tissue covering the ligaments was removed and the ligament remnants cut lengthwise into two sections. One longitudinal section from each ligament (n=4) was allocated for histology. The remaining section was transected into thirds along its length. Each section was divided into 5 biopsies, or explants, four of which were placed into culture with the collagen-glycosaminoglycan regeneration template, and one of which was placed onto a petri dish for 2-D explant culture (FIG. 15). The site closest to the rupture, or injury zone, contains a higher cell number density than that of the more distal remnant, which resembles the histology of the intact anterior cruciate ligament. Therefore, the more distal remnant (normal zone) was used as an age and gender matched control for the tissue obtained at the site of injury (injury zone) and 0.5 cm distal to the site of injury (middle zone).

Explant Culture on a 2-D Surface. The 12 tissue biopsies from the three sections of the four ligaments were explanted onto tissue-culture treated 35 mm wells (Corning #430343, 6 well plates, Cambridge, Mass.) and cultured in 1 cc of media containing Dulbecco's DMEMI F12 with 10% fetal bovine serum, 2% penicillin streptomycin, 1% amphotericin B, 1% L-glutamine and 2% ascorbic acid. Media was changed 3× a week. Outgrowth from the explant biopsies was recorded every three days as the surface area covered by confluent fibroblasts. The area of outgrowth was measured using an inverted microscope and a transparent grid sheet. The number of squares covered by the confluent cells was counted and the area calculated by multiplying the number by the known area of each square. The effective radius of outgrowth was calculated by dividing the total area of confluent cells by $\pi$ (3.14) and taking the square root of the result. The rate of outgrowth was then calculated by plotting the average effective radius of outgrowth as a function of time since confluent outgrowth was first observed and calculating the slope of the linear relationship. Seven zones were not found to be statistically significant (p=0.66). Two way ANOVA demonstrated the effect of explant location in the ligament had a significant effect on cell number density, but that time in culture did not have a significant effect. Cells migrating into the collagen-glycosaminoglycan scaffold demonstrated all of the three previously described ligament fibroblast morphologies: fusiform or spindle-shaped, ovoid, and spheroid.

The maximum cell number density in the template at the four week time period was found to directly correlate with cell number density of the explant tissue ($r^2$=0.24), to inversely correlate with density of blood vessels in the explant tissue ($r^2$=0.28), and not to correlate with the percentage of $\alpha$-sm actin positive cells in the explant tissue ($r^2$=0.00). All cells which migrated into the C template were found to be positive for $\alpha$-sm actin at the 1 and 2 week period.

Template Contraction. The templates were noted to decrease in size during the four weeks of culture. Those templates cultured without tissue contracted an average of 19.0%+0.7%. Templates cultured with tissue contracted between 17 and 96%. A greater maximum cell number density of $\alpha$-sm actin positive cells within the template was found to correlate with a greater rate of scaffold contraction ($r^2$=0.74).

The 3-D culture substrate used in this EXAMPLE was a highly porous collagen-glycosaminoglycan matrix, composed of type I bovine hide collagen and chondroitin-6-sulfate, prepared by freeze-drying the collagen-glycosaminoglycan dispersion under specific freezing conditions (Yannas et al., 8 Trans Soc Biomater. 146 (1985)) to form a tube with pore orientation preferentially oriented, longitudinally. The average pore size of the collagen-glycosaminoglycan scaffold manufactured in this manner has previously been reported as 100 gm (Chamberlain, *Long Term Functional And Morphological Evaluation Of Peripheral Nerves Regenerated Through Degradable Collagen Implants*. (M.S. Thesis Massachusetts Institute of Technology, 1998) (on file with the MIT Library)).

Immunohistochemistry. The expression of $\alpha$-sm actin was determined using monoclonal antibodies. For the 3-D culture specimens, deparaffinized, hydrated slides were digested with 0.1% trypsin (Sigma Chemical, St. Louis, Mo., USA) for 20 minutes. Endogenous peroxide was quenched with 3% hydrogen peroxide for 5 minutes. Nonspecific sites were blocked using 20% goat serum for 30 minutes. The sections were then incubated with mouse anti-$\alpha$-sm actin monoclonal antibody (Sigma Chemical, St. Louis, Mo., USA) for one hour at room temperature. Negative controls were incubated with mouse serum diluted to an identical protein content. The sections were then incubated with biotinylated goat anti-mouse IgG secondary antibody for 30 minutes followed by thirty minutes of incubation with affinity purified avidin. The labeling was developed using the AEC chromagen kit (Sigma Chemical, St. Louis, Mo.) for ten minutes. Counterstaining with Mayer's hematoxylin for 20 minutes was followed by a 20 minute tap water wash and coverslipping with warmed glycerol gelatin.

Histology of the Ligament Fascicles. The proximal one-third was populated predominantly by fusiform and ovoid cells in relatively high density, and the distal two-thirds was populated by a lower density of spheroid cells. The levels of transection used to obtain the biopsies were resulted in an injury zone which contained an average cell number density of 2083+982 cells/mm$^2$ (n=4), a middle zone with an average cell number density of 973+397 cells/mm$^2$ (n=4), and a normal zone with an average cell density of 803+507 cells/mm$^2$ (n=4). The cell number density in the injury zone was higher in the specimen obtained twenty weeks after injury (4318 cells/mm$^2$, n=1) when compared with the remnants obtained six weeks (394 cells/mm$^2$, n=1) and eight weeks after injury (1811 cells/mm$^2$, n=2). $\alpha$-sm actin immunohistochemistry of the ruptured ligaments showed positive staining in 2 to 20% of fibroblasts not associated with blood vessels.

2-D Culture Outgrowth. The outgrowth of cells onto the 2-D culture dishes was observed to occur as early as 3 days and as late as 21 days, with outgrowth first detected at an average of 6.6±2.0 days after explanting. Explant size was not found to correlate with the time of onset or rate of outgrowth. Linear regression analysis of the plot of effective outgrowth radius versus time for all explants that demonstrated confluent outgrowth had a coefficient of determination of 0.98. The average rate of outgrowth, represented by the slope of this plot, was 0.25 mm/day.

Figure 16:
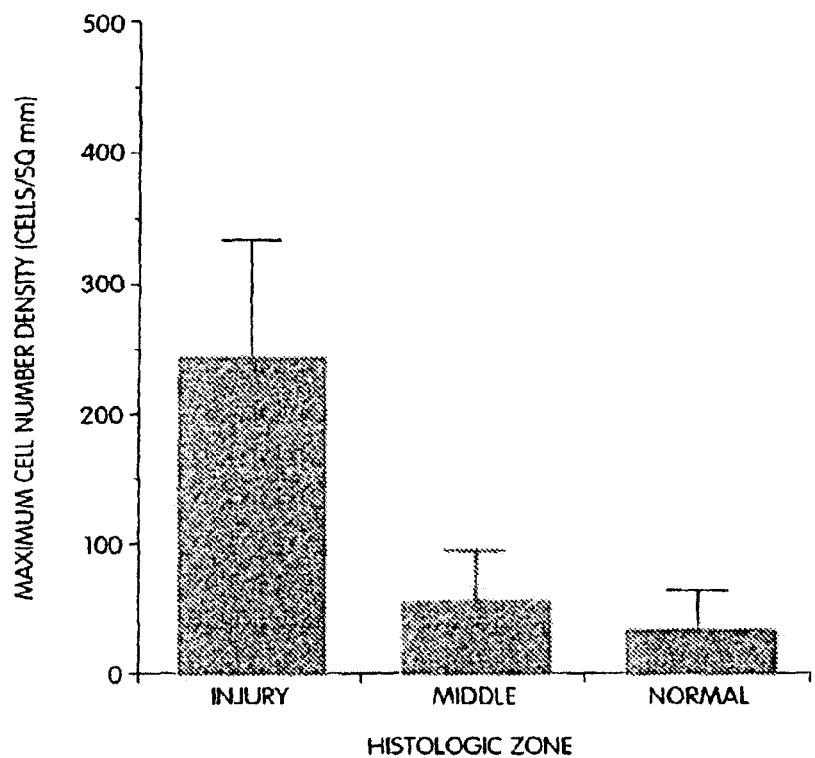
FIG. 16 is a histogram of the maximum cell number density in the collagen-glycosaminoglycan template as a function of explant harvest location (values are mean±SEM).

3-D Culture Outgrowth. In the constructs with interposed collagen-glycosaminoglycan scaffolding, fibroblasts migrated from the human anterior cruciate ligament explants into the templates at the earliest time point (1 week). At one week, migration into the templates was seen in 4 of 4 of the templates cultured with explants from the injury zone, 1 of 4 templates cultured with explants from the middle zone, and 1 of 4 of the templates cultured with explants from the normal zone. By four weeks, cells were seen in 3 of 3 templates cultured with the injury zone explants (the fourth template had been completely degraded) and in 3 of four of the templates cultured with the normal zone explants. Five of the explants completely degraded the template prior to the collection time. The location from which the explants were taken (injury, middle or normal) was found to have a statistically significant effect on the cell number density in the template (two way ANOVA, p=0.001), with Bonferroni-Dunn post-hoc testing demonstrating differences between templates cultured with explants from the injury zone and middle zone (p=0.009) and the injury and normal zone (p=0.003; FIG. 16). The difference between the template cell density for templates cultured with explants from the middle and tibial of the twelve explants (three from the injury zone, two from the middle zone, and two from the normal zone) demonstrated confluent growth for at least two consecutive time periods prior to termination and were included in the calculation of the average rate. All explanted tissue and fibroblasts on the culture wells were fixed in formalin after four weeks in culture.

Fascicular-collagen-glycosaminoglycan Template Constructs. One fascicle from each of the 4 patients was divided into explants for use in the test (injury zone or middle zone and template) and control (normal zone and template) groups. This yielded two test and one control construct per patient for examination after 1, 2, 3, and 4 weeks in culture, providing eight test and four control constructs at each of the four time points.

The forty-eight constructs were made by placing the ligament explant onto a 9 mm disc of collagen-glycosaminoglycan (CG) template (FIG. 15). All of the constructs were cultured in media containing Dulbecco's DMEMI F12 with 10% fetal bovine serum, 2% penicillin streptomycin, 1% amphotericin B, 1% L-glutamine and 2% ascorbic acid. Media was changed 3× a week. The diameter of the template was measured at each media change. Six templates without explants were cultured simultaneously and measured at each time change as controls.

One construct from the injury, middle and normal zones from each patient (n=4) were fixed and histologically examined after 1, 2, 3 and 4 weeks in culture. Two of the constructs at three weeks showed signs of low-grade infection and were excluded from the EXAMPLE. Hematoxylin and eosin staining and immunohistochemical staining for α-sm actin were performed for each construct. Sections were examined using a Vanox-T AH-2 microscope (Olympus, Tokyo, Japan) with normal and polarized light. For each template, areas of 0.1 mm$^2$ (250 by 400 micrometers) were counted, and the highest cell number within that area recorded as the maximum cell number density. This value was multiplied by 10 to obtain the number of cells per square millimeter. The fascicular tissue and collagen-glycosaminoglycan scaffolding were examined using polarized light to determine the degree of crimp and collagen alignment.

This EXAMPLE demonstrated that the cells intrinsic to the ruptured human anterior cruciate ligament were able to migrate into a regeneration template, eventually attaining small areas with cell number densities similar to that seen in the human anterior cruciate ligament in vivo. Explants from the transected region demonstrated outgrowth onto a 2-D surface with a linear increase in outgrowth radius as a function of time in culture. Cells which migrated into the collagen-glycosaminoglycan scaffold differed significantly from the populations of the ruptured anterior cruciate ligament in that while an average of 2 to 20% of cells are positive for α-sm actin in the ruptured anterior cruciate ligament, 100% of cells noted to migrate at the early time periods were positive for this actin isoform.

The investigation in this EXAMPLE implemented an in vitro model that allows for the investigation of the migration of cells directly from an explant into a 3-D collagen-glycosaminoglycan scaffold. Cells with all three previously described ligament fibroblast morphologies—fusiform, ovoid and spheroid—were noted to migrate into the scaffold. Location in the ligament from which the explant was obtained was found to significantly effect the cell number density in the template, with higher number densities of cells found to migrate from the injury zone of the ligament. These findings suggest that cells intrinsic to the human anterior cruciate ligament are capable of migrating from their native extracellular matrix onto an adjacent collagen-glycosaminoglycan scaffold, and that the zone of injury contains cells in which are capable of populating a regeneration template in greater numbers than the middle and normal zones of the ruptured ligament.

The outgrowth rates noted for the explants from ruptured ligaments was found to be about 0.25 mm/day. However, the average time to outgrowth was four days shorter for the ruptured anterior cruciate ligament explants (6.6±2.0 days) than that reported for the intact anterior cruciate ligament explants (10±3 days) (Murray et al., 17 (1) J. Orthop. Res. 18-27 (1999)).

The cellular response to injury appears to be the appropriate one in the anterior cruciate ligament; however, no regeneration of the tissue in the gap between ruptured ends is noted. Previous investigators have demonstrated that coagulation of blood does not occur in the intrasynovial environment. As the initial phase of healing in extra-articular tissues involves formation of a blood clot which re-connects the ruptured ends of the ligament, one hypothesis for the lack of healing of the anterior cruciate ligament after injury may be the lack of formation of a provisional scaffolding due to the coagulation defect in the knee. Therefore, use of a bioengineered substitute for the provisional blood clot may facilitate the healing of the intra-articular anterior cruciate ligament.

Conclusions. Cells from the human anterior cruciate ligament are capable of migrating into an adjacent regeneration template in vitro. Cells migrate in the greatest density from the zone nearest the site of rupture, or injury zone when compared with tissue taken far from the site of injury. This suggests the approach of developing a ligament regeneration template, or "bridge", which reconnects the ruptured ligament ends, may be successful in facilitating ligament regeneration after rupture. The potential advantages of this approach over anterior cruciate ligament reconstruction include preservation of the proprioceptive innervation of the anterior cruciate ligament, retention of the complex shape and footprints of the anterior cruciate ligament, and restoration of the pre-injury knee mechanics. Successful regeneration of the anterior cruciate ligament may lead to similar advances for meniscal and cartilage regeneration after injury.

This EXAMPLE shows the potential of cells from the ruptured human anterior cruciate ligament fibroblasts to migrate into collagen-glycosaminoglycan templates that may ultimately be used to facilitate regeneration anterior cruciate ligament after rupture. The model used here allows for the analysis of the migration of fibroblasts out of human tissues directly onto a porous 3-D scaffold in a controlled, in vitro, environment. This construct obviates several possible confounding factors, such as modulation of cell phenotype, which may occur during cell extraction or 2-D cell culture.

EXAMPLE 11

Effects of Location in the Human ACL on Cellular Outgrowth and Response to TGF-β1 In Vitro The purpose of this EXAMPLE was to determine how cells in selected locations in the human anterior cruciate ligament varied in certain behavior that might affect their potential for repair. Specifically, in this EXAMPLE the outgrowth of cells in vitro from explants different locations in the anterior cruciate ligament, at two concentrations of fetal bovine serum (FBS) and three concentrations of TGF-β1 were measured.

Methods. Fifteen intact human anterior cruciate ligaments were retrieved from patients undergoing TKA. The ligaments were cut transversely into four 2-3 mm thick sections. Each section was divided into six explants, two of which were reserved for histological analysis and four of which were placed in 2-D culture wells. Explants from the proximal and distal sections were cultured in 10% FBS, 0.5% FBS, and 0.5% FBS with 006 ng/ml. TGF-β1, 0.6 ng/ml TGF-β1, and 6 ng/ml TGF-β1. Media were changed 3× a week, and cell outgrowth area measured at each medium change. Cultures were terminated after four weeks.

Figure 17:
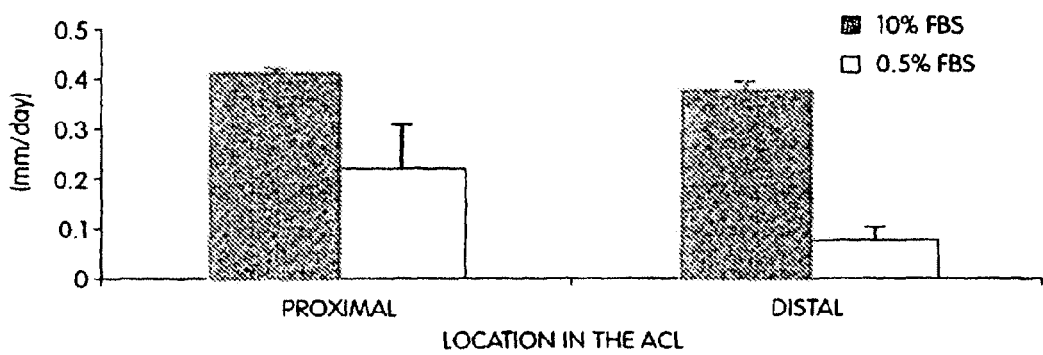
FIG. 17 is a histogram of the effect of location on outgrowth rate for high and low serum concentration.
Figure 18:
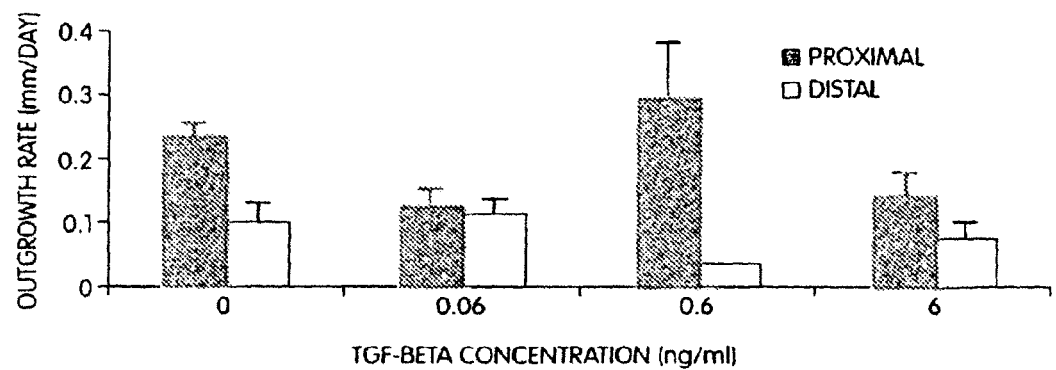
FIG. 18 is a histogram for outgrowth rates from human anterior cruciate ligament explants as a function of location and TGF-β concentration.

Results. Explants taken from the proximal anterior cruciate ligament differed significantly in their outgrowth behavior from those taken from the distal anterior cruciate ligament. In the 10% FBS group, there was a significant effect of location on the time to initial contiguous outgrowth (ANOVA, p=0.03). There was, however, no effect of location on the rate of outgrowth (ANOVA, p=0.14). In contrast, in the 0.5% FBS group the rates of outgrowth were different with a higher outgrowth rate seen in the proximal explants (ANOVA, p=0.01; FIG. 17). This was most pronounced in the groups treated with 0.6 ng/ml of TGF-β1 (FIG. 18). Results of histological analysis of longitudinal sections of the ligaments were consistent with previous observations of higher cell densities and nuclear aspect ratios in the proximal anterior cruciate ligament. No correlation was found between the explant outgrowth rate and the cell number density ($r^2$=0.04) or the predominant nuclear morphology ($r^2$=0.11).

Discussion. This EXAMPLE demonstrates that explants taken from proximal and distal sites in human anterior cruciate ligament respond differently to low-serum conditions, as well as to the addition of TGF-β1. Because these differences do not correlate with the cell number density or nuclear morphology, other features of the cellular heterogeneity and fibroblast phenotype within the human anterior cruciate ligament may be associated with the differences in cell behavior.

EXAMPLE 12

The Effect of Gender and Exogenous Estrogen on the Histology of the Human Anterior Cruciate Ligament The purpose of this EXAMPLE is to determine if any histological differences are present between the anterior cruciate ligament in women and men. Another objective of this EXAMPLE was to determine if exogenous estrogen had any significant effect on the measured parameters by examining ligaments from two groups of women, those on and off estrogen replacement therapy.

Methods. Intact anterior cruciate ligaments were obtained from 22 patients undergoing total knee arthroplasty. Patients with rheumatoid arthritis or on non-steroidal anti-inflammatory medication were excluded from the EXAMPLE. Nine ligaments were obtained from men (ages 61 to 81, mean age 71), seven from postmenopausal women (ages 51 to 83, mean age 69), and six from postmenopausal women on estrogen replacement therapy (ERT; ages 56 to 87, mean age 68). All ligaments were fixed in formalin, embedded in paraffin, and 7 micrometer sections cut. Routine staining, as well as immunohistochemistry for the α-sm actin isoform, was performed. Histomorphometry was performed on all ligaments, with analysis performed at the proximal edge of the ligament, and 1 mm, 2 mm, 4 mm and 6 mm from the proximal edge. At each location, three 0.1 mm$^2$ areas were analyzed for total cell number, nuclear morphology, and percentage of cells staining positive for α-sm actin. The number of blood vessels at each site was counted and divided by the width of the section at that point to yield a "blood vessel density." Two-way ANOVA and unpaired Student t testing were used to determine the statistical significance of differences among groups.

Results. Two-way ANOVA revealed a significant effect of location on cell number density (p=0.002). While the cell density of the anterior cruciate ligament was higher in women than in men at all sites, ANOVA yielded a p value greater than 0.05 (p>0.07). Unpaired Student t testing of cell densities at the proximal edge of the ligament, adjacent to the femoral insertion, and at 1 mm from the proximal edge gave a value of p=0.05 for gender differences. Further distally in the ligament, the differences between men and women were not statistically significant (p>0.10). There was no statistically significant difference in cell density between those women on ERT and those not on estrogen replacement therapy (p=0.36). Age was not found to have a significant effect on the cell number density. Although women had a higher blood vessel density in the proximal region, this difference was not found to be statistically significant. No statistically significant differences were found in the nuclear morphology or the percentage of α-sm actin positive staining cells in the ligaments.

Discussion. This EXAMPLE demonstrates that the histology of the human anterior cruciate ligament is similar in men and women, with the exception of the cell number density in the proximal region, which is higher in women than men. This EXAMPLE also demonstrates that exogenous estrogen does not have an effect on cell number density, blood vessel density, cell nuclear morphology, or presence of α-sm actin.

EXAMPLE 13

The Cellular Response to Injury in the Human Anterior Cruciate Ligament

This EXAMPLE was performed to determine if two of the biologic responses required for regeneration of tissue, namely revascularization and fibroblast proliferation, occur in the human anterior cruciate ligament after injury.

Materials and methods. 23 ruptured anterior cruciate ligament remnants were obtained from patients (ages 20 to 46, avg. 31 years) at anterior cruciate ligament reconstruction between 10 days and 2 years after rupture. Ten intact ligaments were obtained from patients (ages 57 to 83, avg. 69 years) at TKA. Longitudinal sections were stained with a monoclonal antibody for alpha-smooth muscle actin (α-sm). Histomorphometric analysis was used to determine the distribution of cell number density, blood vessel density, nuclear aspect ratio and the percentage of α-sm positive cells. Two-way ANOVA and Bonferroni-Dunn post-hoc testing determined statistical significance.

Results. No bridging clot or tissue was noted grossly between the femoral and tibial remnants for any of the ruptured ligaments. Four progressive phases of response were seen:

Phase I. Inflammation. Inflammatory cells, dilated arterioles and intimal hyperplasia was seen between 1 and 3 weeks after rupture. Loss of the regular crimp pattern was noted near the site of injury, but maintained 4-6 mm from the site of injury.

Phase II. Epiligamentous regeneration. Growth of epiligamentous tissue over the ruptured end of the ligament remnant was noted between 3 and 8 weeks. Histologically, this phase was characterized by an unchanging blood vessel density and cell number density within the remnant.

Phase III. Proliferation. Between 8 and 20 weeks after rupture, a marked increase in cell number density and blood vessel density within the ligament remnant was noted. Vascular endothelial capillary buds were noted to appear at the beginning of this phase, and loops from anastomoses of proximal sprouts began to form a diffuse network of immature capillaries.

Phase IV. Remodeling and Maturation. After one year from ligament rupture, the ligament ends were dense and white. Histologically, the fibroblast nuclei were increasingly uniform in shape and orientation. Decreased cell number density and blood vessel density were seen during this phase, to a level similar to that seen in the intact human anterior cruciate ligament s.

Cell number density in the ligament after rupture was dependent on time after injury and distance from the injury site. The cell number density within the ligament remnant peaked at 16 to 20 weeks ($p<0.005$), and was highest near the site of injury at all time points. Blood vessel density was dependent on time after injury, with a peak at 16 to 20 weeks ($p<0.003$). Cells staining positive for the contractile actin isoform, $\alpha$-sm, were present throughout the intact and ruptured anterior cruciate ligaments, but were not significantly effected by time after injury.

EXAMPLE 14

Effects of Growth Factors and Collagen-Based Substrates the Fibroinductive Properties of Fibroblast Migration The purpose of this EXAMPLE is to determine the process of fibroblast-mediated connective tissue healing and how specific alterations in the extracellular environment alter this process. We quantify the effects of 4 different growth factors and 4 collagen based substrates on features associated with the repair processes in connective tissues which successfully heal. These processes are the fibroinductive properties of fibroblast migration, proliferation, and type I, type II, and type III collagen synthesis. We also define the effects of environmental modifications on the expression of a contractile actin isoform, $\alpha$-smooth muscle actin ($\alpha$-sm).

In EXAMPLE 3, we demonstrated that fibroblasts in the ruptured anterior cruciate ligament are able to migrate from their native extracellular matrix into a 3-D CG scaffold in vitro. This EXAMPLE provides improved rates of migration, proliferation, and type I collagen synthesis of anterior cruciate ligament fibroblasts by altering the degree and type of cross-linking of the scaffold and by adding four different growth factors to the scaffold. The specific aims for this EXAMPLE are (1) to determine the effect of cross-linking of a collagen-based scaffold on (a) the rate of fibroblast migration, (b) the rate of fibroblast proliferation, (c) expression of a contractile actin, and (d) the rate of type I collagen synthesis by fibroblasts in the collagen-based scaffold, and (2) to determine the effect of addition of selected growth factors on these same outcome variables. Thus, this EXAMPLE determines how specific alterations in scaffold cross-linking and the addition of specific growth factors alter the fibroinductive properties of a collagen based scaffold. In this EXAMPLE, the fibroinductive potential of the scaffold is defined as its ability to promote fibroblast infiltration, proliferation and type I collagen synthesis.

The following two hypotheses relate to the specific aims listed above:

The method and degree of cross-linking alter the rate of fibroblast migration from an anterior cruciate ligament explant into a collagen-based scaffold as well as the rate of fibroblast proliferation, expression of a contractile actin, and type I collagen synthesis within the scaffold. The rationale for this hypothesis is the EXAMPLES above, which demonstrated that alteration in fibroblast proliferation rates and expression of the contractile actin isoform after fibroblast seeding of cross-linked scaffolds, as well as the differences in rates of collagen synthesis by chondrocytes seeded into type I and type II collagen based scaffolds. One possible mechanism for this observation is that the solubilized fragments of collagen resulting from the degradation of the collagen-based scaffold could affect cell metabolism. These fragments may form at different rates for different cross-linking methods. Validation of this mechanism demonstrates that the fibroinductive properties of the collagen-based scaffold can be regulated by the choice of cross-linking method.

In this EXAMPLE, constructs of human anterior cruciate ligament explants and cross-linked collagen-based scaffolds are used to determine the rates of cell migration, proliferation, expression of a contractile actin and type I collagen synthesis. Scaffolds cross-linked with glutaraldehyde, ethanol, ultraviolet light and dehydrothermal treatment are used. We correlate cross-linking method with the regulation of the fibroinductive properties of the scaffold.

(2) The addition of growth factors to the CG scaffold alters the rates of fibroblast migration from an anterior cruciate ligament explant to a collagen-based scaffold as well as the rates of fibroblast proliferation, expression of a contractile actin, and type I collagen synthesis within the scaffold. The rationale for this hypothesis is the alteration in fibroblast migration rates onto 2-D surfaces and synthesis of type I collagen in vitro when growth factors are added to the culture media, as well as alteration in rates of incisional wound healing with the addition of growth factors. Validation of this hypothesis shows how the fibroinductive properties of the collagen-based scaffold may be regulated by the addition of a specific growth factor.

The growth factors to be studied in this EXAMPLE include TGF-$\beta$, EGF, bFGF and PDGF-AB. Constructs of human anterior cruciate ligament explants and collagen-based scaffolds cultured in media containing growth factors are used to determine the rates of cell migration, proliferation, expression of a contractile actin and type I collagen synthesis in these constructs. The control wells contain only 0.5% fetal bovine serum, a protocol which has been reported previously by DesRosiers et al., 14 J. Orthop. Res. 200-208 (1996). We correlate growth factor presence with the regulation of the fibroinductive properties of the scaffold.

Assay design. The assay design is similar to that of EXAMPLE 4. Human anterior cruciate ligament explants are obtained from patients undergoing total knee arthroplasty. Ligaments which are grossly disrupted or demonstrate gross signs of fatty degeneration are excluded from the analysis. A fairly uniform distribution of cells occurs in the distal ⅔ of the ligament fascicles, so this section is used for all assays. The preparation of the collagen-based scaffold is as described in EXAMPLE 4 and previously reported by Torres, *Effects Of Modulus Of Elasticity Of Collagen Sponges On Their Cell-Mediated Contraction In Vitro* (M.S. Thesis Massachusetts Institute of Technology, 1998) (on file with the MIT Library). The cross-linking of the scaffolds is as described in EXAMPLE 4 and as previously described by Torres, *Effects Of Modulus Of Elasticity Of Collagen Sponges On Their Cell-Mediated Contraction In Vitro* (M.S. Thesis Massachusetts Institute of Technology, 1998) (on file with the MIT Library). The growth factors are added to the cell culture media as described in EXAMPLE 4. Culture, histology for analysis of cell migration, DNA assay for cell proliferation, immunohistochemistry for the contractile actin isoform, and SDS-PAGE analysis for the synthesis of type I collagen are as described in EXAMPLE 4. A pilot assay is performed to assess the DNA content with the DHT cross-linked scaffold with the addition of no growth factors. Alternatively, a tritiated thymidine assay can be evaluated or the specimens used for proliferation can be fixed and serially sectioned, with sections at regular intervals examined for cell number density. Maximum number density is recorded for each specimen type. Associated histology is used to estimate the percentage of dead cells.

EXAMPLE 15

Use of a Provisional Scaffold to Encourage Tissue Regeneration

This EXAMPLE uses of a provisional scaffold to encourage tissue regeneration in the gap between the ends of the ruptured anterior cruciate ligament without removal of the ligament. This has the advantages of retaining the complex anterior cruciate ligament geometry and proprioceptive innervation of the ligament.

The objective of this EXAMPLE is to show the in vivo effect of placement of a provisional scaffold between the ruptured ends of the anterior cruciate ligament. A rabbit model is chosen because of its previous establishment as a mechanical and biochemical model for the human anterior cruciate ligament. We have previously shown that homologous cell distributions and vascularity between the human and lapine anterior cruciate ligament (see, EXAMPLE 3). A CG scaffold is chosen as the provisional scaffold, given its success in dermis and tendon and in the human anterior cruciate ligament in vitro model.

The goal of this EXAMPLE is to evaluate a novel method of treatment of anterior cruciate ligament rupture which would facilitate ligament healing and regeneration after complete rupture. The potential advantages of regeneration over reconstruction include retention of the complex footprints of the human anterior cruciate ligament, preservation of the proprioceptive nerve endings within the anterior cruciate ligament tissue, less invasive surgery with no graft harvest required, and maintenance of the complex fascicular structure of the anterior cruciate ligament. Effective, minimally invasive, treatment of anterior cruciate ligament rupture would be particularly beneficial to women engaged in military training, as they are at an especially high risk for this injury.

The problem to be investigated in this EXAMPLE is the development of an implant to be used for anterior cruciate ligament regeneration after complete rupture of the ligament. Loss of the function of the anterior cruciate ligament leads to pain, joint instability and swelling. Left untreated, a knee with instability secondary to anterior cruciate ligament rupture leads to joint degeneration and osteoarthritis.

The objective of this EXAMPLE is to compare immediate primary repair with primary repair and scaffold augmentation in the treatment of anterior cruciate ligament rupture in a rabbit model. The technique of primary repair involves reapproximation of the ruptured ligament ends with sutures passed both through ligament and bone to stabilize the tissue. In this EXAMPLE, we determine whether cellular migration into a gap between ruptured ligament fascicles if a provisional scaffold is provided. Moreover, we determine what type of tissue is being deposited into the gap between fascicles. The specific aim of this EXAMPLE is to evaluate the effect of a provisional collagen sponge-like implant to facilitate anterior cruciate ligament regeneration of the ligament at 3 weeks, 3 months, 6 months, and 1 year after injury, resulting in a change in the relative percentage of various tissue types in the defect.

Military Significance. In a recent study of midshipmen attending the U.S. Naval Academy, the incidence rate of anterior cruciate ligament (ACL) injury was 10 times higher for women than men (Gwinn et al., *Relative gender incidence of anterior cruciate ligament injury at a military service academy*, in 66th Annual Meeting. Anaheim, Calif. (1999)). In military related training, the incidence of anterior cruciate ligament rupture was 6 times higher that in competitive, high risk sports. The study also found that women engaged in military training sustained an anterior cruciate ligament tear 3 times per every 1000 exposures. Thus, for women engaged in military training exercises twice a week, an average of 1 in 4 will sustain an anterior cruciate ligament tear each year (Gwinn et al., *Relative gender incidence of anterior cruciate ligament injury at a military service academy*, in *66th Annual Meeting*, Anaheim, Calif. (1999)). This study, and others, highlight the importance of anterior cruciate ligament rupture in women, particularly women engaged in activities which place them at risk for this injury, such as military training. More than 200,000 people rupture their anterior cruciate ligament annually (*National Center for Health Statistics* (1986)), and the risk of anterior cruciate ligament rupture is significantly higher for women engaged in intercollegiate sports when compared with their male counterparts (Arendt & Dick, 23 (6) Am. J. Sports Med. 649-701 (1995), Stevenson, 18 Iowa Orthop. J. 64-66 (1998)). For many women athletes, anterior cruciate ligament rupture may be a career-ending injury, as many patients can not return to their previous level of activity, even after repair or reconstruction (Marshall et al., 143 Clin Orthop 97-106 (1979); Noyes et al., 68B J. Bone Joint Surg. 1125-1136 (1980)). Development of new methods of treatment of the ruptured anterior cruciate ligament, including ligament regeneration, may lead to quicker recovery times and improved rates of return to high levels of physical training for both women and men.

An anterior cruciate ligament rupture can be a devastating, if not career-ending, injury for women engaged in competitive athletics, and it is likely to be an event of similar magnitude in women in the military engaged in heavy physical activity. Currently, there is no reliable treatment for anterior cruciate ligament rupture which has been shown to slow the progression of osteoarthritis in injured knees. Breakdown of articular cartilage is a source of pain and disability for many people. Left untreated, loss of anterior cruciate ligament function leads to meniscal and chondral injury, and eventually can cause destruction of the entire joint, necessitating total joint replacement. Our biological implant treats the defect in the ruptured anterior cruciate ligament. Such treatment may prevent the progression of joint deterioration seen in anterior cruciate ligament deficient knees, and in knees after anterior cruciate ligament reconstruction. It provides a less invasive method of treatment for this common injury, and potentially retain the complex anatomy and innervation of the anterior cruciate ligament. To facilitate the continuance of women in physically demanding careers, a new method of treatment of anterior cruciate ligament rupture is necessary, one which is minimally invasive, can restore the original structure and function of the anterior cruciate ligament, and has the potential to minimize the progression to premature osteoarthritis.

Experimental Design and Rationale. The following tests are provided to achieve the specific aim. TABLE 7 shows the 3 test groups.

TABLE 7

Test Groups

| Group | Number of Knees | Treatment | Time to Sacrifice |
|---|---|---|---|
| I | 6 | None | 3 weeks |
| I | 6 | None | 3 months |
| I | 6 | None | 6 months |
| I | 6 | None | 12 months |
| II | 6 | Immediate Repair | 3 weeks |
| II | 6 | Immediate Repair | 3 months |
| II | 6 | Immediate Repair | 6 months |
| II | 6 | Immediate Repair | 12 months |
| III | 6 | Immediate Repair + Scaffold | 3 weeks |
| III | 6 | Immediate Repair + Scaffold | 3 months |
| III | 6 | Immediate Repair + Scaffold | 6 months |
| III | 6 | Immediate Repair + Scaffold | 12 months |

Effect of a Collagen Implant on Immediate Primary Repair. All animals have their anterior cruciate ligaments disrupted forcibly by pulling a suture through the ligament until it ruptures. After rupture, 24 of the knees is closed without further treatment for the control group. A second group of 24 knees undergoes immediate primary repair with sutures and a third group of 24 undergoes primary repair with a provisional scaffold placed in the defect between the ruptured ligament ends.

Power calculation for Sample Size. The power calculation for the sample size for the experimental groups is based on detecting a 30% difference in the mean values of total fill, the area percentage of crimped collagenous tissue, and the values of the specific mechanical properties. Assuming a 20% standard deviation, a level of significance of $\alpha=0.05$, for a power of 0.80 ($\beta=0.20$), 6 specimens are required. We assume that a 30% change in the outcome variable would be a meaningful indication of the benefit of one treatment group over the other.

Collagen-glycosaminoglycan (CG) scaffold synthesis. The scaffold used in this EXAMPLE is the same scaffold used in EXAMPLE 3. The 3-D culture substrate is a highly porous CG matrix, composed of type I bovine hide collagen and chondroitin-6-sulfate. This is prepared by freeze-drying the collagen-glycosaminoglycan dispersion under specific freezing conditions (Louie, *Effect of a porous collagen-glyosaminoglycan copolymer on early tendon healing in a novel animal model* (Ph.D. Thesis Massachusetts Institute of Technology 1997) (on file with the MIT Library)). The average pore size of the CG scaffold manufactured in this manner is 100 µm.

Animal Model. Mature female rabbits, weighing 3 to 5 kg, are used in this EXAMPLE. Prior to operation, the knee joints are examined roentgenographically to exclude animals with degenerative joint disease. All operations are performed under general anesthesia and sterile conditions. A No. 5 Ethibond suture is passed behind the anterior cruciate ligament and the ligament ruptured in its proximal third by forcibly pulling the suture forward while holding the knee immobilized. This mechanism of induced rupture provides a more realistic, "mop-end" ruptured tissue than transection with a blade. No attempt is made to debride the ligament remnant of synovial tissue. Before closing the capsule, bleeding vessels is clamped and cauterized. The knee joint is closed in layers. Animals have surgery on only one limb to allow for protective weight bearing in the post-op period. No post-operative immobilization is used.

The knees undergoing primary repair have a 2-0 Vicryl suture placed through each end of the ruptured ligament. The suture through the tibial remnant is then passed through the distal femur, and the suture through the femoral component passed through the tibia as described in Marshall's technique for primary repair (Marshall et al., 143 Clin Orthop 97-106 (1979).

Knees undergoing primary repair with the placement of the scaffold in the defect between ruptured ligament ends have sutures placed in an identical manner to that in the primary repair group. The CG scaffold is placed into the defect prior to tensioning of the sutures.

Method of Histomorphometric Evaluation. At the time of sacrifice, the skin is removed from the knee joint, and the a capsulotomy performed on the lateral side of the knee, adjacent to the patellar tendon, to allow adequate penetration of the joint by the fixative solution. After formalin fixation, the knee joints are immersed in 15% disodium ethylenediamine tetraacetate decalcifying solution, pH 7.4. The specimens are placed on a shaker at 4° C. with three changes of the decalcifying solution each week for approximately four weeks. Samples are rinsed thoroughly, dehydrated, and embedded in paraffin at 60 degrees Celsius. Seven-micrometer thick sections are stained with hematoxylin and eosin and Masson's trichrome. Selected paraffin sections are stained with antibodies to Type I and Type III collagen.

The specific tissue types filling the defect are determined by evaluating the percentage of the area of the central section through the defect occupied by each tissue type: (1) dense, crimped collagenous tissue, (2) dense, unorganized collagenous tissue, (3) synovial tissue, and (4) no tissue. Cell number density, blood vessel density and nuclear morphology of the fibroblasts are determined at each point along the length of the ruptured ligament.

Radiographic Analysis. All knees have anteroposterior and lateral x-rays taken pre-operatively to assess for the presence of degenerative joint disease. Any animals demonstrating degenerative joint disease are disqualified from the analysis. At the time of sacrifice, all knees are radiographed a second time to assess the development of radiographic changes consistent with degenerative joint disease. Correlation between radiographic findings and histologic changes in the articular cartilage of the knee is made.

EXAMPLE 16

Testing of the Biological Implant of the Invention

The biologic replacement for fibrin clot for intra-articular use of the invention is prepared and analyzed, such as is set forth in *Guidance Document For Testing Biodegradable Polymer Implant Devices*, Division of General and Restorative Devices, Center for Devices and Radiological Health, U.S. Food and Drug Administration (Apr. 20, 1996) and *Draft Guidance Document For the Preparation of Premarket Notification [510(K)] Applications For Orthopedic Devices*. U.S. Food and Drug Administration (Jul. 16, 1997).

The composition and material structure (e.g., phases, reinforcement, matrix, coating) of the biologic replacement of the invention to be implanted is characterized quantitatively. These analyses can include the following:

Composition and molecular structure: (a) main ingredients (such as collagen and glycosaminoglycan); (b) trace elements (e.g., heavy metals are low); (c) catalysts; (d) low molecular weight (MW) components (separate components which have and have not chemically reacted with the polymer, e.g., crosslinking agents); (e) polymer stereoregularity and monomer optical purity (if the monomer is optically active; not applicable for collagen or glycosaminoglycan); (f) polydispersity, (g) number average molecular weight ($M_n$) (h) weight average molecular weight ($M_w$); (i) molecular weight distribution (MWD); (j) intrinsic (or inherent) viscosity (specify solvent, concentrations and temperature; not applicable for collagen or glycosaminoglycan); (k) whether the polymer is linear, crosslinked or branched (l) copolymer conversion (e.g., block, random, graft; not applicable for collagen or glycosaminoglycan); and (m) polymer blending. For the molecular weight, the inherent viscosity (logarithmic viscosity number) or some other justifiable method (e.g., GPC) is measured prior to placement of samples in the physiological solution. Samples are removed from immersion and loading at specified time periods throughout the duration of the test and tested for inherent viscosity. Dilution ratio in g/ml is noted.

Morphology (supermolecular structure): (a) % crystallinity; (b) orientation of phases/macromolecules; and (c) types and amounts of phases.

Composite structure: (a) laminate structure; (b) thickness of each ply; (c) number of plies; (d) orientation and stacking sequence of plies; (e) symmetry of the layup; (f) position of reinforcement within the matrix; (g) location within the part; (h) 3 dimensional orientation; (i) fiber density (e.g., distance between reinforcement components or reinforcement matrix volume and weight ratios); (j) fiber contacts and cross-overs per mm; (k) reinforcement structure; (l) cross-sectional shape (m) surface texture and treatment; (n) dimensions; (o) fiber twist; (p) denier; (q) weave; (r) coating; (s) total number of coating layers; (t) thickness of each layer; (u) voids; (v) mean volume percent; (w) interconnections; (x) penetration depth and profile; and (y) drawing or photographs of the product illustrating the position of the coating and any variation in coating thickness (for example, see, FIGS.) The anatomical location and attachment mechanism for the biological implant of the invention is provided in diagrams, illustrations, or photographs of the implant in situ.

Physical properties: (a) dimensional changes of the material as a function of time; (b) densities of reinforcement, matrix and composite; (c) mass of the smallest and largest sizes; (d) roughness of all surfaces; (e) surface area of the smallest and largest sizes; (f) dimensioned engineering drawings of any nonrandom surface structure patterns (e.g., machined structures). Mechanical properties are important because they determine whether the fracture site is adequately fixed to avoid loosening, motion and nonunion. Weight loss and inherent viscosity measurements may be helpful in screening different materials and in understanding degradation mechanisms, though they may not directly address the mechanical properties of the device. For weight loss testing, test samples are weighed to an accuracy of 0.1% of the total sample weight prior to placement in the physiological solution. Upon completion of the specified immersion/loading time, each sample is removed and dried to a constant weight. Drying conditions may include enclosure in a desiccator at standard temperature and pressure, use of a partial vacuum or the use of elevated temperatures. The weight is recorded to an accuracy of 0.1% of the original total sample weight. Elevated temperatures can be used for drying of the sample provided that the temperature used does not change the sample (such as for collagen and glycosaminoglycan). The drying conditions used to achieve a constant weight are noted.

Thermal properties (not applicable for collagen and glycosaminoglycan): (a) crystallization temperature; (b) glass transition temperature; and (c) melting temperature.

Strength retention testing. In an in vitro degradation (or strength retention) test, samples are placed under a load in a physiologic solution at 37° C. Samples are periodically removed and tested for various material and mechanical properties at specified intervals (typically 1, 3, 6, 12, 26, 52, and 104 weeks) until strength has dropped below 20% of the initial strength.

Various test solutions can be used. For example, bovine serum or PBS solution in a volume at least 20 times the volume of the test sample may be used. The pH of the solution approximates the pH of a physiologic environment (about 7.4). Samples are discarded if the measured pH is outside the specified value of more than ±0.2. Each sampling container should be sealable against solution loss by evaporation. Each test specimen is kept in separate containers and isolated from other specimens to avoid cross contamination of degradation byproducts. The solution is kept sterile and properly buffered or changed periodically.

Samples are fully immersed in the physiological solution at 37° C. for the specified period of time. One group of samples are stressed during the entire time in solution to simulate clinical worst case conditions, while another group of samples are set-up in the same environment, without stressing. The amount of sample agitation, solution flow past test specimens, frequency that the solution is replaced, and the clinical significance of these factors are recorded and analyzed.

In vitro degradation rates are compared to the in vivo degradation rates so the in vitro test results can be extrapolated to clinical conditions. Samples are implanted in an animal model and mechanically tested to determine if there are any significant difference in the outcome of test samples degraded in vitro and in vivo. The degradation of the mechanical properties of the test device is compared to a device known in the art. The biological replacement of the invention is compared for the determination of substantial equivalence to a device such as is known in the art (see, BACKGROUND OF THE INVENTION). A comparison of the similarities and differences of the known device to the biological replacement of the invention is made in terms of design, materials, intended use, etc. Both devices are implanted either at the site of actual loaded use (for example, the anterior cruciate ligament) or at a nearby site. A range of healing time for the indicated repair is provided from the literature (see, BACKGROUND OF THE INVENTION). The implantation time should be at least twice as long the longest time over which healing of the repair is expected to occur. Data for this set of tests may be from the same animals used in other tests.

For mechanical testing, the degradation of the mechanical properties of the biological replacement of the invention over time is compared to the same changes for a device known in the art. The degradation values are validated to in vivo results. At time period throughout the duration of the immersion/loading time, samples are removed and tested. Samples are tested in a non-dried or 'wet' condition.

(8) Biocompatibility: The biologic replacement of the invention is tested for biological response in an appropriate animal model. As part of the analysis, the degradation byproducts and their metabolic pathways are identified.

In vivo strength of repair studies compare the mechanical strength of intact tissue to that of a tissue repaired using the biological implant of the invention or a device known in the art. A range of healing times for the indicated repair is provided from the literature (see, BACKGROUND OF THE INVENTION). The implantation time are at least twice as long the longest time over which healing of the repair is expected to occur. A histological analysis of biocompatibility at the implant site determines the tissue response, normal and abnormal, to the presence of the biologic replacement of the invention and its breakdown products. The biologic replacement of the invention is implanted into an animal model such that it experiences loading.

(9) Sterilization information: See the Sterility Review Guidance. U.S. Food & Drug Administration (Jul. 3, 1997). The sterilization method that was used [radiation, steam, EtO] is provided. If the sterilization method is radiation, then the radiation dose that was used is provided. If the sterilization method is EtO, then the maximum residual levels of ethylene oxide, ethylene chlorohydrin and ethylene glycol that were met is provided. These levels are below those limits proposed in the Federal Register FR-27482 (Jun. 23, 1978).

(10) Shelf life: The shelf-life of the final biologic replacement is determined.

EXAMPLE 17

Human Anterior Cruciate Ligament Cell Growth in Acid-Soluble Collagen Hydrogel

Figures 20A, 20B:
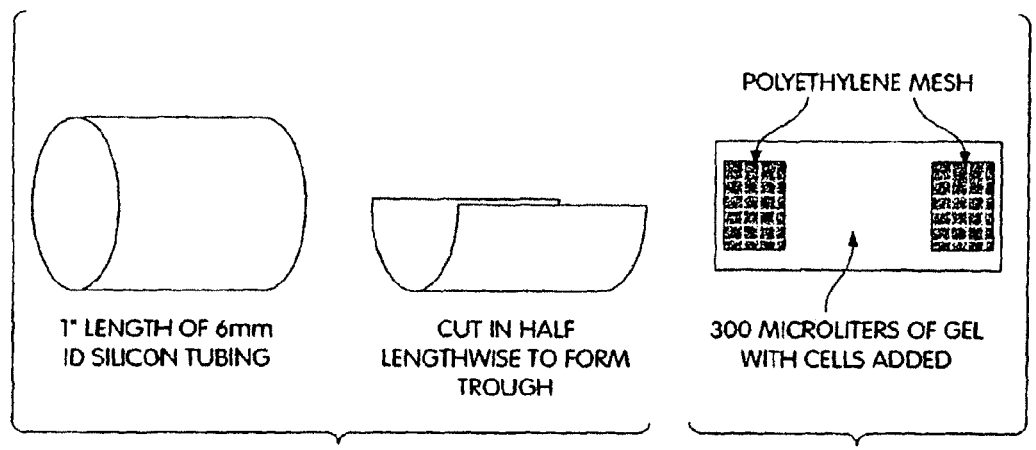
FIGS. 20A and 20B are drawings illustrating preparation of the molds.
Figure 21A:
FIGS. 21A-21D are photomicrographs of the collagen gel with human ACL cells demonstrating increasing cell number density and increasing cellular alignment with time in culture. All micrographs are at 200×.
Figure 21B:
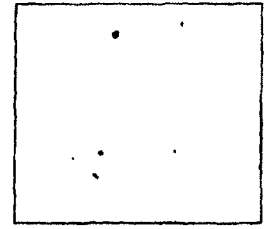
Figure 21C:
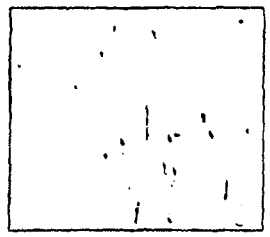
Figure 21D:
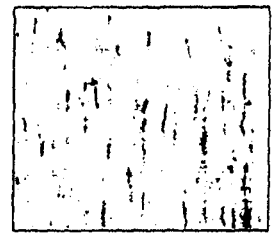

The ability of cells of the human anterior cruciate ligament to survive in a collagen hydrogel was assesed. Human anterior cruciate ligament was obtained from a patient undergoing total knee arthroplasty. The ligament was sectioned into 18 explants, each 1-2 mm on a side. The explants were then cultured in a 6 well plate with 1.5 cc of media/well containing high-glucose DMEM, 10% FBS and antibiotics. Media were changed three times a week. After four weeks of culture, the tissue was removed and the cells which had grown out of the tissue onto the plate were trypsinized, counted ($1 \times 10^7$ cells) and placed into two 75 cm$^2$ flasks overnight. On the second day, the gel components were assembled. All ingredients were kept on ice until placed into the molds. The molds were made by cutting 6 mm ID silicon tubing into 1 inch lengths, then cutting each tube in half to make a trough. Silicon adhesive was then used to secure a piece of polyethylene mesh to each end of the trough (FIG. 20). The adhesive was allowed to cure overnight, then sterilized by placing into sterile 70% EtOH for 2 hours. The molds were exhaustively rinsed in dIH20 and placed individually into 6 well plates prior to adding the gel. Prior to gel assembly, the cells were again trypsinized and centrifuged. The media was aspirated, leaving a pellet of cells in a 15 cc centrifuge tube. The gel was made by mixing 3.5 cc of acid-soluble, Type I collagen (Cell-A-Gen 0.5%, ICN Pharmaceuticals) with 1 cc of 10× Ham's F10, 1 cc of PCN/Strep, 0.1 ml Fungizone, 3 microliters of bFGF and 3.7 ml of sterile, distilled water. The above mixture was vortexed, and 1.4 ml of Matrigel added. The mixture was vortexed again, and then 0.155 cc of 7.5% NaOH was added. The mixture was vortexed, and added to the tube containing the cell pellet. The cells were resuspended in the cold gel by gentle mixing with a 1 cc pipette. The gel-cell mixture was then aliquoted into the molds, with 300 µl used in each mold. A drop of the gel-cell mixture was also placed into the bottom of each well to monitor cell survival in the gel. The constructs were allowed to sit at room temperature for 30 minutes, then moved to the 37 degree incubator for 30 minutes. After 1 hour, media containing 10% FBS was added to cover the mold and gel. Constructs were sacrificed for histology at 3 hours, 3 days and 9 days. The gels were fixed in cold paraformaldehyde for 4 hours, then stored in PBS. The gels were embedded in paraffin and 7 micrometer sections cut. Serial sections were stained with hematoxylin and eosin and Masson's trichrome.

On the second day of culture, the cells were noted to be growing in the gel on the bottom of each well, and in the gel constructs (using an inverted phase microscope). The gel had assumed an hourglass shape. This shape became more pronounced with time in culture. Staining of the gels demonstrated increasing cell numbers within the gel with time (FIG. 21), as well as increasing alignment of the cells along the longitudinal axis of the gel (with the cell processes pointing toward each end of the neo-ligament). By 9 days of culture, the gel constructs had a histologic appearance similar to that of the intact human ACL in terms of cell density and alignment (FIG. 21).

These data demonstrate that acid-soluble collagen hydrogel is conducive to ACL cell growth and proliferation.

EXAMPLE 18

Figure 22:
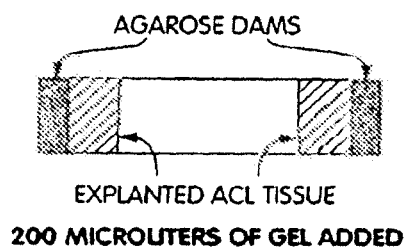
FIG. 22 is a drawing illustrating the position of the explanted ACL tissue in the mold.

Human Anterior Cruciate Ligament Cell Mediated Contraction of Acid-Soluble Collagen Hydrogel The ability of endogenous or exogenous human anterior cruciate ligments cells to mediate collagen hydrogel contraction was assessed. Human ACL explants were cultured as in EXAMPLE 17 to obtain primary outgrowth human ACL cells. The cells were trypsinized from 9 wells (1.5 plates, approx $6 \times 10^6$ cells), and collected in a pellet as in Experiment 1. Additional explants were obtained from the ACL of a second patient undergoing arthroplasty on Dec. 4, 2000 (the day before the experiment was started.) Explants were 2 mm on each side. The explants were predigested in 0.1% collagenase for 15 minutes at 37 degrees C. and then rinsed exhaustively in sterile PBS and placed in culture media which included 10% FBS. Explants were maintained in culture media at 37 degrees C. and 5% CO2 overnight. The molds were made by sectioning the 6 mm ID silicon tubing in half to make a trough, and sealing the ends of the trough with agarose, which was sterilized by autoclaving. The agarose was melted by placing it in a 80 degree C. water bath, then 1 drop was added to each end of the mold. The molds were sterilized by placing in 70% EtOH for 2 hours, then rinsing exhaustively in sterile H2O. Each mold was placed into individual wells of a 6 well plate. One explant was placed into each end of the trough (FIG. 22). A total of 18 constructs were prepared. Each mold was able to hold 200 microliters of liquid.

The gel was made by mixing 3.5 ml of acid-soluble Type I collagen (Cell-a-gen, 0.5%, ICN Pharmaceuticals), 1 ml of 10× Ham's F12, 1 ml of PCN-Strep, 0.1 ml of Fungizone, 3 microliters of bFGF, 3.7 ml of ddIH20 and 1.4 ml of Matrigel. The mixture was vortexed and 0.155 cc of NaOH added. The mixture was vortexed again and 5 cc added to the cell pellet. The cells were resuspended in 5 cc of the gel, and the remaining 5 cc were reserved for the cell-free gel constructs. Nine constructs were made using the gel with added cells (C group), and nine were made with the cell-free gel (CF group). The explants and gel were cultured for 21 days. Media were changed three times a week, with measurements of the distance between the explants made at each media change. Constructs in each group were sacrificed for histology at days 0, 3, 7, 14 and 21. The constructs used for histology were fixed in 10% neutral buffered formalin for one week, then embedded in paraffin and sectioned at 7 micrometers. Serial sections were stained with hematoxylin and eosin to evaluate cell density and alignment.

Figure 23:
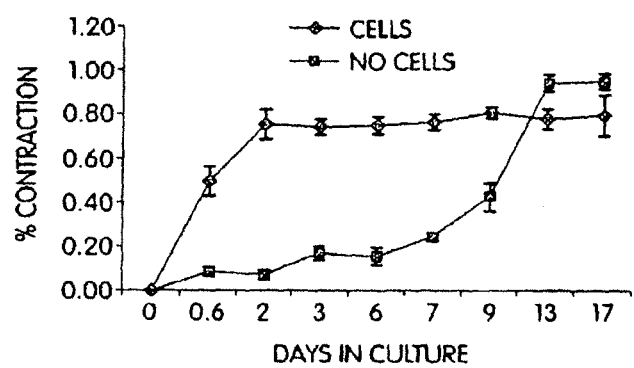
FIG. 23 is a graph illustrating gel contraction with time in the gel with cells and the gel without cells.
Figure 24:
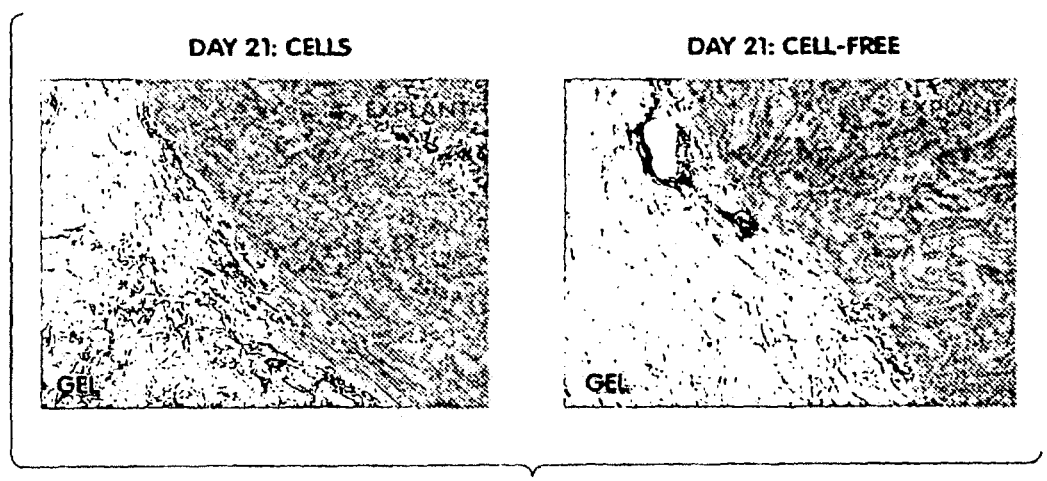
FIG. 24 is a photomicrograph of the interface between the ACL tissue (explant) and the gel in both the cell-gel and the cell-free gel after 21 days in culture.

On day one, the cells were seen in the gel of the cell-gel group, and the gels in this group were noted to already be contracting and drawing the two pieces of ligament tissue closer together (FIG. 23). No cells in the gel, or contraction of the gel was noted in the cell-free group, until 3 days after culture, and at 7 days, cells were seen near the explants in all of the gels in the cell-free group. Contraction of the gels was noted to begin at 7 days after culture in the cell free group (FIG. 23). The histologic analysis demonstrated increasing numbers of cells in both the cell gel and the cell free gel. The increase in the cell-seeded gel may have been due to the proliferation of the seeded cells, or to the migration of cells from the tissue into the gel. The increase in the cell-free gel was from migration of cells from the ligament tissue. By day 21, the cell density in the two groups was similar (FIG. 24).

Cell mediated contraction of the collagen gel is seen whether the cells are seeded into the gel, or whether they migrate in from adjacent tissue. The cell-free gel has a similar density of cells at the interface after three weeks in culture with the ACL explants.

EXAMPLE 19

Platelet Rich Plasma Enhanced Adhesive Properties of the Collagen Hydrogel

To determine the ability of platelet rich plasma to enhance the adhesive properties of the collagen hydrogel four experimental groups were tested.

The four groups tested were:
1. Explant (no predigestion) and gel without cells
2. Explant (collagenase predigestion) and gel without cells
3. Explant (no predigestion) and gel with fibroblasts added
4. Explant (no predigestion) and gel with platelet rich plasma added For each group, an explant was secured at one end of a mold, and polyethylene mesh at the other end. Groups 1, 3 and 4 were cultured for 4 days as in EXAMPLE 18. Group 3 was predigested in 0.1% collagenase for 10 minutes at 37 degrees C., washed in PBS and cultured.

Figure 25:
FIG. 25 is a photograph of a mold with mesh at one end and a needle to secure tissue at the other end.

To fasten the tissue to the mold, 6 well plates were coated with Sylgard. After the Sylgard cured overnight, the wells were sterilized with 70% EtOH for two hours and exhaustively rinsed. The molds were made with silicon adhesive used to secure polyethylene mesh to one end of the trough and then sterilized, as in experiment 1. Each mold was placed into an individual well of a 6-well plate. On the other end of the trough, a 30 gauge needle was placed through the explant, through the mold wall and into the Sylgard to secure the tissue within the mold (FIG. 25). Once the constructs had been made, the three gels were assembled.

For the gel without cells (groups 1 and 2), the gel was prepared as in EXAMPLE 17 and 18. A sterile pipette was used to add 300 microliters of gel to each mold.

For the fibroblast gel (group 3), we trypsinized cells from two 75 cm$^2$ flasks and resuspended these cells in 10 cc of gel prepared as in EXAMPLE 17 and 18

For the platelet rich plasma (PRP) group, two 4.5 cc tubes of blood were drawn from the antecubital vein of a volunteer donor into blue top tubes containing 3.2% Sodium Citrate. The tubes were spun at 700 rpm for 20 minutes. After spinning, 1.4 cc of the platelet-rich plasma upper layer was aspirated from each tube and placed into a sterile microcentrifuge tube. All tubes were stored in the 37 deg C. incubator until use. A 15 microliter aliquot of the PRP was taken and the platelet and WBC density counted. A density of $1.6 \times 10^8$ platelets/ml was determined. Fewer than $4 \times 10^3$ WBCs/ml were found. For the PRP gel, the collagen, PCN/strep, bFGF and Matrigel were mixed. Next, 0.25 ml of 10× Ham's F12 was added to 2.5 cc of this mixture and vortexed. The PRP (1.4 ml at 37 deg C.) was added to the gel components, 0.077 ml of 7.5% NaOH added and the mixture pipetted to mix. The resultant gel was added to each mold for the PRP group.

Figure 26:
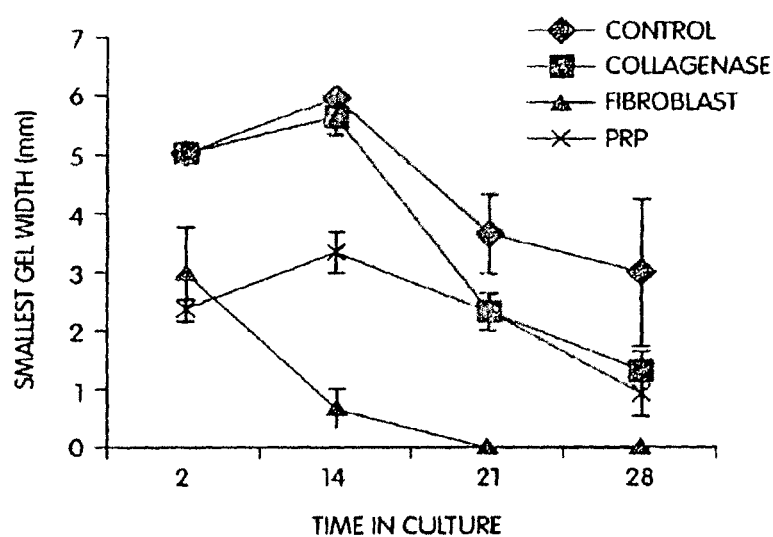
FIG. 26 is a graph illustrating minimum gel widths for the four groups during the four weeks of culture.

The gels were allowed to set for 30 minutes and then 5 cc of media containing 10% FBS was added to each well. Media were changed three times each week. The minimum width of the gels was measured weekly as an estimate of cell-mediated contraction. Constructs from each group were sacrificed for histology at 3 hours, two days, two weeks, three weeks and four weeks of culture. The gel containing the PRP (group 4) demonstrated the fastest set time at setting beginning at 5 minutes, and the gel becoming so thick by 10 minutes that it was impossible to pipette. All gels contracted throughout the experiment (FIG. 26), with the fibroblast seeded gel contracting to the smallest width. However, the fibroblast seeded gel released from the tissue interface at 3 weeks, where the other groups maintained contact throughout the experiment.

Figure 27:
FIG. 27 is a photomicrograph of the PRP gel at 1 mm from the explanted ACL tissue.
Figure 28:
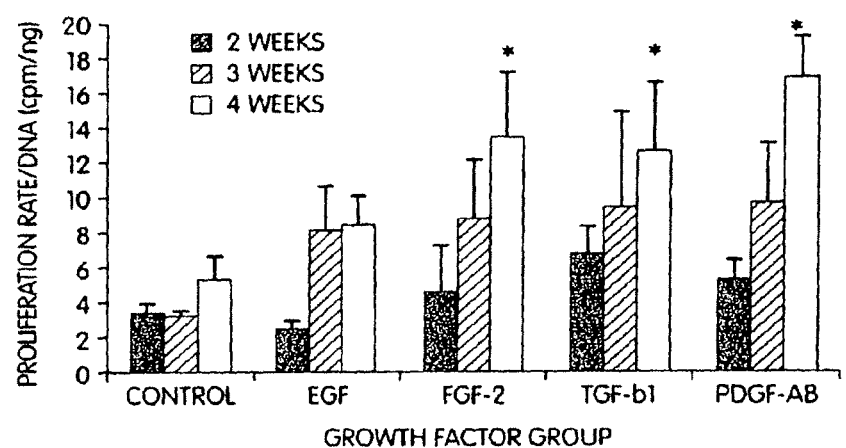
FIG. 28 is a histogram demonstrating cell proliferation in a collagen scaffold with the addition of selected growth factors.

The PRP gel (group 4) demonstrated the greatest contractile potential without releasing from the tissue, suggesting a stronger adhesive property than the fibroblast seeded gel. The histology at two weeks demonstrated the highest cell numbers in groups 1 and 4 (FIG. 27). Thus, the addition of the PRP component did not deter cell migration into the gel. The cells maintained an elongated morphology.

In summary, the PRP and standard hydrogel are similar in encouraging cell ingrowth from surrounding tissue. The PRP gel contracted to a greater extent than the standard hydrogel. The PRP maintained better adhesion to the tissue than the fibroblast seeded gel.

EXAMPLE 20

Resiliency of Platelet Rich Plasma Collagen Hydrogels

The resiliency of the platelet rich plasma collagen hydrogels were assessed using a cyclic stretching machine. Explants were made as in EXAMPLES 17 and 18. The explants were connected by a 3-0 nylon suture loop to prevent excessive tension in the gels. The explants were placed into molds, as in EXAMPLE 18, and the gap between filled with either the gel used in experiments EXAMPLES 17 and 18 (standard gel) or the PRP gel of EXAMPLE 19. Eight constructs were used in each group. After the standard gel had been added to the constructs, it was allowed to set up for 60 minutes at room temperature and media added. For the PRP group, the gel was allowed to set up for 30 minutes at room temperature. After setting, the constructs were transferred into a cyclic stretching machine and cultured for 18 days.

The standard gels all dissolved with motion through the media, suggesting they were not strong enough to resist fluid flow after even one hour at room temperature. In the PRP gel group, 6 of the 8 constructs maintained continuity between explant-PRP gel-explant and were placed into the cycling apparatus. All six constructs maintained contact throughout the 18 days of culture. When removed from the culture, the PRP gel was stretchy and resilient. Thus, the PRP gel is superior to standard hydrogels in resisting dissolution by fluid flow.

EXAMPLE 21

Effect of Platlet Rich Plasma and Matrigel on Collagen Hydrogel

To determine the optimal concentration of PRP and matrigel to use in the collagen hydrogel gel without altering the cell proliferation rates or collagen production rate the following experiments were conducted. Primary outgrowth cells were obtained from one patient undergoing TKR as in EXAMPLE 17. Constructs were made as in EXAMPLE 17. One of five types of gel were added to the molds. The five gel groups were 1. Collagen Hydrogel (standard as used in Expts 1, 2, 3 and 4—contains Matrigel)
2. Group 1+15% PRP
3. Group 1+30% PRP
4. Group 1+45% PRP
5. Group 3 without Matrigel Twenty constructs for each group were cultured and four sacrificed at 2 hours, 1 day, 1 week, 2 weeks and 3 weeks of culture. One construct for each group at each time point was reserved for histology, and the other three labeled with tritiated thymidine (to measure cell proliferation) and 14C proline (to measure collagen production) for 24 hours prior to sacrifice. Minimum gel width was measured each week for all constructs.

EXAMPLE 22

Treatment of Partial ACL Tears In Vivo

Canine ACLs are visualized after routine mini-arthrotomy medial to the patellar tendon and sharply transected with a 3.5 mm beaver blade centrally near the tibial insertion. The partial transection doesn't destabilize the knee and leaves the ACL fibers intact around the central defect. The collagen glue, or no treatment, is placed in the tear. The collagen based glue is prepared by mixing acidic type I collagen with a specified cocktail of growth factors and extracellular matrix proteins optimized for ACL cells. Gelling will be accomplished by neutralizing the pH with NaOH and warming the mixture to room temperature. 2.5 cc of gel is injected into each experimental transection site.

In the right knee of each animal, the collagen glue without growth factors is placed in partial ACL tear and in the left knee, the collagen-based glue containing supplemental growth factors is introduced into partial ACL tear. The knee is closed in a routine fashion.

Animals are allowed free activity once they have awoken from anesthesia.

The dogs are either sacrificed at 10 days, three weeks and six weeks. Ligaments are sharply dissected from their bony insertion sites and fixed in formalin.

After fixation, specimens are embedded in paraffin and longitudinal sections, 7 μm thick, are microtomed and fixed onto glass slides. Representative longitudinal sections microtomed from each ligament are stained with hematoxylin and eosin for cell counting and with antibodies to α-SM actin. In situ hybridization for type I and III collagen is also performed.

The α-SM actin isoform is detected by immunohistochemistry using a monoclonal antibody (Sigma Chemical, St Louis, Mo., USA). Deparaffinized, hydrated slides are digested with 0.1% trypsin (Sigma Chemical, St. Louis, Mo., USA) for twenty minutes. Endogenous peroxide is quenched with 3% hydrogen peroxide for 5 minutes. Nonspecific sites will be blocked using 20% goat serum for 30 minutes. The sections are then incubated with mouse monoclonal antibody to α-SM actin (Sigma Chemical, St. Louis, Mo., USA) for one hour at room temperature. Negative controls are incubated with non-immune mouse serum diluted to the same protein content. The sections are then incubated with a biotinylated goat anti-mouse IgG secondary antibody for 30 minutes followed by thirty minutes of incubation with affinity purified avidin. The labeling is developed using the AEC chromagen kit (Sigma Chemical, St Louis, Mo.) for ten minutes. Counterstaining with Mayer's hematoxylin for 20 minutes will be followed by a 20 minute tap water wash and coverslipping with warmed glycerol gelatin.

Following 24 hour fixation of the tissue in 4% paraformaldehyde at 4° C., the tissue to be used for in situ hybridization is dehydrated, embedded in paraffin, sectioned at 6 μm, and placed on slides. The tissue is deparaffinized in xylene, hydrated in ethanol, and washed in phosphate buffered saline. The tissue sections is fixed with 4% paraformaldehyde at 25° C. for 20 minutes, digested with proteinase K (20 mg/ml) (Sigma Chemical, St Louis, Mo., USA) at 37° C., then postfixed in 4% formaldehyde (Fluka A. G., Buchs, Switzerland). Probes for type-I collagen will be labeled with [32P]deoxycytidine-5-triphosphate (Dupont, Wilmington, Del., USA) by random priming to a specific activity of $0.5-1.5 \times 10^7$ cpm/μg of DNA (Stratagene, La Jolla, Calif., USA). The tissue is hybridized for 20 hours at 42° C., and the slides passed through a series of stringency washes at 37 deg C. for 15 minutes. After dehydration in graded ethanols, the slides are dipped in Ifford K5 emulsion (Polysciences, Warrington, Pa., USA) and exposed for 21 days at 4 deg C. The slides are developed in D19 developer (Eastman Kodak, Rochester, N.Y., USA) and fixed at 15 deg C. Subsequently, the sections are stained with toluidine blue and analyzed and photographed under bright and dark field illumination. For each set of slides, a negative control (pSPT19-neomycin) are used. Relative matrix synthetic activity (type I collagen) within the ligaments are graded by a blinded observer from 1+ to 4+ and further divided by spatial localization of activity.

Histological slides are examined using a Vanox-T AH-2 microscope (Olympus, Tokyo, Japan) with normal and polarized light as previously described (4). Briefly, sections are examined at 2 mm intervals, beginning distal to the femoral insertion site and ending proximal to the tibial insertion site, along the length of fascicles of the anteromedial bundle of each ligament. At each location, 3 0.1 mm$^2$ areas are analyzed for cell number density, and nuclear morphology. At each longitudinal location, the number of crossing vessels will be divided by the width of the section at that location to estimate a blood vessel density. The cell morphology is classified based on nuclear shape: fusiform, ovoid or spheroid. Fibroblasts with nuclei with aspect ratios greater than 10 will be classified as fusiform, those with aspect ratios between 5 and 10 as ovoid, and those with nuclear aspect ratios less than 5 as spheroid. At each location, the total number of cells is counted and divided by the area of analysis to yield a cell density, or cellularity. Cell morphology is mapped for the longitudinal sections and the course of the blood vessels through the section noted.

Smooth muscle cells surrounding vessels are used as internal positive controls for determination of α-SM actin-positive cells. Negative control sections, substituting diluted mouse serum for the primary antibody, will be prepared on each microscope slide to monitor for nonspecific staining. Positive cells will be those that demonstrate chromogen intensity similar to that seen in the smooth muscle cells on the same microscope slide and that had significantly more intense stain than the perivascular cells on the negative control section. Any cell with a questionable intensity of stain (e.g., light pink tint) is not counted as positive. The α-SM actin-positive cell density is reported as the number of stained cells divided by the area of analysis and the percentage of α-SM actin-positive cells is determined by dividing the number of stained cells by the total number of cells in a particular histologic zone.

Polarized light microscopy is used to aid in defining the borders of fascicles and in visualizing the crimp within the fascicles. Measurement of the crimp length is performed using a calibrated scale under polarized light.

Analysis of variance (ANOVA) is performed using statistical software (Statview Version 5.0, SAS Institute, Inc., Cary, N.C., USA). One-factor ANOVA is used to determine the significance of location on the histological parameters for each experimental group individually, and two-factor ANOVA is used to determine the significance of experimental group and location on the histological parameters. Fisher's protected least squares difference (PLSD) is used to determine the significance of differences between groups. The level of significance is set at 95% ($p<0.05$). The data is presented as the mean±the standard error of the mean.

EXAMPLE 23

Effect of the Addition of Insoluble Type I Collagen Fibers to the Soluble Growth Factor Gel on Gel Viscosity Cellular Proliferation, Cellular Collagen Production in the Gel and Cellular Migration Standard growth factor gel is made by mixing 14 cc of acid-soluble, Type I collagen (Cell-A-Gen 0.5%, ICN Pharmaceuticals) with 4 cc of 10× Ham's F10, 4 cc of PCN/Strep, 0.4 ml Fungizone, and 5.4 ml of sterile, distilled water. 6 ml of growth factor cocktail containing FGF-2, TGF-β and PDGF-AB is added to the gel. The above mixture is vortexed, and 6 ml of Matrigel (Becton Dickinson) added. The mixture is vortexed again, and then 0.625 cc of 7.5% NaOH is added to neutralize the gel. The gel is kept on ice until use. The 40 cc of standard gel is divided into four 10 ml aliquots. One of the aliquots is reserved for use with no added insoluble Type I collagen (control). The remaining three aliquots have either 0.01 mg, 0.1 mg or 1 mg of insoluble Type I collagen (Integra Life Sciences, Plainsboro, N.J.) added to each tube and vortexed to mix.

Gel viscosity is determined using a AR1000 controlled stress rheometer (TA Instruments, New Castle, Del.), Rheology Advantage Software (TA Instruments, New Castle, Del.), and a cone and plate geometry. The rheometer is calibrated daily to ensure accuracy. The calibration is performed by comparing the measured viscosity of Cannon Certified Viscosity Standard Mineral Oil to its actual value through the range of 12 Pa to 5 Pa, correcting for temperature variation. The ratio of the given value to the measured value was multiplied by all viscosity results obtained until the next calibration. Previous experiments have shown the calibration ratio to fall within 20% of unity.

Once the calibration is performed, 1.7 ml of the gel to be tested is poured onto the lower plate of the rheometer, which is then raised to within 28 micrometers of the upper plate. Within 30 seconds of gel placement in the rheometer, a fixed torque is applied to the movable cone, resulting in a shear stress that is proportional to the shear strain applied to the fluid. The rheometer measures the steady-state angular velocity of the movable cone. The angular velocity is proportional to the strain rate. The rheology software performs these computations and computes the shear stress and strain rate. The viscosity is measured at a shear stress of 1 Pa. Gel samples are run in triplicate.

ACL cell proliferation and collagen production in the gel is measured as follows.

Human anterior cruciate ligament remnant is obtained from a patient undergoing ACL reconstruction. The ligament is sectioned into 18 explants, each 1-2 mm on a side. The explants are then cultured in a 6 well plate with 1.5 cc of media/well containing high-glucose DMEM, 10% FBS and antibiotics. Media is changed three times a week. After four weeks of culture, the tissue is removed and the cells that grow out of the tissue onto the plate is trypsinized, counted and placed into 2 75 cm² flasks overnight. Prior to gel assembly, the cells are trypsinized and centrifuged. The cells are resuspended in 10 cc of DMEM, counted and divided into 4 equal aliquots of $1\times10^7$ cells each. Each aliquot is re-centrifuged and the media is aspirated, leaving a pellet of cells in a 15 cc centrifuge tube.

ACL cell proliferation and collagen production is determined as follows. Experimental constructs are formed using molds made by cutting 6 mm ID silicon tubing into 1" lengths, then cutting each tube in half to make a trough. Silicon adhesive is used to secure a piece of polyethylene mesh to each end of the trough. The adhesive is allowed to cure overnight, then sterilized by placing into sterile 70% EtOH for 2 hours. The molds are exhaustively rinsed in $dIH_2O$ and placed individually into 6-well plates prior to adding the gel.

Gels are prepared as above. Each gel is added to a different 15 cc tube containing a pellet of $1\times10^7$ ACL cells. The cells are resuspended in the cold gel by gentle mixing with a 1 cc pipette. The gel-cell mixture is then aliquoted into the molds, with 300 µl used in each mold. A drop of the gel-cell mixture is also placed into the bottom of each well to monitor cell survival in the gel. The constructs are allowed to sit at room temperature for 30 minutes, then moved to the 37° C. incubator for 30 minutes. After 1 hour, media containing 10% FBS is added to cover the mold and gel. The cell constructs are cultured at 37° C. and 5% CO2 with media changes three times a week.

At 1 day, 1 week, 2 weeks and 3 weeks of culture, radiolabelling to determine rates of cell proliferation and collagen production is performed. At each time point, three constructs from each group (12 constructs/time point) is radiolabeled with [$^3$H] thymidine and [$^{14}$C] proline. The media is changed and 2 µCI/ml [$^3$H] thymidine and 2 µCi/ml of [$^{14}$C] proline is added to the fresh media in each well. After 24 hours, the media will be removed and the constructs rinsed four times in cold phosphate buffered saline. The gels are placed into separate microcentrifuge tubes and stored at −70° C. The gels are defrosted and digested individually in 1 ml of 0.5% papain/buffer solution (Sigma Chemical, St Louis, Mo., USA) in a 65° C. water bath, and aliquots of each used for the biochemistry assays.

In order to determine the rates of DNA proliferation and collagen synthesis, a 100 µl aliquot is taken from each of the 96 samples and placed into a scintillation vial with 4 cc of scintillation fluid (Fisher Scientific, Chicago, Ill., USA). All samples are counted using a liquid scintillation counter (Tri-Carb 4000 Series, Liquid Scintillation Systems, Model 4640) for both [$^3$H] and [$^{14}$C] with compensation for the beta emission overlap accounted for in the analysis software with a dual label counting program. For anterior cruciate ligament cells, it has been previously demonstrated that 24 to 25% of the uptake of [$^{14}$C] proline is in collagen production, using a modified method of Peterkofsky and Diegelmann. The final wash is also analyzed to ensure it contains less than 0.001% of the radioactivity of the original labeling media.

For DNA analysis, a 500 µl aliquot of the digest is combined with 50 microliters of Hoechst dye no. 33258 and 1 ml of a filtered Tris-EDTA-NaCL buffer solution at pH 7.4 and evaluated fluorometrically. The results are extrapolated from a standard curve using calf thymus DNA (Sigma Chemical, St Louis, Mo., USA). Negative control specimens consisting of the gel alone is also assayed to assess background from the scaffold.

The counts per minute readings for the proliferation and collagen production assays are individually normalized by the DNA content of each sample to give a cell-based proliferation and collagen production rate. These data is used in the statistical analyses. Analysis of variance (ANOVA) is used to determine the statistical significance of the addition of growth factor and time on the histologic and biochemical markers of cell behavior, with Fisher's protected least squares difference used to determine statistical significance of differences between individual groups.

Cellular migration from ACL tissue into the gel is determined using ruptured ACL tissue obtained from patients undergoing ACL reconstruction. The ligaments are sectioned into explants measuring 2 mm on each side. The explants are rinsed exhaustively in sterile PBS and placed in culture media which includes 10% FBS. Explants are maintained in culture media at 37° C. and 5% CO2 overnight. Molds are made by sectioning the 6 mm ID silicon tubing in half to make a trough, and sealing the ends of the trough with agarose, which will be sterilized by autoclaving. The agarose will be melted by placing it in an 80° C. water bath, and then 1 drop is added to each end of the mold. The molds are sterilized by placing in 70% EtOH for 2 hours, then rinsing exhaustively in sterile $H_2O$. Each mold is placed into individual wells of a 6 well plate. One explant is placed into each end of the trough. Each mold holds 200 microliters of liquid. The same four groups of gels as described above are used. The explants and gel will be cultured for 21 days. Media will be changed three times a week. Constructs in each group are sacrificed for histology at days 0, 3, 7, 14 and 21. The constructs used for histology are fixed in 10% neutral buffered formalin for one week, then embedded in paraffin and sectioned at 7 micrometers. Serial sections are stained with hematoxylin and eosin to evaluate cell density and alignment. Cell density is measured in four 0.1 $mm^2$ areas at four locations relative to the tissue/gel interface to determine cell density as a function of location from the tissue. The maximal migration distance within the gel will also be measured for each construct. Two factor ANOVA for gel group and time in culture will be performed to determine the significance of the effect of the fiber reinforcement on cellular density and migration distance.

EXAMPLE 24

Effect of Increased Construct Viscosity on Gel Retention in the ACL Defect in an Ex vivo model The effect of increased construct viscosity on gel retention in the ACL defect is determined using canine knees obtained at the time of sacrifice. All knees have partial transections in the ACL. Knees are treated with the control gel, or gels containing increasing amounts of insoluble collagen fiber. The degree of gel retention is assessed both grossly and histologically. To expose the ACL, a paramedian arthrotomy along the medial border of the patellar tendon is made. The fat pad is swept laterally to expose the ACL. A partial defect is made in the ACL using a transverse cut. After preparation of the defect, the gel components will be mixed as described in EXAMPLE 23.

After preparation of the gels, 100 microliters of the control gel is added to three of the prepared defects. The gel is allowed to set for 10 minutes prior to closure of the knee. This procedure is repeated in 12 knees, using each of the four gel types in three knees. Skin closure is reapproximated using a towel clamp and the knee allowed to rest for 1 hour. After 1 hour has elapsed, the knee is re-opened and the ACL resected sharply from its tibial and femoral insertion sites using an 11 blade.

The ACL is fixed for 24 hours in fresh paraformaldehyde and embedded in paraffin. The twelve ligaments are sectioned longitudinally and serial sections analyzed for degree of filling by the four different gels. A Masson's Trichrome stain will be used to differentiate between the gel and surrounding tissue. The total area of the ligament defect will be measured using a calibrated reticule and the total area of filling measured using the same device. The percentage of filling in 4 sections will be determined and averaged for each specimen. One factor ANOVA for gel type will be used to determine the significance of the effect of gel type on percentage defect filling.

EXAMPLE 25

Effect of Implanting a Reinforced Growth Factor Gel into a Partially Transected ACL on In Vivo Tissue Stimulation A partial ACL transection model will be used for this experiment. In this model, no spontaneous healing of the defect (as measured by gross appearance of defect and mechanical properties) is noted without treatment. Twelve dogs are used, with each dog having gel alone placed into the defect on one limb (control), while the fiber-reinforced growth factor gel is placed into the defect on the opposite limb. Three dogs are sacrificed at day 0, day 10, week 3 and week 6.

Gel Preparation

The control gel (no added insoluble Type I collagen) and the gel with the concentration of insoluble Type I collagen are used in this experiment. To make both gels, all ingredients are kept on ice until placed into the knee. The standard gel is made by mixing 3.5 cc of acid-soluble, Type I collagen (Cell-A-Gen 0.5%, ICN Pharmaceuticals) with 1 cc of 10× Ham's F10, 1 cc of PCN/Strep, 0.1 ml Fungizone, and 1.4 ml of sterile, distilled water. 1.5 ml of growth factor cocktail containing FGF-2, TGF-β and PDGF-AB is added to the gel. The above mixture is vortexed, and 1.4 ml of Matrigel added. The mixture is vortexed again, and then 0.155 cc of 7.5% NaOH is added to neutralize the gel. The fiber-reinforced gel is made by mixing a standard gel, then adding the optimized weight of collagen and vortexing to mix.

Surgical Procedure

For each animal, both knees are exposed. As this procedure does not result in instability of the knee, or require knee immobilization, both knees can be used in each animal. On one side, the fiber reinforced gel is placed into the defect, while of the contralateral side, gel without insoluble Type I collagen is used. To expose the ACL, a 2 cm incision is made along medial border of patellar tendon using a 15 blade. The paratenon is released along the medial edge of the tendon. The fat pad is incised and retracted laterally. Hemostasis is achieved prior to proceeding. A partial defect is made in the ACL and filled with control or fiber-reinforced gel. The tissues is maintained in retraction for 10 minutes and the knees closed using 3-0 PDS in a subcuticular layer as well as a subcuticular closure with running 3-0 PDS. Dogs are kept comfortable in the post-operative period with narcotic medication. No non-steroidal anti-inflammatory medications is nused. Antibiotics are given for 48 hours post-operatively. At 10 days from gel placement, three dogs are sacrificed. The ACLs are sharply resected from their tibial and femoral attachments and placed into fresh 4% paraformaldehyde for 24 hours prior to paraffin embedding. Three additional dogs are sacrificed at 3 weeks and 6 weeks, and the ligaments fixed in paraformaldehyde. Histologic analysis are performed to determine % filling of defect and rate of cell migration into the gel from the surrounding tissue.

Rates of Cellular Migration from the ACL Tissue into the Defect

All ligaments are fixed in cold 4% paraformaldehyde for twenty-four hours, embedded in paraffin and sectioned into 7 micrometer sections. Sections are taken in the sagittal plane to allow for evaluation of the gel in the rupture site and sites 1, 2, 3 and 5 mm from the rupture site. Hematoxylin and eosin and Masson's Trichrome staining is performed to facilitate light microscopy examination of cell morphology and density in the five zones. The cell number density within the gel will be measured in 5 distinct 0.1 mm$^2$ fields and the results averaged and multiplied by 10 to determine the average cell number density within the gel per mm$^2$. Two factor ANOVA is used to determine the significance of fiber reinforcement and time on the cell number density within the gel.

Cell Number Density and Vascularity in the Adjacent Tissue

Histologic parameters of cell number density and nuclear morphology is measured in each histologic zone. The tissue adjacent to the defect is analyzed histomorphometrically as a function of distance from the rupture site. The cell number density, blood vessel density, density of myofibroblasts and nuclear morphology is assessed at each site. The density of blood vessels and myofibroblasts are facilitated by the use of immunohistochemistry for alpha-smooth muscle actin (see protocol below). Plots of the cell number density and blood vessel density, as a function of distance from the growth factor gel site are plotted to illustrate increases in cell number density adjacent to the rupture site. Sections are also analyzed for depth of proteoglycan loss, fascicular fissuring, and synovial loss. Cells that display a pyknotic nucleus and either shrunken, deeply eosinophilic cytoplasm or fragmentation of the nucleus/cytoplasm are counted as apoptotic using histologic criteria. Two factor ANOVA is used to determine the significance of the addition of fiber reinforcement and time on the cell number density, blood vessel density, myofibroblast density and nuclear morphology in the surrounding tissue.

Immunohistochemistry Protocol

Immunohistochemistry for alpha-smooth muscle actin (SMA, marker for myofibroblasts and perivascular cells) is performed as previously reported by our laboratory[22, 23, 25]. In the immunohistochemical procedure, deparaffinized, hydrated slides is digested with 0.1% trypsin (Sigma Chemical, St. Louis, Mo., USA) for twenty minutes. Endogenous peroxidase is quenched with 3% hydrogen peroxide for five minutes. Nonspecific sites are blocked using 20% goat serum for thirty minutes. The sections are incubated with the mouse monoclonal antibody to SMA for one hour at room temperature. A negative control section on each microscope slide is incubated with non-immune mouse serum diluted to the same protein content, instead of the SMA antibody, to monitor for non-specific staining. The sections are incubated with a biotinylated goat anti-mouse IgG secondary antibody for thirty minutes followed by thirty minutes of incubation with affinity purified avidin. The labeling is developed using the AEC chromogen kit (Sigma Chemical, St Louis, Mo.) for ten minutes. Counterstaining with Mayer's hematoxylin for twenty minutes is followed by a twenty-minute tap water wash and coverslipping with warmed glycerol gelatin.

EXAMPLE 26

Effects of the Addition of Growth Factors on the Fibroinductive Properties of a Collagen Scaffold The effect of growth factors to stimulate human ACL cell migration, proliferation, and collagen production was assessed.

Six human ACLs were divided into explants, and the tissue placed into culture with a CG scaffold. Explant/scaffold constructs were cultured with either 2% FBS (control), or 2% FBS supplemented with one of the following: EGF, FGF-2, TGF-β1 or PDGF-AB. Histologic cell distribution, total DNA content, proliferation rate and rate of collagen synthesis were determined at two, three and four weeks.

The ACL cells cultured with EGF and FGF-2 demonstrated a more uniform distribution of cells in the scaffold than the other groups, as well as higher numbers of cells by DNA analysis at the two-week time point. Scaffolds cultured with FGF-2, TGF-β1 or PDGF-AB demonstrated increased rates of cell proliferation (FIG. 4) and collagen production when compared with controls.

These results suggested that certain growth factors can differentially alter the biologic functions of human ACL cells in a collagen matrix implanted as a bridging scaffold at the site of an ACL rupture. Based on these findings, the addition of FGF-2, TGF-β1 or PDGF-AB to an implantable collagen scaffold may facilitate ligament regeneration in the gap between the ruptured ends of the human ACL.

EXAMPLE 27

Survival of Human Anterior Cruciate Ligament Cells in FGF-2 Supplemented Collagen Gel The survival of human anterior cruciate ligament cells in a collagen gel supplemented with FGF-2 was assessed.

Primary outgrowth ACL cells were obtained from explant cultures. The cells were added to a collagen gel containing FGF-2, and the cell-gel mixture placed into silicon molds between two pieces of open polyethylene mesh. Constructs were sacrificed for histology at 3 hours, 3 days and 9 days.

Figure 29:
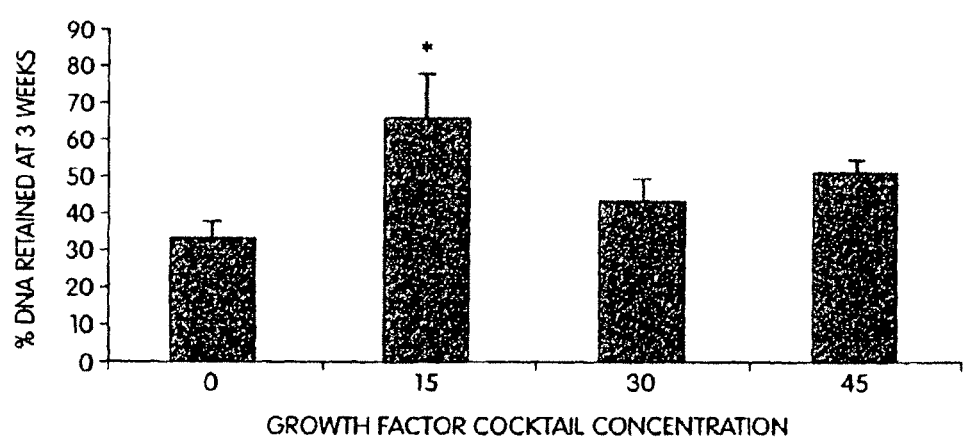
FIG. 29 is a histogram demonstrating the effect of "growth factor cocktail" (GFC) concentration on retention of DNA in the ACL seeded gels after three weeks in culture.

The number of cells in the gel increased with time in culture. By 9 days of culture, the gel constructs had a histologic appearance similar to that of the intact human ACL in terms of cell density and alignment (FIG. 29). The acid-soluble collagen hydrogel with FGF-2 is conducive to human ACL cell growth and proliferation.

EXAMPLE 28

Migration of Human Anterior Cruciate Ligament Cells in FGF-2 Supplemented Collagen Gel The migration of human anterior cruciate ligament cells in a collagen gel supplemented with FGF-2 was assessed.

Explants were placed at each end of a mold and the mold filled with an acellular collagen gel (n=9) or a gel containing ACL fibroblasts (n=9) Constructs in each group were sacrificed for histology at days 0, 3, 7, 14 and 21.

The histologic analysis demonstrated increasing numbers of cells in both the cell gel and the cell free gel. The increase in the cell-seeded gel may have been due to the proliferation of the seeded cells, or to the migration of cells from the tissue into the gel. The initial increase in the cell-free gel was from migration of cells from the ligament tissue. By day 21, the cell density in the two groups was similar. ACL cells will migrate from the tissue into an adjacent collagen gel with containing FGF-2, resulting in similar cell number densities to a cell-seeded gel by three weeks of culture.

EXAMPLE 29

Determination of the Optimal Concentration of "Growth Factor Cocktail" (GFC) to Use in the Gel for Maximum Stimulation of Cell Proliferation and Collagen Production Primary outgrowth cells were obtained from one patient undergoing TKR. Constructs were made as described in EXAMPLE 27 and 28. One of four types of gel were added to the molds. The four gel groups were
1. Collagen Hydrogel with FGF-2 only
2. Group 1+15% GFC
3. Group 1+30% GFC
4. Group 1+45% GFC Twenty constructs for each group were cultured and four sacrificed at 2 hours, 1 day, 1 week, 2 weeks and 3 weeks of culture. One construct for each group at each time point was reserved for histology, and the other three labeled with tritiated thymidine (to measure cell proliferation) and 14C proline (to measure collagen production) for 24 hours prior to sacrifice. Minimum gel width was measured each week for all constructs.

The gel with 15% GFC added had the greatest retention of cells at three weeks (one factor ANOVA, $p=0.05$; Fisher's PLSD with significant differences between groups 1 and 2), suggesting this percentage of GFC is optimal for cell retention and support in the gel. Rates of collagen synthesis were also highest in this group at 2 and 3 weeks of culture. The addition of 15% by volume of the "growth factor cocktail" significantly increased the DNA retention in the gel and also resulted in increased rates of collagen synthesis in the gel.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A scaffold for repair of a tissue defect, comprising a three-dimensional matrix, adapted to facilitate cell in-growth, wherein said matrix is shaped for implantation into a patient at the site of the tissue defect, wherein said matrix comprises a natural matrix material wherein the natural matrix material is a collagen glycosaminoglycan copolymer comprised of collagen type I and wherein said scaffold further comprises plasma.

2. The scaffold of claim 1, wherein the matrix is in the shape of a solid cylindrical member, a cylindrical member having hollow cavities, a tube, or a flat sheet rolled into a tube.

3. The scaffold of claim 1, wherein the matrix further comprises one or more of growth factors, antibiotics, glycosaminoglycans, extracellular matrix protein, platelets, cytokines, neutralizing agents, crosslinking agents, stem cells, or cell media supplements.

4. The scaffold of claim 3, wherein the one or more growth factors are selected from the group consisting of epidermal growth factor (EGF); fibroblast growth factor (FGF); transforming growth factor (TGF); and platelet derived growth factor (PDGF).

5. The scaffold of claim 3, wherein the one or more extracellular matrix proteins are selected from the group consisting of elastin, laminin, fibronectin and entectin.

6. The scaffold of claim 1 wherein the scaffold is resistant to degradation by synovial fluid.

7. The scaffold of claim 1, wherein the scaffold is freeze dried.

8. The scaffold of claim 1, further comprising a mechanical device that is a suture or a clip for attachment of the scaffold to the site of the tissue defect to aid in the repair.

9. A method of treating a tissue defect in a subject, the method comprising placing the scaffold of claim 1 at the site of the tissue defect in the subject.

10. A scaffold for repair of a tissue defect, comprising a three-dimensional collagen matrix, wherein said collagen matrix comprises a collagen polymer comprised of type I collagen and wherein said scaffold further comprises plasma.

11. The scaffold of claim 10, further comprising a mechanical device that is a suture or a clip for attachment of the scaffold to the site of the tissue defect to aid in the repair.

12. The scaffold of claim 10, wherein the collagen matrix is in the form of or forming a tube or cylinder.

13. The scaffold of claim 10, wherein the collagen matrix further comprises collagen or collagen glycosaminoglycan copolymer.

14. The scaffold of claim 10, wherein the collagen matrix comprises one or more growth factors selected from the group consisting of epidermal growth factor (EGF); fibroblast growth factor (FGF); transforming growth factor (TGF); and platelet derived growth factor (PDGF).

15. The scaffold of claim 10, wherein the collagen matrix comprises one or more extracellular matrix proteins selected from the group consisting of elastin, laminin, fibronectin and entectin.

16. The scaffold of claim 10, wherein the tissue defect is an intra-articular tissue defect.

17. The scaffold of claim 16, wherein the intra-articular tissue defect is a partial or complete tear of a ligament exposed to synovial fluid.

18. The scaffold of claim 17, wherein the ligament is an anterior cruciate ligament (ACL).

19. The scaffold of claim 16, wherein the intra-articular tissue defect is of meniscus, cartilage, labrum, tendon, muscle, or bone.

20. A method of treating a tissue defect in a subject, the method comprising placing the scaffold of claim 10 at the site of the tissue defect in the subject.

* * * * *

UNITED STATES PATENT AND TRADEMARK OFFICE
CERTIFICATE OF CORRECTION

PATENT NO. : 8,642,735 B2
APPLICATION NO. : 13/449449
DATED : February 4, 2014
INVENTOR(S) : Martha M. Murray et al.

Page 1 of 1

It is certified that error appears in the above-identified patent and that said Letters Patent is hereby corrected as shown below:

In the Claims:

Column 62 (Claim 13) lines 32-34, should read as:

-- 13. The scaffold of claim 10, wherein the collagen matrix further comprises collagen glycosaminoglycan copolymer. --.

Signed and Sealed this
Thirteenth Day of May, 2014

Michelle K. Lee
*Deputy Director of the United States Patent and Trademark Office*